(12) United States Patent
McCall et al.

(10) Patent No.: US 8,916,561 B2
(45) Date of Patent: *Dec. 23, 2014

(54) SUBSTITUTED QUINOXALINE COMPOUNDS FOR THE INHIBITION OF PASK

(75) Inventors: John M. McCall, Boca Grande, FL (US); Donna L. Romero, Chesterfield, MO (US)

(73) Assignee: BioEnergenix, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/410,720

(22) Filed: Mar. 2, 2012

(65) Prior Publication Data

US 2012/0225863 A1    Sep. 6, 2012

Related U.S. Application Data

(60) Provisional application No. 61/448,550, filed on Mar. 2, 2011.

(51) Int. Cl.
| | | |
|---|---|---|
| *A61K 31/41* | (2006.01) | |
| *A61K 31/498* | (2006.01) | |
| *C07D 241/44* | (2006.01) | |
| *C07D 257/04* | (2006.01) | |
| *A61K 45/06* | (2006.01) | |
| *C07D 241/46* | (2006.01) | |
| *C07D 405/14* | (2006.01) | |
| *C07D 405/04* | (2006.01) | |
| *C07D 403/14* | (2006.01) | |
| *C07D 241/42* | (2006.01) | |
| *C07D 401/04* | (2006.01) | |

(52) U.S. Cl.
CPC .............. *C07D 241/46* (2013.01); *A61K 45/06* (2013.01); *C07D 405/14* (2013.01); *C07D 405/04* (2013.01); *C07D 403/14* (2013.01); *C07D 241/42* (2013.01); *C07D 401/04* (2013.01)
USPC ............ 514/249; 514/381; 544/356; 548/250

(58) Field of Classification Search
CPC ... A61K 31/41; A61K 31/498; C07D 241/44; C07D 257/04
USPC .................... 514/249, 381; 544/356; 548/250
See application file for complete search history.

(56) References Cited

U.S. PATENT DOCUMENTS

| | | |
|---|---|---|
| 6,331,555 B1 | 12/2001 | Hirth |
| 7,189,724 B2 | 3/2007 | An |
| 2003/0059917 A1 | 3/2003 | McKnight |
| 2003/0207886 A1 | 11/2003 | Plucker |
| 2004/0034028 A1 | 2/2004 | Guevel |
| 2008/0194803 A1 | 8/2008 | Sinclair |

FOREIGN PATENT DOCUMENTS

| | | |
|---|---|---|
| CH | 419399 | 3/1967 |
| WO | 2005007099 | 1/2005 |
| WO | 2006076681 A2 | 7/2006 |
| WO | 2006079021 A2 | 7/2006 |
| WO | 2006091395 | 8/2006 |
| WO | 2007146747 A2 | 12/2007 |
| WO | 2010093808 A1 | 8/2010 |
| WO | 2010143168 A2 | 12/2010 |
| WO | 2010143169 A2 | 12/2010 |
| WO | 2010143170 A2 | 12/2010 |
| WO | 2011028947 A3 | 3/2011 |

OTHER PUBLICATIONS

Jordan, V. C. Nature Reviews: Drug Discovery, 2, 2003, 205.*
Hackam, et al. JAMA, 296(14), 2006, 1731-1732.*
Hao, Huai-Xiang, et al. "PAS kinase is required for normal cellular energy balance." Proceedings of the National Academy of Sciences 104.39 (2007): 15466-15471.

* cited by examiner

*Primary Examiner* — Douglas M Willis
(74) *Attorney, Agent, or Firm* — Dennis A. Bennett; Brock Levin

(57) ABSTRACT

Disclosed herein are substituted quinoxaline of Formula (I):

$$
\underset{R_5}{\overset{R_6}{N}} \underset{R_1}{\overset{N}{\underset{N}{\bigg|}}} \underset{R_3}{\overset{R_z}{\bigg|}} \quad (I)
$$

and compositions thereof, which may be useful as inhibitors of PAS Kinase (PASK) activity in a human or animal for the treatment of diseases such as diabetes mellitus.

8 Claims, No Drawings

SUBSTITUTED QUINOXALINE COMPOUNDS FOR THE INHIBITION OF PASK

CROSS REFERENCE TO RELATED APPLICATIONS

This application claims the benefit of priority of U.S. Provisional Application No. 61/448,550, filed Mar. 2, 2011, the disclosure of which is hereby incorporated by reference as if written herein in its entirety.

Disclosed herein are prodrugs of new heterocyclic compounds and compositions and their application as pharmaceuticals for the treatment of disease. Methods of inhibiting PAS Kinase (PASK) activity in a human or animal subject are also provided for the treatment of diseases such as diabetes mellitus.

The regulation of glycogen metabolism is critical for the maintenance of glucose and energy homeostasis in mammals. Glycogen, a large branched polymer of glucose, acts as a reserve of carbon and energy in a variety of organisms. In mammals, the most important stores are found in the liver and skeletal muscle (1). Liver glycogen is required to efficiently buffer blood glucose levels during fasting, whereas muscle glycogen is primarily used locally as a fuel for muscle contraction (2). Dysregulation of glycogen metabolism has been implicated in the development of many diseases, including Type 2 diabetes mellitus (3, 4).

The synthesis of glycogen is primarily controlled through regulation of the enzyme glycogen synthase (GYS, various isoforms), which catalyzes bulk glycogen synthesis (5, 6, 7). The muscle isoform of glycogen synthase (GYS1) is inactivated by reversible phosphorylation that occurs at nine distinct sites within the enzyme (8, 9, 10). In the best characterized form of glycogen synthase, the phosphorylation sites are clustered at the N and C termini (14). Glycogen synthase kinase-3 (GSK-3), an insulin-dependent kinase which has long been implicated in the stepwise phosphorylation of four key sites in the C terminus of glycogen synthase including Ser-640 (one of the most important endogenous regulatory phosphorylation sites in mammalian glycogen synthase (15, 32) and Ser-644 (10, 11-13, 24, 25). GSK-3, however, is not the sole kinase that phosphorylates C-terminal regulatory sites; GSK-3-independent mechanisms also exist, since serine-to-alanine substitutions at Ser-7 and Ser-10 block GSK-3-mediated phosphorylation of the important regulatory sites Ser-640 and Ser-644, and phosphorylation at these sites still occurs.

PASK (purine-analog sensitive kinase, PAS kinase) is a PAS domain-containing serine/threonine kinase, and genetic experiments in S. cerevisiae yeast have implicated PASK as a physiological regulator of glycogen synthase and glycogen accumulation (16, 17). As with the entire glycogen synthase regulatory system, PASK is highly conserved from yeast to man. Human PASK (hPASK) phosphorylates glycogen synthase primarily at Ser-640, causing near complete inactivation. It is interesting to note that the exact site of PASK-dependent phosphorylation is similar but not identical in yeast and mammalian glycogen synthase (18, 19); yeast PASK phosphorylates glycogen synthase at the site analogous to Ser-644, four residues C-terminal (18). It appears that the hPASK mid region (residues 444-955) is required for efficient phosphorylation of glycogen synthase in vitro and for interaction with glycogen synthase in cells: an hPASK mutant (Δ955) lacking the noncatalytic N terminus was unable to efficiently phosphorylate glycogen synthase. Since this region is not required for the phosphorylation of generic, nonphysiological substrates, such as histones and synthetic peptides, it has been proposed that the mid region of hPASK is essential for substrate-targeting. A similar substrate region has been discovered in many protein kinases (26-29). Unlike GSK-3, the activity of hPASK has been shown to be independent of insulin and probably regulated instead by a more direct metabolic signal (23).

Genetic and proteomic screens using yeast PASK identified a number of substrates and implicated this kinase in the regulation of carbohydrate metabolism and translation (18). It has previously been shown that yeast PASK phosphorylates glycogen synthase in vitro and that strains lacking the PASK genes (PSK1 and PSK2) had elevated glycogen synthase activity and an approximately 5- to 10-fold accumulation of glycogen relative to wild-type strains, consistent with impaired ability to phosphorylate glycogen synthase in vivo (18). Because glycogen synthesis and translation are two processes tightly regulated in response to nutrient availability and because PAS domains are frequently involved in metabolic sensing, a role for PASK in the cellular response to metabolic status has been proposed. Indeed, it was recently demonstrated that mammalian PASK plays a role in the cellular response to nutrients.

The catalytic activity of PASK in pancreatic islet β-cells is rapidly increased in response to glucose addition, and PASK is required for the glucose-responsive expression of some β-cell genes, including preproinsulin (23).

PASK catalytic activity is not responsive to glucose alone, however. The interaction between the hPASK midregion and glycogen synthase is regulated by at least two factors. First, the PAS domain of PAS kinase plays a negative role in regulating this interaction. If the PAS domain is deleted or disrupted, hPASK associates more stably with glycogen synthase. PAS domain function is usually controlled by the metabolic status of the host cell, as has been suggested for the PASK PAS domain (23). This observation raises the intriguing possibility that the hPASK-glycogen synthase interaction is regulated by the metabolic status of the cell, thereby enabling an additional layer of metabolic regulation of glycogen synthesis. Second, glycogen negatively regulates the hPASK-glycogen synthase interaction, which would initially seem counterintuitive, since glycogen would thereby stimulate its own continued synthesis. It is possible, however, that this mechanism exists to spatially coordinate the synthesis of glycogen. It is becoming increasingly apparent that glycogen is synthesized in cells in a highly organized spatial pattern (30). Perhaps one function of hPASK is to maintain free, unlocalized glycogen synthase in a phosphorylated, inactive form until it is properly localized to an existing, properly organized glycogen particle. These data strongly suggest that the hPASK midregion plays an important role in targeting hPASK catalytic activity to specific substrates within the cell.

Since hPASK has been recently implicated in glucose-sensing and glucose-responsive transcription, it appears likely that glucose signaling by means of hPASK affects glycogen metabolism in vivo. It is well established that derangement in glycogen metabolism is one of the hallmarks of both Type 1 and Type 2 diabetes (20) and related conditions (21), including a panoply of life-threatening cardiovascular conditions (22). Using PASK1 mice, it has further been demonstrated that PASK is indeed required for normal insulin secretion by pancreatic β cells, and that PASK deletion results in nearly complete resistance to the phenotypes caused by a high-fat diet, including obesity, insulin resistance and hepatic fat accumulation. Therefore, PASK inhibition would comprise a system for the metabolic control of glucose utilization and storage in mammalian cells, and offer a new method to treat metabolic diseases including but not limited to diabetes and its complications, the metabolic syndrome, insulin resistance, and various cardiovascular conditions.

The hallmarks of cancer, cellular overgrowth and hyperproliferation, require the rapid synthesis of all cellular materials, including protein and lipids. Both of these synthetic processes are controlled, to some extent, by PASK. As a result of these observations, it is possible that inhibition of PASK could be a viable therapeutic strategy for many cancers. By preventing the rapid synthesis of proteins and lipids, such an inhibitor should prevent the rapid and uncontrolled growth and division of cells that characterizes many cancers.

DETAILED DESCRIPTION OF THE INVENTION

Novel compounds and pharmaceutical compositions, certain of which have been found to inhibit PASK have been discovered, together with methods of synthesizing and using the compounds including methods for the treatment of PASK-mediated diseases in a patient by administering the compounds.

Though PASK inhibitors as a class of compounds appear promising in the treatment of PASK-mediated diseases, much work remains to be done in the characterization, development, and selection of a compound suitable for use in humans. Room for improvement is still apparent in the design of analogues which have the optimal balance of bioavailability and other pharmacokinetic parameters, solubility, ICE, target tissue penetration, favorable metabolism and toxicology, and other attributes for the purpose of providing safe and effective compounds which will be easy to use by patients and clinicians alike. Additionally, many factors still influence the suitability of a compound as a pharmaceutical agent in general. For example, to be ideally suited for delivery to patients, compounds should be readily uptaken by the patient's body via the chosen route of administration, should be soluble and bioavailable to the target compartment or organ, and should be cleared from the body in an appropriate period of time. The design of prodrugs presents opportunities for improvements in each of these areas.

In certain embodiments of the present invention, a pharmaceutical composition comprises a compound having structural Formula I:

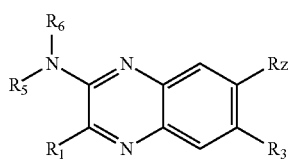

(I)

or a salt or stereoisomer thereof, wherein:
Rz is chosen from $COOR_8$, $COSR_8$, $CONR_8R_9$, $NHSO_2R_8$, $SO_2NR_8R_9$, $SO_3R_8$, tetrazolyl, and $COONR_8R_9$;

$R_1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $SO_2R_{12}$, $SO_2NHR_{12}$, $CF_3$, and $OCF_3$;

$R_3$ is chosen from hydrogen, hydroxyl, halo, $C_1$-$C_5$ alkyl, and $C_1$-$C_5$ alkoxy, any of which may be optionally substituted;

$R_5$ and $R_6$ are independently chosen from hydrogen, $C_1$-$C_6$ alkyl, $C_1$-$C_7$ cycloalkyl, $C_1$-$C_7$ heterocycloalkyl, $C_1$-$C_6$ alkenyl, $C_1$-$C_6$ alkynyl, aryl, heteroaryl, aralkyl, haloalkyl, and heteroaralkyl, or taken together, $R_5$ and $R_6$ may form a heterocycloalkyl or heteroaryl, any of which may be optionally substituted;

$R_8$ and $R_9$ are each independently chosen from hydrogen, $C_1$-$C_6$ alkyl, aryl, heteroaryl, aralkyl, amidoalkyl, aminoalkyl, hydroxyalkyl, oxyalkyl, alkoxyalkyl, alkylamidoalkyl, alkylaminoalkyl, acyloxyalkyl and heteroaralkyl, or taken together, $R_8$ and $R_9$ may form a heterocycloalkyl or heteroaryl, any of which may be optionally substituted, wherein if Rz is $COOR_8$, then $R_8$ is not hydrogen; and $R_{12}$, $R_{12a}$ and $R_{12b}$ are independently chosen from hydrogen, $C_1$-$C_6$ alkyl, aryl, heteroaryl, aralkyl, $CF_3$ and heteroaralkyl, any of which may be optionally substituted.

Certain compounds and prodrugs disclosed herein may possess useful PASK modulating activity, and may be used in the treatment or prophylaxis of a disease or condition in which PASK plays an active role. Thus, in broad aspect, certain embodiments also provide pharmaceutical compositions comprising one or more compounds and prodrugs disclosed herein together with a pharmaceutically acceptable carrier, as well as methods of making and using the compounds and prodrugs and compositions. Certain embodiments provide methods for modulating PASK. Other embodiments provide methods for treating a PAS K-mediated disorder in a patient in need of such treatment, comprising administering to said patient a therapeutically effective amount of a compound or composition according to the present invention. Also provided is the use of certain compounds and prodrugs disclosed herein for use in the manufacture of a medicament for the treatment of a disease or condition ameliorated by the inhibition of PASK.

In further embodiments, pharmaceutical compositions comprising a compound of Formula I are provided wherein
$R_1$ is phenyl and has one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy and $OCF_3$; and $R_{12}$, $R_{12a}$ and $R_{12b}$ are independently chosen from hydrogen, $C_1$-$C_6$ alkyl, aryl, heteroaryl, aralkyl and heteroaralkyl, any of which may be optionally substituted.

In certain embodiments pharmaceutical compositions comprising a compound of Formula I are provided wherein $R_5$ and $R_6$ are independently $C_1$-$C_6$ alkyl, cycloalkyl, heterocycloalkyl, and aryl, or taken together, $R_5$ and $R_6$ may form a heterocycloalkyl, any of which may be optionally substituted.

In certain embodiments pharmaceutical compositions comprising a compound of Formula I are provided wherein $R_3$ is hydrogen.

In certain embodiments pharmaceutical compositions comprising a compound of Formula I are provided wherein $R_5$ and $R_6$ are independently $C_1$-$C_6$ alkyl, or taken together, $R_5$ and $R_6$ may form a heterocycloalkyl which may be optionally substituted.

In certain embodiments of the present invention, a pharmaceutical composition comprises a compound having structural Formula II:

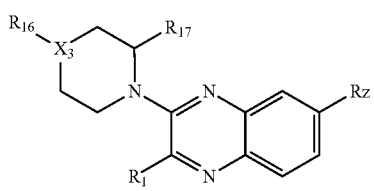

(II)

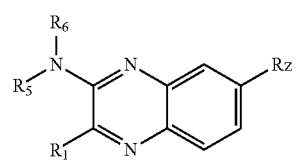

(III)

or a salt or stereoisomer thereof, wherein:

$Rz$ is chosen from $COOR_8$, $COSR_8$, $CONR_8R_9$, $NHSO_2R_8$, $SO_2NR_8R_9$, $SO_3R_8$, tetrazolyl, and $COONR_8R_9$;

$R_1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $CF_3$, $SO_2R_{12}$, $NHSO_2R_{12}$, and $OCF_3$;

$R_8$ and $R_9$ are each independently chosen from hydrogen, $C_1$-$C_6$ alkyl, aryl, heteroaryl, aralkyl, amidoalkyl, aminoalkyl, hydroxyalkyl, oxyalkyl, alkoxyalkyl, alkylamidoalkyl, alkylaminoalkyl, acyloxyalkyl and heteroaralkyl, or taken together, $R_8$ and $R_9$ may form a heterocycloalkyl or heteroaryl, any of which may be optionally substituted, wherein if $Rz$ is $COOR_8$, then $R_8$ is not hydrogen;

$R_{12}$, $R_{12a}$ and $R_{12b}$ are independently chosen from hydrogen, $C_1$-$C_6$ alkyl, aryl, heteroaryl, aralkyl and heteroaralkyl, any of which may be optionally substituted;

$R_{16}$ is chosen from null, hydrogen, alkyl, cycloalkyl, heterocycloalkyl, aryl, and heteroaryl any of which may be optionally substituted;

$R_{17}$ is chosen from hydrogen, $C_1$-$C_6$ alkyl, and $C_1$-$C_6$ haloalkyl; and $X_3$ is chosen from CH, N, O, and a bond.

In further embodiments, pharmaceutical compositions comprising a compound of Formula II are provided wherein $R_1$ is aryl, which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $CF_3$, $SO_2R_{12}$, $NHSO_2R_{12}$, and $OCF_3$.

In further embodiments, pharmaceutical compositions comprising a compound of Formula II are provided wherein $R_1$ is aryl optionally substituted with one or more halo substituents.

In further embodiments, pharmaceutical compositions comprising a compound of Formula II are provided wherein $X_3$ is chosen from CH and N.

In further embodiments, pharmaceutical compositions comprising a compound of Formula II are provided wherein $R_{16}$ is hydrogen.

In further embodiments, pharmaceutical compositions comprising a compound of Formula II are provided wherein $X_3$ is O and $R_{16}$ is null.

In certain embodiments of the present invention, a pharmaceutical composition comprises a compound having structural Formula III:

or a salt or stereoisomer thereof, wherein:

$Rz$ is chosen from $COOR_S$, $COSR_8$, $CONR_8R_9$, $NHSO_2R_8$, $SO_2NR_8R_9$, $SO_3R_8$, tetrazolyl, and $COONR_8R_9$;

$R_1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $SO_2R_{12}$, $SO_2NHR_{12}$, $CF_3$, and $OCF_3$;

$R_5$ and $R_6$ are independently chosen from hydrogen, $C_1$-$C_6$ alkyl, $C_1$-$C_7$ cycloalkyl, $C_1$-$C_7$ heterocycloalkyl, aryl, heteroaryl, aralkyl, and heteroaralkyl, any of which may be optionally substituted; and $R_8$ and $R_9$ are each independently chosen from hydrogen, $C_1$-$C_6$ alkyl, aryl, heteroaryl, aralkyl, amidoalkyl, aminoalkyl, hydroxyalkyl, oxyalkyl, alkoxyalkyl, alkylamidoalkyl, alkylaminoalkyl, acyloxyalkyl and heteroaralkyl, or taken together, $R_8$ and $R_9$ may form a heterocycloalkyl or heteroaryl, any of which may be optionally substituted, wherein if $Rz$ is $COOR_8$, then $R_8$ is not hydrogen;

$R_{12}$, $R_{12a}$ and $R_{12b}$ are independently chosen from hydrogen, $C_1$-$C_6$ alkyl, aryl, heteroaryl, aralkyl, $CF_3$ and heteroaralkyl, any of which may be optionally substituted.

In another embodiment, pharmaceutical compositions comprising a compound of Formula III are provided wherein $R_1$ is aryl, which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $CF_3$, $SO_2R_{12}$, $NHSO_2R_{12}$, and $OCF_3$.

In another embodiment, pharmaceutical compositions comprising a compound of Formula III are provided wherein $R_1$ is aryl optionally substituted with one or more halo substituents.

In another embodiment, pharmaceutical compositions comprising a compound of Formula III are provided wherein $R_5$ and $R_6$ are independently chosen from hydrogen, $C_1$-$C_6$ alkyl, $C_1$-$C_7$ cycloalkyl, $C_1$-$C_7$ heterocycloalkyl, and aryl, any of which may be optionally substituted.

In an embodiment of the present invention, a pharmaceutical composition comprises a compound having structural Formula IV:

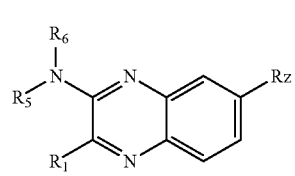

(IV)

or a salt or stereoisomer thereof, wherein:

$R_z$ is tetrazolyl;

$R_1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $SO_2R_{12}$, $SO_2NHR_{12}$, $CF_3$, and $OCF_3$;

$R_5$ and $R_6$ are independently chosen from hydrogen, $C_1$-$C_6$ alkyl, $C_1$-$C_7$ cycloalkyl, $C_1$-$C_7$ heterocycloalkyl, aryl, heteroaryl, aralkyl, and heteroaralkyl, any of which may be optionally substituted; and $R_{12}$, $R_{12a}$ and $R_{12b}$ are independently chosen from hydrogen, $C_1$-$C_6$ alkyl, aryl, heteroaryl, aralkyl, $CF_3$ and heteroaralkyl, any of which may be optionally substituted.

In another embodiment, pharmaceutical compositions comprising a compound of Formula IV are provided wherein $R_1$ is aryl, which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $CF_3$, $SO_2R_{12}$, $NHSO_2R_{12}$, and $OCF_3$.

In another embodiment, pharmaceutical compositions comprising a compound of Formula IV are provided wherein $R_1$ is aryl optionally substituted with one or more halo substituents.

In another embodiment, pharmaceutical compositions comprising a compound of Formula IV are provided wherein $R_5$ and $R_6$ are independently chosen from hydrogen, $C_1$-$C_6$ alkyl, $C_1$-$C_7$ cycloalkyl, $C_1$-$C_7$ heterocycloalkyl, and aryl, any of which may be optionally substituted.

Further provided is a pharmaceutical composition as disclosed above for use as a medicament.

Further provided is a pharmaceutical composition as disclosed above for use in the manufacture of a medicament for the prevention or treatment of a disease or condition ameliorated by the inhibition of PASK.

Further provided is a pharmaceutical composition as disclosed above for use in the manufacture of a medicament for the prevention or treatment of a disease or condition ameliorated by the inhibition of PASK.

Further provided is a pharmaceutical composition comprising a compound having structural formula I together with a pharmaceutically acceptable carrier.

Further provided is a method of inhibiting PASK comprising contacting PASK with a pharmaceutical composition as disclosed above.

Further provided is a method of treatment of a disease comprising the administration of a therapeutically effective amount of a pharmaceutical composition as disclosed above to a patient in need thereof.

Further provided is the method as recited above wherein said disease is chosen from cancer and a metabolic disease.

Further provided is the method as recited above wherein said disease is a metabolic disease.

Further provided is the method as recited above wherein said metabolic disease is chosen from metabolic syndrome, diabetes, dyslipidemia, fatty liver disease, non-alcoholic steatohepatitis, obesity, and insulin resistance.

Further provided is the method disclosed above wherein said diabetes is Type II diabetes.

Further provided is the method as disclosed above wherein said dyslipidemia is hyperlipidemia.

Further provided is a method for achieving an effect in a patient comprising the administration of a therapeutically effective amount of a pharmaceutical composition as disclosed above to a patient, wherein the effect is selected from the group consisting of reduction of triglycerides, reduction of cholesterol, and reduction of hemoglobin A1c.

Further provided is the method as disclosed above wherein said cholesterol is chosen from LDL and VLDL cholesterol.

Further provided is the method as disclosed above wherein said triglycerides are chosen from plasma triglycerides and liver triglycerides.

Further provided is a method of treatment of a PASK-mediated disease comprising the administration of:

a. a therapeutically effective amount of a pharmaceutical composition as disclosed above; and b. another therapeutic agent.

Not to be bound by any theory or mechanism, the compounds disclosed herein can be used to treat or modulate metabolic disease (including but not limited to diabetes, metabolic disorder, dyslipidemia, fatty liver disease, non-alcoholic steatohepatitis, obesity, and insulin resistance, as well as to reduce triglycerides, cholesterol, and hemoglobin A1c) and cancer.

As used herein, the terms below have the meanings indicated.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—$NR_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino ($CH_3$C(O) NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group. The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 3 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain hydrocarbon radical, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be substituted or quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, 3,4-methylenedioxyphenyl and the like. The heterocycle groups may be optionally substituted unless specifically prohibited.

The term "hydrazinyl" as used herein, alone or in combination, refers to two amino groups joined by a single bond, i.e., —N—N— and not embodied in a ring.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethoxy" refers to a X$_3$CO— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aralkyl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds and prodrugs disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds and prodrugs can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds and prodrugs disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds and prodrugs disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"PASK inhibitor" as used herein refers to a compound that exhibits an ($IC_{50}$/$EC_{50}$) with respect to PASK activity of no more than about 100 µM and more typically not more than about 50 µM, as measured in the PASK assay described generally hereinbelow. $IC_{50}$ is that concentration of inhibitors which reduces the activity of PASK to half-maximal level. Certain compounds and prodrugs disclosed herein have been discovered to exhibit inhibition against PASK.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds and prodrugs disclosed herein can exist as therapeutically acceptable salts. The present invention includes compounds and prodrugs listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds and prodrugs disclosed herein which are water or oil-soluble or dispersible and therapeutically acceptable as defined herein. The salts can be prepared during the final isolation and purification of the compounds or separately by reacting the appropriate compound in the form of the free base with a suitable acid.

While it may be possible for the compounds and prodrugs of the subject invention to be administered as the raw chemical, it is also possible to present them as a pharmaceutical formulation. Accordingly, provided herein are pharmaceutical formulations which comprise one or more of certain compounds and prodrugs disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds and prodrugs disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds and prodrugs may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds and prodrugs which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds and prodrugs to allow for the preparation of highly concentrated solutions.

In addition to the formulations described previously, the compounds and prodrugs may also be formulated as a depot preparation. Such long acting formulations may be administered by implantation (for example subcutaneously or intramuscularly) or by intramuscular injection. Thus, for example, the compounds and prodrugs may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds and prodrugs may also be formulated in rectal compositions such as suppositories or retention enemas, e.g., containing conventional suppository bases such as cocoa butter, polyethylene glycol, or other glycerides.

Certain compounds and prodrugs disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds and prodrugs may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds and prodrugs according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds and prodrugs may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds and prodrugs can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds and prodrugs described herein with another therapeutic agent (which also includes a therapeutic regimen) that also has therapeutic benefit. By way of example only, in a treatment for diabetes involving administration of one of the compounds and prodrugs described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of a compound as disclosed herein, and at least one other agent selected from the group comprising:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidinedione derivative (glitazone) such as pioglitazone or rosiglitazone; and a non-glitazone type PPARδ agonist e.g. GI-262570;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor), PXR (pregnane X receptor) and LXR (liver X receptor) ligands; cholestyramine; fibrates; nicotinic acid and aspirin;

c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists;

d) anti-hypertensive agents, e.g., loop diuretics such as ethacrynic acid, furosemide and torsemide; diuretics such as thiazide derivatives, chlorothiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutral endopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, tehnisartan and valsartan, in particular valsartan; renin inhibitors such as aliskiren, terlakiren, ditekiren, RO 66-1132, RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

e) an HDL increasing compound;

f) cholesterol absorption modulator such as etizimibe and KT6-971;

g) Apo-A1 analogues and mimetics;

h) thrombin inhibitors such as Ximelagatran;

i) aldosterone inhibitors such as anastrazole, fadrazole, and eplerenone;

j) inhibitors of platelet aggregation such as aspirin, and clopidogrel bisulfate;

k) estrogen, testosterone, a selective estrogen receptor modulator, and a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, and compounds decreasing the protein kinase activity such as a PDGF receptor tyrosine kinase inhibitor such as miatinib; and m) an agent interacting with a 5-HT3 receptor and/or an agent interacting with 5-HT4 receptor such as tegaserod described in the U.S. Pat. No. 5,510,353 as example 13, tegaserod hydrogen maleate, cisapride, and cilansetron.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PASK-mediated disorders in a human or animal subject in need of such treatment comprising administering to said subject an amount of a compound disclosed herein effective to reduce or prevent said disorder in the subject, optionally in combination with at least one additional agent that is known in the art. In a related aspect, certain embodiments provide therapeutic compositions comprising at least one compound disclosed herein in combination with one or more additional agents for the treatment of PASK-mediated disorders.

Recent studies have found that elevated medium glucose concentrations caused post-translational activation of PASK. It has also been demonstrated that PASK activity is required for glucose-stimulated insulin expression, as shown by studies in PASK1 mice. It has also been demonstrated that PASK deletion results in nearly complete resistance to the phenotypes caused by a high-fat diet, including obesity, insulin resistance and hepatic fat accumulation. It appears that PASK inhibition can provide an effective therapeutic strategy for the treatment of diseases, for example Type 2 diabetes, insulin resistance in general, and the metabolic syndrome.

Metabolic syndrome (also known as metabolic syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL—less than 40 mg/dL; pro-thrombotic state (e.g. high fibrinogen or plasminogen activator inhibitor in the blood); or blood pressure of 130/85 mmHg or higher. A connection has been found between metabolic syndrome and other conditions such as obesity, high blood pressure and high levels of LDL cholesterol, all of which are risk factors for cardiovascular diseases. For example, an increased link between metabolic syndrome and atherosclerosis has been shown. People with metabolic syndrome are also more prone to developing Type 2 diabetes, as well as PCOS (polycystic ovarian syndrome) in women and prostate cancer in men.

As described above, insulin resistance can be manifested in several ways, including Type 2 diabetes. Type 2 diabetes is the condition most obviously linked to insulin resistance. Compensatory hyperinsulinemia helps maintain normal glucose levels—often for decades, before overt diabetes develops. Eventually the beta cells of the pancreas are unable to overcome insulin resistance through hypersecretion. Glucose levels rise, and a diagnosis of diabetes can be made. Patients with Type 2 diabetes remain hyperinsulinemic until they are in an advanced stage of disease. As described above, insulin resistance can also correlate with hypertension. One half of patients with essential hypertension are insulin resistant and hyperinsulinemic, and there is evidence that blood pressure is linked to the degree of insulin resistance. Hyperlipidemia, too, is associated with insulin resistance. The lipid profile of patients with Type 2 diabetes includes increased serum very-low-density lipoprotein cholesterol and triglyceride levels and, sometimes, a decreased low-density lipoprotein cholesterol level. Insulin resistance has been found in persons with low levels of high-density lipoprotein. Increased insulin levels have also been linked to high very-low-density lipoprotein synthesis and increased plasma triglyceride levels.

Accordingly, also disclosed are methods of treating insulin resistance in a subject comprising selecting a subject in need of treatment for insulin resistance; and administering to the subject an effective amount of a compound that inhibits PASK.

Specific diseases to be treated by the compounds and prodrugs, compositions, and methods disclosed herein are those mediated at least in part, directly or indirectly, by PASK. Accordingly, disclosed herein are methods: for reducing glycogen accumulation in a subject; for raising HDL or HDLc, lowering LDL or LDLc, shifting LDL particle size from small dense to normal LDL, lowering VLDL, lowering triglycerides, or inhibiting cholesterol absorption in a subject; for reducing insulin resistance, enhancing glucose utilization or lowering blood pressure in a subject; for reducing visceral fat in a subject; for reducing serum transaminases in a subject; for reducing hemoglobin A1c in a subject; or for treating disease; all comprising the administration of a therapeutic amount of a compound as described herein, to a patient in need thereof. In further embodiments, the disease to be treated may be a metabolic disease. In further embodiments, the metabolic disease may be chosen from: obesity, diabetes melitus, especially Type 2 diabetes, hyperinsulinemia, glucose intolerance, metabolic syndrome X, dyslipidemia, hypertriglyceridemia, hypercholesterolemia, and hepatic steatosis. In other embodiments, the disease to be treated may be chosen from: cardiovascular diseases including vascular disease, atherosclerosis, coronary heart disease, cerebrovascular disease, heart failure and peripheral vessel disease. In preferred embodiments, the methods above do not result in the induction or maintenance of a hypoglycemic state.

In further embodiments, the metabolic disease may be a neurological disease known to be associated with metabolic disease and/or insulin resistance, such as Alzheimer's disease.

Additionally, the PASK modulators disclosed herein may be used to treat proliferative disorders such as cancers. Hematological and non-hematological cancers which may be treated or prevented include but are not limited to multiple myeloma, acute and chronic leukemias including Acute Lymphocytic Leukemia (ALL), Chronic Lymphocytic Leukemia (CLL), and Chronic Myelogenous Leukemia (CML), lymphomas, including Hodgkin's lymphoma and non-Hodgkin's lymphoma (low, intermediate, and high grade), malignancies of the brain, head and neck, breast, lung, reproductive tract, upper digestive tract, pancreas, liver, renal, bladder, prostate and colon/rectum.

Besides being useful for human treatment, certain compounds and prodrugs and formulations disclosed herein may also be useful for veterinary treatment of companion animals, exotic animals and farm animals, including mammals, rodents, and the like. More preferred animals include horses, dogs, and cats.

REFERENCES CITED

This application incorporates by reference United States Non-Provisional application Ser. No. 12/874,967, filed Sep. 2, 2010, the disclosure of which is hereby incorporated by reference as if written herein in its entirety. The following is a list of references cited herein which, while not necessarily comprehensive, is provided for the convenience of the reader. All references, patents, and patent applications cited herein are hereby incorporated by reference as if written herein in their entireties. When the teachings of these references contradict the teachings presented expressly herein, the present disclosure controls.

1. Roach, P. J. et al. (2001) in The Endocrine Pancreas and Regulation of Metabolism, eds. Chemington, A. D. & Jefferson, L. S. (Oxford Univ. Press, New York), pp. 609-647.
2. Bergstrom, J. et al. (1967) Acta Physiol. Scand. 71: 140-150.
3. Cline, G. W. et al. (1994) J. Clin. Invest. 94: 2369-2376.
4. Shulman, G. I. et al. G. (1990) N. Engl. J. Med. 322: 223-228.
5. Cohen, P. (1982) Nature 296: 613-620.
6. Roach, P. J. (1986) in The Enzymes, eds. Boyer, P. D. & Krebs, E. G. (Academic, Orlando, Fla.), Vol. 17: pp. 499-539.
7. Cohen, P. (1986) in The Enzymes, eds. Boyer, P. D. & Krebs, E. G. (Academic, Orlando, Fla.), Vol. 17: pp. 461-497.
8. Friedman, D. L. & Larner, J. (1963) Biochemistry 128: 669-675.
9. Larner, J. (1990) Adv. Enzymol. Relat. Areas Mol. Biol. 63: 173-231.
10. Roach, P. J. (1990) FASEB J. 4: 2961-2968.
11. Skurat, A. V., et al. (1994) J. Biol. Chem. 269: 25534-25542.
12. Flotow, H. & Roach, P. J. (1989) J. Biol. Chem. 264: 9126-9128.
13. Nakielny, S., Campbell, D. G. & Cohen, P. (1991) Eur. J. Biochem. 199: 713-722.
14. Wilson W A et al., Proc Natl Acad Sci USA. 2005 Nov. 15; 102(46):16596-601, FIG. 6
15. Skurat, A. V. & Roach, P. J. (1995) J. Biol. Chem. 270: 12491-12497.
16. Hardy, T. A. & Roach, P. J. (1993) J. Biol. Chem. 268: 23799-23805
17. Francois, J. & Parrou, J. L. (2001) FEMS Microbiol. Rev. 25: 125-145.
18. Rutter, J., Probst, B. L. & McKnight, S. L. (2002) Cell 111: 17-28.
19. Rutter, J et al. (2001) Proc. Natl. Acad. Sci. USA 98: 8991-8996.
20. Roden M, Bernroider E: *Best Pract Res Clin Endocrinol Metab.* 2003 September; 17(3):365-83
21. Van Steenbergen W, Lanckmans S: *Int J Obes Relat Metab Disord.* 1995 September; 19 Suppl 3:S27-36.
22. Arad M et al., *Circ Res.* 2007 Mar. 2; 100(4):474-88
23. da Silva Xavier, G. et al. (2004) Proc. Natl. Acad. Sci. USA 101: 8319-8324.
24. Picton, C. et al. (1982) FEBS Lett. 150: 191-196.
25. DePaoli-Roach, A. A. et al., (1983) J. Biol. Chem. 258: 10702-10709.
26. Elia, A. E. et al. (2003) Science 299: 1228-1231.
27. Gao, T. et al. (1997) Neuron 19: 185-196.
28. Wilson, W. A. et al. (1999) Mol. Cell. Biol. 19: 7020-7030.
29. Yedovitzky, M. et al. (1997) J. Biol. Chem. 272: 1417-1420.
30. Fernandez-Novell, J. M., et al. (2002) FEBS Lett. 531: 222-228.
31. Hao H-X. et al., "PAS kinase is required for normal cellular energy balance," *Proc. Natl. Acad. Sci.* (USA) v104, pp 15466-15471, 2007.
32. Horton J D. et al., "Regulation of sterol regulatory element binding proteins in livers of fasted and refed mice," *Proc. Natl. Acad. Sci.* (USA) v95, pp 5987-5992, 1998.
33. Evans M J et al., "A synthetic farnesoid X receptor (FXR) agonist promotes cholesterol lowering in models of dyslipidemia," *Am. J. Physiol. Gastrointest. Liver Physiol.* V296, G543-G552, 2009.
34. Hartman, H B. Et al., "Activation of farnesoid X receptor prevents atherosclerotic lesion formation in $LDLR^{-/-}$ and $apoE^{-/-}$ mice," *J. Lipid Res.*, v50, 1090-1100, 2009.
35. Zhang, S. et al., "Farnesoid X receptor agonist WAY-362450 attenuates liver inflammation and fibrosis in murine model of non-alcoholic steatohepatitis," *J. of Hepatology*, v51, 380-388, 2009.
36. Flatt, B. et al., "Discovery of XL335 (WAY-362450), a Highly Potent, Selective, and Orally Active Agonist of the Farnesoid X Receptor," *J. Med. Chem.*, v52, 904-907, 2009.

GENERAL SYNTHETIC METHODS FOR PREPARING COMPOUNDS

The following schemes can generally be used to practice the present invention.

Scheme I

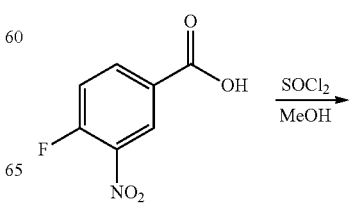

-continued

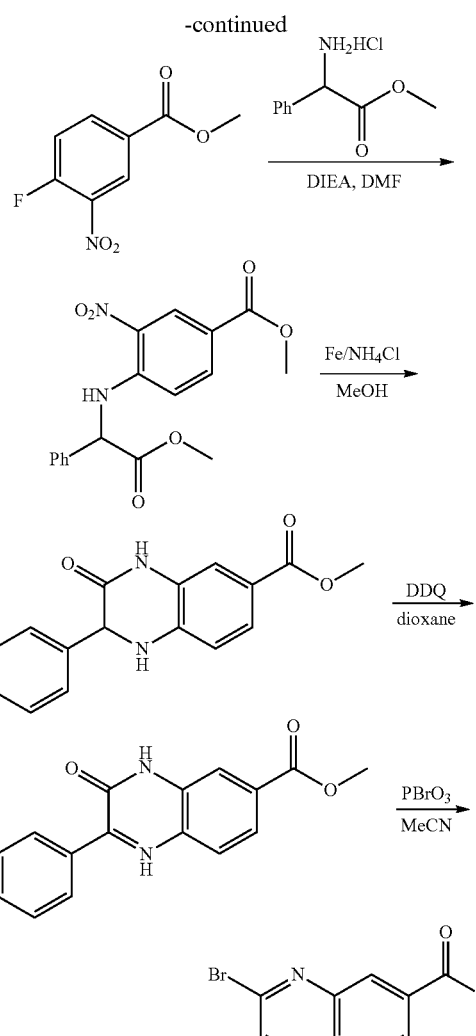

Step 1

Synthesis of methyl 4-fluoro-3-nitrobenzoate

Thionyl chloride (6.5 g, 54.62 mmol, 1.01 equiv) was added dropwise, with stirring at 0° C., to a methanolic solution (60 mL) of 4-fluoro-3-nitrobenzoic acid (10 g, 54.05 mmol, 1.00 equiv) in a 250-mL round-bottom flask, then stirred for 3 hr at reflux in an oil bath. The resulting mixture was concentrated under vacuum, diluted with 100 mL of EtOAc, and the pH of the solution adjusted to 7-8 with aqueous $NaHCO_3$ (saturated). The solution was then extracted with 6×50 mL of ethyl acetate, the organic layers combined and dried over anhydrous sodium sulfate, and concentrated under vacuum, affording 12.42 g (crude) of methyl 4-fluoro-3-nitrobenzoate as a white solid.

Step 2

Synthesis of methyl 4-(2-methoxy-2-oxo-1-phenylethylamino)-3-nitrobenzoate

A solution of methyl 2-amino-2-phenylacetate hydrochloride (2.5 g, 12.38 mmol, 1.00 equiv) in DMF (30 mL), methyl 4-fluoro-3-nitrobenzoate (5 g, 25.13 mmol, 2.00 equiv), and DIEA (5 g, 38.76 mmol, 3.13 equiv) was reacted overnight at 30° C. in a 100-mL round-bottom flask. The reaction was then quenched by the addition of 200 mL of water, and the solids were collected by filtration. Purification via silica gel column (petroleum ether/EtOAc (50:1)) yielded 3.82 g (90%) of methyl 4-(2-methoxy-2-oxo-1-phenylethylamino)-3-nitrobenzoate as a yellow solid. LC-MS (ES, m/z): 345 $[M+H]^+$.

Step 3

Synthesis of methyl 3-oxo-2-phenyl-1,2,3,4-tetrahydroquinoxaline-6-carboxylate

Iron (34.89 g, 623.04 mmol, 5.00 equiv) was added portionwise to a stirred solution of methyl 4-(2-methoxy-2-oxo-1-phenylethylamino)-3-nitrobenzoate (42.87 g, 124.62 mmol, 1.00 equiv) and aqueous $NH_4Cl$ (32.1 g, 600.00 mmol, 5.00 equiv, 80 mL) in methanol (300 mL). The resulting solution was heated under reflux for 5 h. Upon cooling, the solids were filtered out. The resulting filtrate was concentrated under vacuum, affording 19.81 g (56%) of methyl 3-oxo-2-phenyl-1,2,3,4-tetrahydroquinoxaline-6-carboxylate as a yellow solid. LC-MS (ES, m/z): 283 $[M+H]^+$.

Step 4

Synthesis of methyl 3-oxo-2-phenyl-3,4-dihydroquinoxaline-6-carboxylate

DDQ (21.25 g, 93.6 mmol, 2.62 equiv) was added to a stirred solution of methyl 3-oxo-2-phenyl-1,2,3,4-tetrahydroquinoxaline-6-carboxylate (10.07 g, 35.7 mmol, 1.00 equiv) in dioxane (750 mL) and allowed to react, with stifling, overnight at room temperature. The solids were collected by filtration. The filter cake was washed with 2×500 mL of aqueous $K_2CO_3$ (saturated). This resulted in 7.29 g (crude) of methyl 3-oxo-2-phenyl-3,4-dihydroquinoxaline-6-carboxylate as an off-white solid. LC-MS (ES, m/z): 281 $[M+H]^+$.

Step 5

Synthesis of methyl 3-bromo-2-phenylquinoxaline-6-carboxylate

A solution of methyl 3-oxo-2-phenyl-3,4-dihydroquinoxaline-6-carboxylate (2.1 g, 7.50 mmol, 1.00 equiv) and $POBr_3$ (21.5 g, 74.91 mmol, 10.00 equiv) in $CH_3CN$ (120 mL) in a 1000-mL round-bottom flask was heated under reflux overnight in an oil bath. The resulting mixture was concentrated under vacuum; the pH value was adjusted to 7-8 with aqueous sodium bicarbonate (saturated), and the solution extracted with 4×100 mL of dichloromethane. The organic layers were combined, dried over anhydrous sodium sulfate and concentrated under vacuum, giving 2 g (78%) of methyl 3-bromo-2-phenylquinoxaline-6-carboxylate as a white solid. LC-MS (ES, m/z): 343 $[M+H]^+$. $^1$H-NMR (300 MHz, DMSO-$d_6$) 8.620-8.615 (d, J=1.5 Hz, 1H), 8.38-8.35 (q, J=3.3 Hz, 1H), 8.28-8.25 (d, J=8.7 Hz, 1H), 7.85-7.82 (q, J=6 Hz, 2H), 7.60-7.58 (t, J=2.4 Hz, 3H), 3.99 (s, 3H).

Scheme II

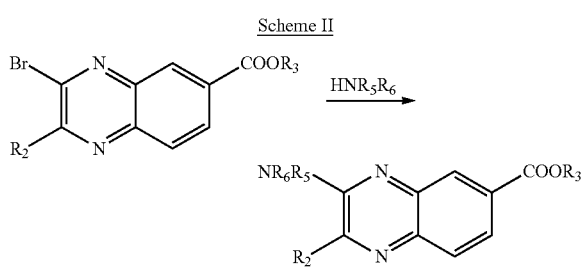

wherein $R_2$ is chosen from alkyl, cycloalkyl, heterocycloalkyl, aryl, heteroaryl, and amino any of which may be optionally substituted; and $R_3$ is chosen from hydrogen and optionally substituted alkyl.

Scheme III

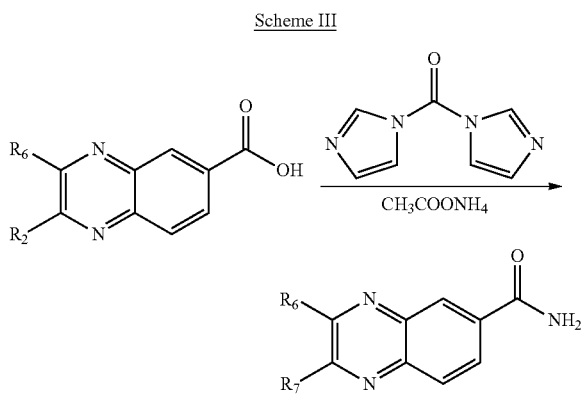

Wherein $R_6$ and $R_7$ are independently chosen from alkyl, cycloalkyl, heterocycloalkyl, aryl, heteroaryl, and amino any of which may be optionally substituted.

The invention is further illustrated by the following examples, which can be made by the methods described herein or by one skilled in the art without undue experimentation, or can be purchased from commercial sources. Throughout the experimental protocols, the following abbreviations may be used. The list below is provided for convenience and is not intended to be inclusive.

| Abbreviation/Acronym | Meaning |
|---|---|
| Ar | Aryl |
| $Pd_2(dba)_3$ | Tris(dibenzylideneacetone)dipalladium(0) |
| BINAP | 2,2'-bis(diphenylphosphino)-1,1'-binaphthyl |
| NaOt-Bu | Sodium t-Butoxide |
| PE | Petroleum Ether |
| EA | Ethyl Acetate |
| DCM | Dichloromethane |
| TFA | Trifluoroacetic Acid |
| AcOH | Acetic Acid |
| DMF | N,N-Dimethylformamide |
| DIEA | N,N-Diisopropylethylamine |
| MeOH | Methanol |
| THF | Tetrahydrofuran |
| BOC | N-t-butoxycarbonyl |
| Tol | Toluene |
| DMSO | Dimethyl Sulfoxide |
| PCy3 | Tricyclohexylphosphine |
| TLC | Thin Layer Chromatography |
| X-Phos | 2-Dicyclohexylphosphino-2',4',6'-triisopropylbiphenyl |
| DDQ | 2,3-dichloro-5,6-dicyanobenzoquinone |

Example 1

2-(4-Fluorophenyl)-3-(isopropyl(methyl)amino)quinoxaline-6-carboxamide

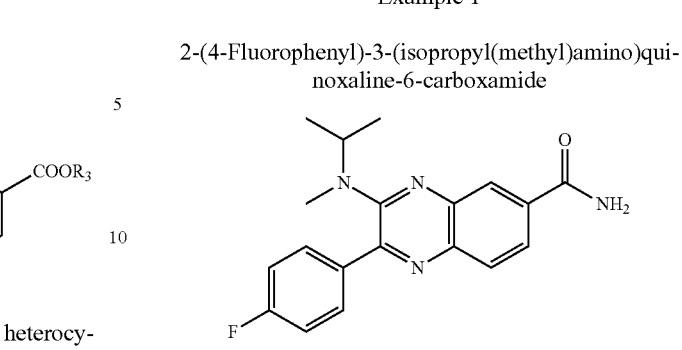

To a solution of 2-(4-fluorophenyl)-3-(isopropyl(methyl)amino)quinoxaline-6-carboxylic acid (100.0 mg, 0.30 mmol) in N,N-dimethylformamide (8 mL) was added di(1H-imidazol-1-yl)methanone (57.2 mg, 0.36 mmol) at 50° C. The solution was stirred for 30 min at 50° C. and then $CH_3COONH_4$ (45.2 mg, 0.58 mmol) was added. The resulting solution was stirred for another 4 h at 50° C. in an oil bath and quenched by the addition of water (50 mL), extracted with ethyl acetate (3×30 mL), dried over anhydrous sodium sulfate and concentrated in vacuo. The residue was purified by silica gel column chromatography (10% methanol in dichloromethane) to afford. 2-(4-fluorophenyl)-3-(isopropyl(methyl)amino)quinoxaline-6-carboxamide as a yellow solid (35 mg, 35%).

LC/MS (ES, m/z): [M+H]$^+$ 339.1

$^1$H-NMR (300 MHz, CDCl$_3$) δ 8.34 (s, 1H), 7.88-8.03 (m, 4H), 7.18-7.24 (t, J=8.7 Hz, 2H), 6.27-6.36 (m, 1H), 5.66-5.71 (m, 1H), 4.28 (s, 1H), 2.80 (s, 3H), 1.12 (d, J=6.6 Hz, 6H)

Example 2

Methyl 2-(4-fluorophenyl)-3-[(3S)-3-methylmorpholin-4-yl]quinoxaline-6-carboxylate

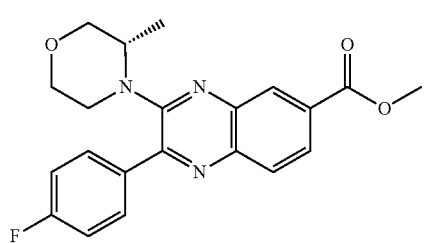 [SMILES: COC(=O)c1ccc2nc(-c3ccc(F)cc3)c(N3CCOC[C@@H]3C)nc2c1]

Step 1. (S)-Methyl 3-(3-methylmorpholino)-2-oxo-1,2-dihydroquinoxaline-6-carboxylate

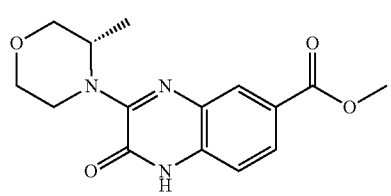 [SMILES: COC(=O)c1ccc2[nH]c(=O)c(N3CCOC[C@@H]3C)nc2c1]

To a solution of (3S)-3-methylmorpholine (200 mg, 1.98 mmol) in DMSO (10 mL) was added methyl 3-chloro-2- hydroxyquinoxaline-6-carboxylate (700 mg, 2.93 mmol), DIEA (510 mg, 3.95 mmol). The resulting solution was stirred overnight at 70° C. and then dissolved in water (100 mL), extracted with dichloromethane (4×30 mL), dried over anhydrous magnesium sulfate and concentrated in vacuo. The residue was purified by a silica gel column chromatography (5%-50% ethyl acetate in petroleum ether) to afford methyl 2-hydroxy-3-[(3S)-3-methylmorpholin-4-yl]quinoxaline-6-carboxylate as a light yellow solid (210.0 mg).

LC/MS (ES, m/z): [M+H]+ 304.0

$^1$H-NMR (300 MHz, CDCl$_3$), δ 9.34 (s, 1H), 8.22 (d, J=1.5 Hz, 1H), 7.87-7.90 (m, 1H), 7.04 (d, J=8.1 Hz, 1H), 3.95-4.03 (m, 4H), 3.67-3.87 (m, 3H), 3.50-3.56 (m, 1H), 1.43 (d, J=6.6 Hz, 3H)

Step 2. Methyl 3-[(3S)-3-methylmorpholin-4-yl]-2-[(trifluoromethane)sulfonyloxy]quinoxaline-6-carboxylate

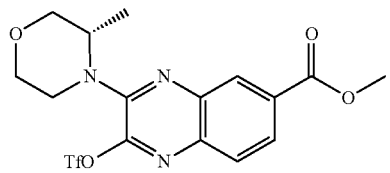 [SMILES: COC(=O)c1ccc2nc(OS(=O)(=O)C(F)(F)F)c(N3CCOC[C@@H]3C)nc2c1]

To a solution of methyl 3-[(3S)-3-methylmorpholin-4-yl]-2-oxo-1,2-dihydroquinoxaline-6-carboxylate (210 mg, 0.69 mmol) in dichloromethane (50 mL) was added pyridine (220 mg, 2.78 mmol), followed by Tf$_2$O (390 mg, 1.38 mmol), and the resulting mixture was stirred overnight at room temperature. The reaction was then quenched by the addition of ice-water (100 mL) and extracted with dichloromethane (2×20 mL), the organic layers were combined and dried over anhydrous magnesium sulfate and concentrated in vacuo to afford methyl 3-[(3S)-3-methylmorpholin-4-yl]-2-[(trifluoromethane)sulfonyloxy]quinoxaline-6-carboxylate as red oil (300 mg, crude).

Step 3. Methyl 2-(4-fluorophenyl)-3-[(3S)-3-methylmorpholin-4-yl]quinoxaline-6-carboxylate

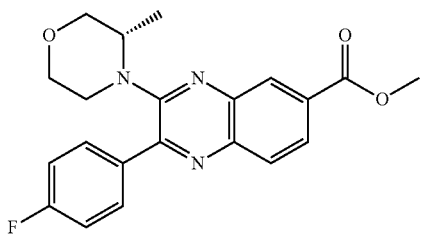

To a solution of methyl 3-[(3S)-3-methylmorpholin-4-yl]-2-[(trifluoromethane)sulfonyloxy]quinoxaline-6-carboxylate (300 mg, crude) in dioxane (10 mL) was added Pd(PPh$_3$)$_4$ (40 mg, 0.03 mmol), (4-fluorophenyl)boronic acid (200 mg, 1.43 mmol), K$_3$PO$_4$ (292 mg, 1.38 mmol) and water (1 mL). The resulting solution was stirred for 1 h at 90° C. under an inert atmosphere of nitrogen, and then concentrated in vacuo to give a residue, which was purified by a silica gel column chromatograpy (2%-4% ethyl acetate in petroleum ether) to afford methyl 2-(4-fluorophenyl)-3-[(3S)-3-methylmorpholin-4-yl]quinoxaline-6-carboxylate as a yellow solid (140 mg).

LC/MS (ES, m/z): [M+H]+ 382.0

$^1$H-NMR (300 MHz, CDCl$_3$), δ 8.56 (d, J=1.8 Hz, 1H), 8.00-8.16 (m, 4H), 7.20-7.26 (m, 2H), 4.01 (s, 3H), 3.84-3.89 (m, 2H), 3.64-3.76 (m, 2H), 3.31-3.56 (m, 3H), 1.17 (d, J=6.6 Hz, 3H)

Example 3

Methyl 2-(benzofuran-2-yl)-3-(cyclopropyl(methyl)amino)quinoxaline-6-carboxylate

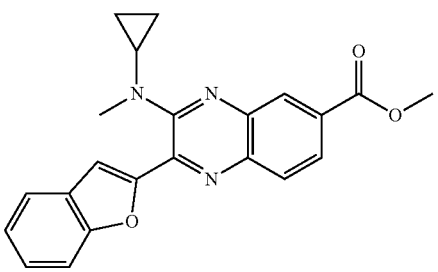 [SMILES: COC(=O)c1ccc2nc(-c3cc4ccccc4o3)c(N(C)C3CC3)nc2c1]

Step 1. Methyl 3-(cyclopropyl(methyl)amino)-2-oxo-1,2-dihydroquinoxaline-6-carboxylate

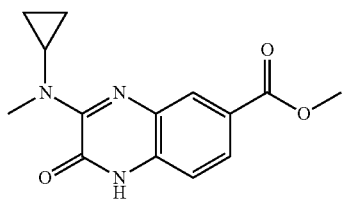

To a solution of methyl 3-chloro-2-oxo-1,2-dihydroquinoxaline-6-carboxylate (1.0 g, 4.20 mmol) in DMSO (6 mL) was added DIEA (1.35 g, 10.47 mmol), N-methylcyclopropanamine hydrochloride (490 mg, 4.58 mmol). The solution was stirred 10 mins at room temperature and 2 h at 75° C. Then the reaction was quenched by the addition of water (100 mL) and the solids were collected by filtration to afford methyl 3-(cyclopropyl(methyl)amino)-2-oxo-1,2-dihydroquinoxaline-6-carboxylate as a yellow solid (405 mg, 35%).

LC/MS (ES, m/z): [M+H]$^+$ 274.0

$^1$H-NMR (300 MHz, DMSO) δ 12.25 (s, 1H), 7.96 (d, J=1.8 Hz, 1H), 7.72-7.75 (m, 1H), 7.20 (d, J=8.4 Hz, 1H), 3.85 (d, J=5.4 Hz, 3H), 3.23 (s, 3H), 3.03-3.11 (m, 1H), 0.76-0.82 (m, 2H), 0.57-0.63 (m, 2H)

Step 2. Methyl 3-(cyclopropyl(methyl)amino)-2-(trifluoromethylsulfonyloxy)quinoxaline-6-carboxylate

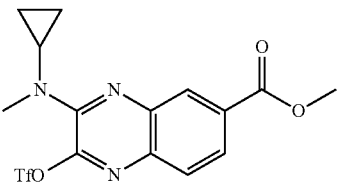

To a solution of methyl 3-(cyclopropyl(methyl)amino)-2-oxo-1,2-dihydroquinoxaline-6-carboxylate (126.0 mg, 0.46 mmol) in dichloromethane (34 mL) was added pyridine (145.0 mg, 1.84 mmol) and then Tf$_2$O (259 mg, 0.92 mmol) was added dropwise with stirring at 0° C. The resulting solution was stirred for 3 h at room temperature and then quenched by the addition of ice-water (50 mL), extracted with dichloromethane (2×20 mL), dried over anhydrous sodium sulfate and concentrated under vacuum to afford methyl 3-(cyclopropyl(methyl)amino)-2-(trifluoromethylsulfonyloxy)quinoxaline-6-carboxylate as red oil (180 mg, crude).

Step 3. Methyl 2-(benzofuran-2-yl)-3-(cyclopropyl(methyl)amino)quinoxaline-6-carboxylate

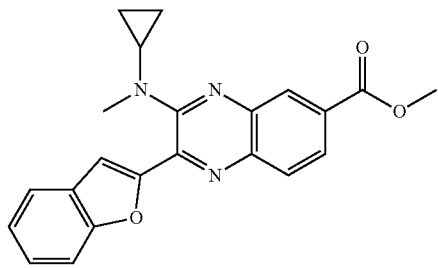 [SMILES: COC(=O)c1ccc2nc(-c3cc4ccccc4o3)c(N(C)C3CC3)nc2c1]

To a solution of methyl 3-(cyclopropyl(methyl)amino)-2-(trifluoromethylsulfonyloxy)quinoxaline-6-carboxylate (180.0 mg, crude) in dioxane (6 mL) was added benzofuran-2-ylboronic acid (149.0 mg, 0.92 mmol), K$_3$PO4 (195.0 mg, 0.92 mmol), Pd(PPh$_3$)$_4$ (30.0 mg, 0.03 mmol) and water (3 drops). The resulting solution was stirred for 1 h at 90° C. and then concentrated under vacuum to give a residue, which was purified by a silica gel column (5%-20% ethyl acetate in petroleum ether) to afford methyl 2-(benzofuran-2-yl)-3-(cyclopropyl(methyl)amino)quinoxaline-6-carboxylate as a yellow solid (95.0 mg, 39% 2 steps).

LC/MS (ES, m/z): [M+H]$^+$ 374.0

$^1$H-NMR (300 MHz, DMSO) δ 8.68 (s, 1H), 8.08-8.16 (m, 2H), 7.63-7.72 (m, 2H), 7.50 (d, J=0.6 Hz, 1H), 7.42-7.45 (m, 1H), 7.28-7.40 (m, 1H), 4.01 (s, 3H), 3.21 (s, 3H), 2.96-3.01 (m, 1H), 0.53-0.74 (m, 4H).

Example 4

Methyl 2-(5-fluorobenzofuran-2-yl)-3-(isopropylmethyl)amino)quinoxaline-6-carboxylate

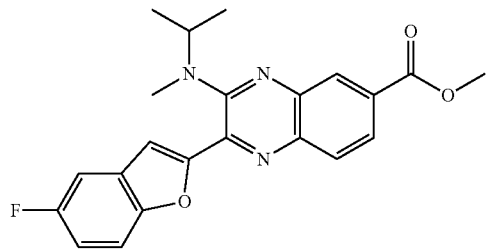 [SMILES: COC(=O)c1ccc2nc(-c3cc4cc(F)ccc4o3)c(N(C)C(C)C)nc2c1]

Step 1. 1-(Diethoxymethoxy)-4-fluorobenzene

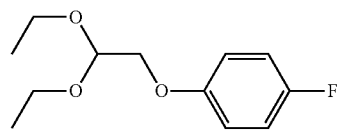 [SMILES: CCOC(COc1ccc(F)cc1)OCC]

To a suspension of sodium hydride (11.24 g, 281.00 mmol) in anhydrous N,N-dimethylformamide (500 mL) was added 4-fluorophenol (26.21 g, 233.96 mmol) at 0° C. After hydrogen evolution had ceased, bromo-acetaldehyde diethyl acetal (55 g, 280.60 mmol) was added. The reaction was heated at 120° C. overnight. The mixture was poured into ice-water, extracted with ethyl acetate (3×150 mL), washed with 1N sodium hydroxide (3×100 mL), and brine (3×100 mL). The organic layer was dried over anhydrous sodium sulfate and filtered. The solvent was removed under vacuum to give the residue, which was purified by a silica gel column (1% ethyl acetate in petroleum ether) to afford 1-(diethoxymethoxy)-4-fluorobenzene as oil (45 g, 84%).

$^1$H-NMR (300 MHz, CDCl$_3$): δ 6.84-7.01 (m, 4H), 4.81-4.85 (t, J=5.1 Hz, 1H), 3.99 (d, J=5.1 Hz, 2H), 3.69-3.83 (m, 2H), 3.59-3.67 (m, 2H), 1.24-1.31 (m, 6H)

Step 2. 5-Fluorobenzofuran

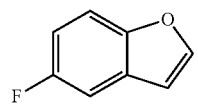

To a mixture of benzene (200 mL) containing polyphosphoric acid (80 g, 236.69 mmol) was added 2-(4-fluorophenoxy)-acetaldehyde diethyl acetal (45 g, 197.37 mmol). The mixture was stirred vigorously while being heated to reflux for 2.5 hours. The reaction mixture was cooled to room temperature and decanted from the polyphosphoric acid. The solvent was removed under vacuum to give the residue, which was purified by a silica gel column (1% ethyl acetate in petroleum ether) to afford 5-fluorobenzofuran as colorless oil (14.0 g, crude).

¹H-NMR (300 MHz, CDCl₃): δ 7.67 (d, J=2.1 Hz, 1H), 7.44-7.48 (m, 1H), 7.27-7.30 (m, 1H), 7.01-7.08 (m, 1H), 6.76-6.77 (m, 1H)

Step 3. 5-Fluorobenzofuran-2-ylboronic acid

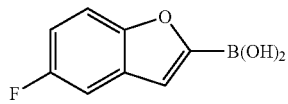 [SMILES: OB(O)c1cc2cc(F)ccc2o1]

To a solution of 5-fluorobenzofuran (10 g, 73.53 mmol) in dry tetrahydrofuran (250 mL) was added tetramethylethylenediamine (10.2 g, 87.93 mmol). The solution was kept below −60° C. under nitrogen, while BuLi (93.75 mmol, 2.5M solution in hexane) was added dropwise. It was warmed to −10° C. during 45 min and stirred at this temperature for another 30 min. The mixture was cooled again below −60° C. followed by dropwise addition of triisopropyl borate (41.4 g, 220.21 mmol). After warming to room temperature the mixture was quenched with hydrochloric acid (70 mL, 2N) and stirred for 1 h. The alkaline aqueous layer was brought to pH 5 and extracted with ethyl acetate (3×80 mL). All organic layers were combined, dried over sodium sulfate, and concentrated in vacuo to give 5-fluorobenzofuran-2-ylboronic acid (3.5 g, 26%) which was used for the next step without further purification.

¹H-NMR (300 MHz, CDCl₃): δ 8.63 (s, 2H), 7.58-7.62 (m, 1H), 7.44-7.49 (m, 2H), 7.15-7.22 (m, 1H)

Step 4. Methyl 2-(5-fluorobenzofuran-2-yl)-3-(isopropyl(methyl)amino)quinoxaline-6-carboxylate

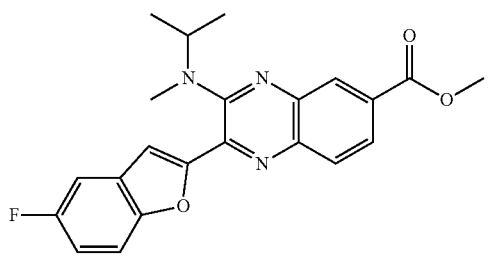 [SMILES: COC(=O)c1ccc2nc(-c3cc4cc(F)ccc4o3)c(N(C)C(C)C)nc2c1]

To a solution of 5-fluorobenzofuran-2-ylboronic acid (258.0 mg, 1.43 mmol) in dioxane (5.5 mL) was added ethyl 2-chloro-3-(isopropyl(methyl)amino)quinoxaline-6-carboxylate (140.0 mg, 0.48 mmol), K₃PO₄ (302.0 mg, 1.43 mmol) and Pd(PPh₃)₄ (27.5 mg, 0.02 mmol) and water (3 drops) with stirring for 1 h at 90° C. in an oil bath maintained under an inert atmosphere of nitrogen. The reaction mixture was concentrated under vacuum to give a residue, which was purified by a silica gel column (1% ethyl acetate in petroleum ether) to afford methyl 2-(5-fluorobenzofuran-2-yl)-3-(isopropyl(methyl)amino)quinoxaline-6-carboxylate as a light yellow solid (160.0 mg, 81%).

LC/MS (ES, m/z): [M+H]⁺ 394.0

¹H-NMR (300 MHz, CDCl₃): δ 8.61 (d, J=1.5 Hz, 1H), 8.05-8.14 (m, 2H), 7.57-7.62 (m, 2H), 7.34-7.37 (m, 1H), 7.11-7.18 (m, 1H), 4.29-4.38 (m, 1H), 4.01 (s, 3H), 2.94 (s, 3H), 1.21 (d, J=6.6 Hz, 6H)

Example 5

Methyl 2-(4-fluorophenyl)-3-(isopropylmethyl)amino)quinoxaline-6-carboxylate

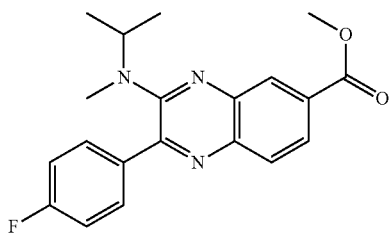 [SMILES: COC(=O)c1ccc2nc(-c3ccc(F)cc3)c(N(C)C(C)C)nc2c1]

Into a 10-mL sealed tube, was placed methyl 2-chloro-3-(isopropyl(methyl)amino)quinoxaline-6-carboxylate (40 mg, 0.14 mmol, 1.00 equiv), 4-fluorophenylboronic acid (57.4 mg, 0.41 mmol, 3.00 equiv), Pd(PPh₃)₄ (31.4 mg, 0.03 mmol, 0.20 equiv), K₃PO₄ (116 mg, 0.55 mmol, 4.00 equiv), 1,4-dioxane (3 mL). The resulting solution was stirred for overnight at 110° C. in an oil bath. The solids were filtered out. The filtrate was concentrated under vacuum. The residue was purified by prep-TLC with ethyl acetate/petroleum ether (1:8). This resulted in 42 mg (87%) of methyl 2-(4-fluorophenyl)-3-(isopropyl(methyl)amino)quinoxaline-6-carboxylate as a yellow solid.

LC-MS: (ES, m/z): 354 [M+H]⁺

¹H-NMR (300 MHz, CDCl₃, ppm): δ 8.600-8.595 (d, J=1.5 Hz, 1H), 8.094-7.903 (m, 4H), 7.281-7.180 (m, 2H), 4.295-4.251 (m, 1H), 4.006 (s, 3H), 2.779 (s, 3H), 1.127-1.105 (d, J=6.6 Hz, 6H)

Example 6

(S)-Butyl 2-(4-fluorophenyl)-3-(2-methylpyrrolidin-1-yl)quinoxaline-6-carboxylate

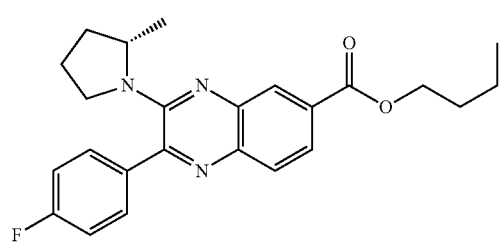 [SMILES: CCCCOC(=O)c1ccc2nc(-c3ccc(F)cc3)c(N3CCC[C@@H]3C)nc2c1]

Step 1. Methyl 4-(1-(4-fluorophenyl)-2-methoxy-2-oxoethylamino)-3-nitrobenzoate

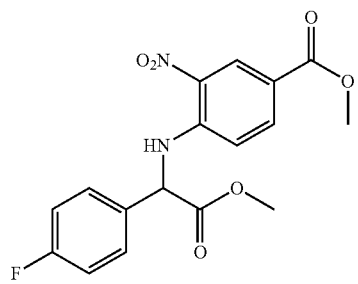 [SMILES: COC(=O)c1ccc(NC(C(=O)OC)c2ccc(F)cc2)c([N+](=O)[O-])c1]

Into a 250-mL round-bottom flask, was placed methyl 4-fluoro-3-nitrobenzoate (15.4 g, 77.78 mmol, 1.00 equiv), N,N-dimethylformamide (100 mL), methyl 2-amino-2-(4-fluorophenyl)acetate hydrochloride (20.4 g, 93.15 mmol, 1.20 equiv), and DIEA (50.2 g, 389.15 mmol, 5.00 equiv). The reaction was stirred overnight at 35° C. in an oil bath. The resulting solution was diluted with 500 ml of H$_2$O and the resulting solids were collected by filtration. This resulted in 15 g (53%) of methyl 4-(1-(4-fluorophenyl)-2-methoxy-2-oxoethylamino)-3-nitrobenzoate as a yellow solid.

Step 2. Methyl 2-(4-fluorophenyl)-3-oxo-1,2,3,4-tetrahydroquinoxaline-6-carboxylate

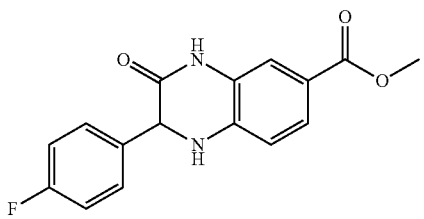 [SMILES: COC(=O)c1ccc2c(c1)NC(=O)C(c1ccc(F)cc1)N2]

Into a 100-mL round-bottom flask, was placed methyl 4-(1-(4-fluorophenyl)-2-methoxy-2-oxoethylamino)-3-nitrobenzoate (3.5 g, 9.67 mmol, 1.00 equiv), methanol (50 mL), and palladium on carbon (10%) (500 mg). Hydrogen gas was introduced to the reaction, and it was stirred overnight at 30° C. in an oil bath. Then the solids were filtered off and the filtrate was concentrated in vacuo. This resulted in 2.6 g (90%) of methyl 2-(4-fluorophenyl)-3-oxo-1,2,3,4-tetrahydroquinoxaline-6-carboxylate as a light yellow solid.

LC-MS: (ES, m/z): 301 [M+H]$^+$

Step 3. Methyl 3-chloro-2-(4-fluorophenyl)quinoxaline-6-carboxylate

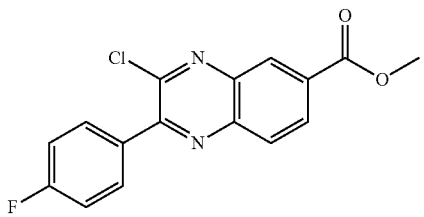 [SMILES: COC(=O)c1ccc2nc(-c3ccc(F)cc3)c(Cl)nc2c1]

Into a 100-mL round-bottom flask, was placed methyl 2-(4-fluorophenyl)-3-oxo-1,2,3,4-tetrahydroquinoxaline-6-carboxylate (1.2 g, 4.00 mmol, 1.00 equiv), POCl$_3$ (12.2 g, 80.26 mmol, 20.00 equiv), N,N-dimethylbenzenamine (4.9 g, 40.50 mmol, 10.00 equiv). The resulting solution was stirred for overnight at 110° C. in an oil bath. The resulting mixture was concentrated under vacuum and diluted with 50 mL of water. The pH of the aqueous solution was adjusted to 7 with sodium bicarbonate (4M). The resulting mixture was concentrated under vacuum and purified by silica gel chromatography with ethyl acetate/petroleum ether (1:40). This resulted in 0.5 g (40%) of methyl 3-chloro-2-(4-fluorophenyl)quinoxaline-6-carboxylate as a white solid.

LC-MS: (ES, m/z): 317 [M+H]$^+$ $^1$H-NMR (300 MHz, CDCl$_3$, ppm): δ 8.785-8.779 (d, J=1.8 Hz, 1H), 8.433-8.398 (m, 1H), 8.214-8.185 (d, J=8.7 Hz, 1H), 7.973-7.926 (m, 2H), 7.265 (d, 1H), 4.052 (s, 3H)

Step 4. (S)-Butyl 2-(4-fluorophenyl)-3-(2-methylpyrrolidin-1-yl)quinoxaline-6-carboxylate

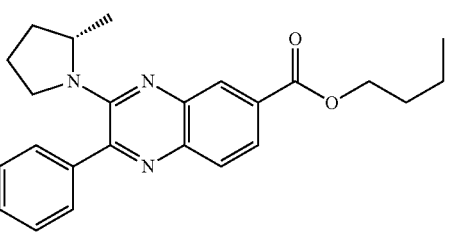

Into a 10-mL sealed tube, was placed methyl 3-chloro-2-(4-fluorophenyl)quinoxaline-6-carboxylate (150 mg, 0.47 mmol, 1.00 equiv), (S)-2-methylpyrrolidine (403 mg, 4.74 mmol, 9.99 equiv), butan-1-ol (2 mL). The resulting solution was stirred overnight at 110° C. in an oil bath. The resulting mixture was concentrated under vacuum. This resulted in 150 mg (crude) of (S)-butyl 2-(4-fluorophenyl)-3-(2-methylpyrrolidin-1-yl)quinoxaline-6-carboxylate as a yellow solid.

LC-MS: (ES, m/z): 408 [M+H]

Example 7

Methyl 2-(benzofuran-2-yl)-3-(isopropyl(methyl)amino)quinoxaline-6-carboxylate

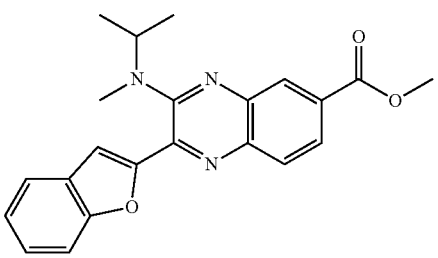 [SMILES: COC(=O)c1ccc2nc(-c3cc4ccccc4o3)c(N(C)C(C)C)nc2c1]

Into a 10-mL sealed tube, was placed methyl 2-chloro-3-(isopropyl(methyl)amino)quinoxaline-6-carboxylate (200 mg, 0.68 mmol, 1.00 equiv), benzofuran-2-ylboronic acid (220 mg, 1.36 mmol, 1.99 equiv), Pd(PPh$_3$)$_4$ (157 mg, 0.14 mmol, 0.20 equiv), K$_3$PO$_4$ (577 mg, 2.73 mmol, 4.01 equiv), and 1,4-dioxane (4 mL). The resulting solution was stirred for overnight at 100° C. in an oil bath. The resulting mixture was concentrated under vacuum. The residue was applied onto a silica gel column with ethyl acetate/petroleum ether (1:40). This resulted in 160 mg (63%) of methyl 2-(benzofuran-2-yl)-3-(isopropyl(methyl)amino)quinoxaline-6-carboxylate as a yellow solid.

LC-MS: (ES, m/z): 376 [M+H]$^+$

Example 8

Methyl 3-(1,2,3,4-tetrahydroquinolin-1(2H)-yl)-2-(4-fluorophenyl) quinoxaline-6-carboxylate

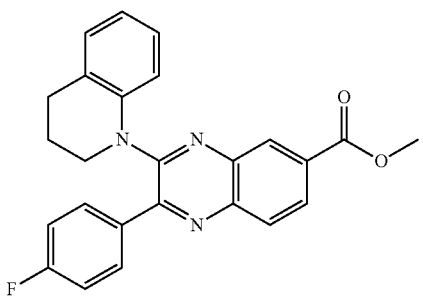 [SMILES: COC(=O)c1ccc2nc(-c3ccc(F)cc3)c(N3CCCc4ccccc43)nc2c1]

4-Fluorophenylboronic acid (188.8 mg, 1.35 mmol), $K_3PO_4$ (284.8 mg, 1.35 mmol) and $Pd(PPh_3)_4$ (25.9 mg, 0.02 mmol) were added to a solution of methyl 3-(1,2,3,4-tetrahydroquinolin-1(2H)-yl)-2-(trifluoromethylsulfonyloxy) quinoxaline-6-carboxylate (210 mg, 0.45 mmol) in dioxane (5.0 mL) and three drops of water. The reaction was stirred for 1 h at 95° C. while under an inert atmosphere of nitrogen in an oil bath. The reaction mixture was concentrated in vacuo and purified by flash column chromatography with 2% ethyl acetate in petroleum to afford methyl 3-(1,2,3,4-tetrahydroquinolin-1(2H)-yl)-2-(4-fluorophenyl)quinoxaline-6-carboxylate as a red solid (70 mg, 36%).

Calculated for $C_{25}H_{20}FN_3O_2$: 413.15. (ES, m/z): $[M+H]^+$ 414.0.

$^1$H-NMR (300 MHz, $CDCl_3$): δ 8.74 (s, 1H), 8.21-8.24 (dd, $J_1=J_2=1.5$ Hz, 1H), 8.12 (d, J=8.4 Hz, 1H), 7.72-7.76 (m, 2H), 6.93-7.02 (m, 3H), 6.79-6.83 (m, 2H), 6.62 (s, 1H), 4.02 (s, 3H), 3.93-3.97 (t, J=6.0 Hz, 2H), 2.79-2.84 (t, J=6.3 Hz, 2H), 2.09-2.14 (t, J=6.3 Hz, 2H)

Example 9

Methyl 2-(5-chloro-1-benzofuran-2-yl)-3-(6-methoxy-1,2,3,4-tetrahydroquinolin-1-yl)quinoxaline-6-carboxylate

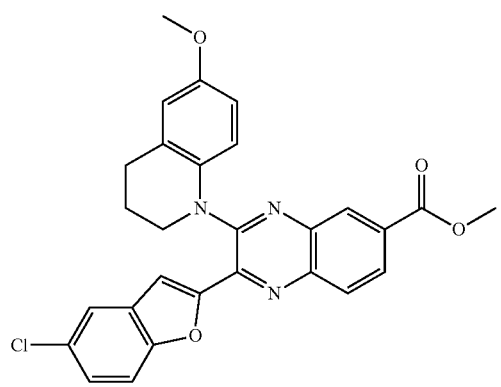 [SMILES: COC(=O)c1ccc2nc(-c3cc4cc(Cl)ccc4o3)c(N3CCCc4cc(OC)ccc43)nc2c1]

To a solution of methyl 3-(6-methoxy-1,2,3,4-tetrahydroquinolin-1-yl)-2-[(trifluoromethane)sulfonyloxy]quinoxaline-6-carboxylate (From Ex. 5, step 2, 130 mg, crude) in dioxane (5.0 mL) and water (three drops) was added (5-chloro-1-benzofuran-2-yl)boronic acid (103 mg, 0.52 mmol, $K_3PO_4$ (165.8 mg, 0.78 mmol) and $Pd(PPh_3)_4$ (15.2 mg, 0.01 mmol) with stifling for 1 h at 90° C. maintained with an inert atmosphere of nitrogen in an oil bath. The reaction mixture was concentrated under vacuum to give the residue, which was purified by a silica gel column with 2% ethyl acetate in petroleum ether to afford methyl 2-(5-chloro-1-benzofuran-2-yl)-3-(6-methoxy-1,2,3,4-tetrahydroquinolin-1-yl)quinoxaline-6-carboxylate as a red solid (40 mg).

(ES, m/z): $[M+H]^+$ 500.0

$^1$H-NMR (300 MHz, $CDCl_3$) δ 8.61 (d, J=1.5 Hz, 1H), 8.13-8.22 (m, 2H), 7.51 (d, J=2.1 Hz, 1H), 7.25-7.40 (m, 3H), 6.65 (d, J=2.7 Hz, 1H), 6.56 (d, J=8.7 Hz, 1H), 6.32-6.36 (m, 1H), 4.01 (s, 3H), 3.96-3.99 (t, J=6.3 Hz, 2H), 2.93-2.98 (t, J=6.6 Hz, 2H), 2.13-2.21 (m, 2H)

Example 10

Methyl 3-[6-(dimethylsulfamoyl)-1,2,3,4-tetrahydroquinolin-1-yl]-2-(4-fluorophenyl)quinoxaline-6-carboxylate

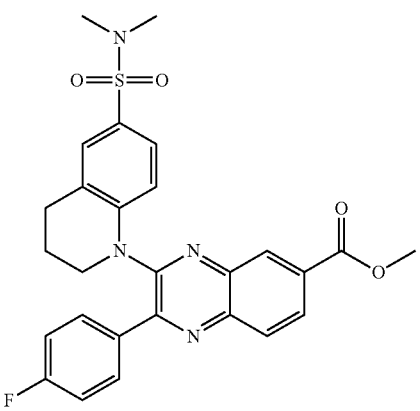 [SMILES: COC(=O)c1ccc2nc(-c3ccc(F)cc3)c(N3CCCc4cc(S(=O)(=O)N(C)C)ccc43)nc2c1]

Step 1. Methyl 3-[6-(chlorosulfonyl)-1,2,3,4-tetrahydroquinolin-1-yl]-2-(4-fluorophenyl)quinoxaline-6-carboxylate

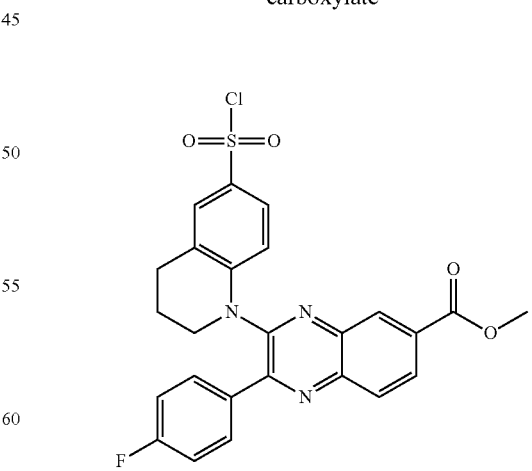

To a solution of methyl 2-(4-fluorophenyl)-3-(1,2,3,4-tetrahydroquinolin-1-yl)quinoxaline-6-carboxylate (300 mg, 0.73 mmol) in chloroform (50 mL) was added sulfuric acid (213.6 mg, 2.18 mmol) and thionyl chloride (514 mg, 4.36 mmol) dropwise with stirring at 85° C. for 3 h in an oil bath. The reaction was then quenched by the addition of ice-water, extracted with dichloromethane (3×80 mL). The organic layers combined and dried over magnesium sulfate, concentrated under vacuum to give the residue, which was applied onto a silica gel column with 2% ethyl acetate in petroleum to afford methyl 3-[6-(chlorosulfonyl)-1,2,3,4-tetrahydroquinolin-1-yl]-2-(4-fluorophenyl)quinoxaline-6-carboxylate as a yellow solid (260 mg, 70%).

(ES, m/z): [M+H]$^+$ 512.0

$^1$H-NMR (300 MHz, CDCl$_3$): δ 8.70 (d, J=1.5 Hz, 1H), 8.35-8.38 (m, 1H), 8.18 (d, J=4.2 Hz, 1H), 7.77-7.82 (m, 2H), 7.71 (d, J=2.1 Hz, 1H), 7.48-7.52 (m, 1H), 7.11-7.16 (m, 2H), 6.67 (d, J=9.0 Hz, 1H), 4.04 (s, 3H), 3.76-3.80 (t, J=6.0 Hz, 2H), 2.92-2.96 (t, J=6.3 Hz, 2H), 2.07-2.12 (m, 2H)

Step 2. Methyl 3-[6-(dimethylsulfamoyl)-1,2,3,4-tetrahydroquinolin-1-yl]-2-(4-fluorophenyl)quinoxaline-6-carboxylate

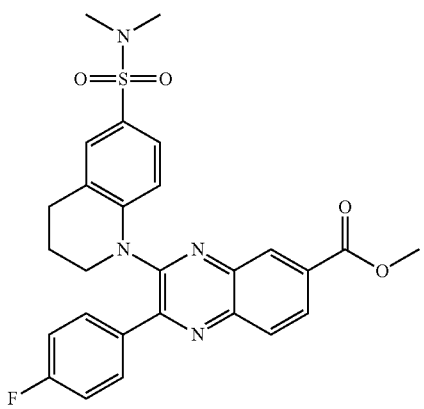 [SMILES: COC(=O)c1ccc2nc(-c3ccc(F)cc3)c(N3CCCc4cc(S(=O)(=O)N(C)C)ccc43)nc2c1]

To a solution of dimethylamine hydrochloride (49.66 mg, 0.61 mmol) in dichloromethane (50 mL) was added and triethylamine (102 mg, 1.01 mmol) and stirred for 10 min. Then methyl 3-[6-(chlorosulfonyl)-1,2,3,4-tetrahydroquinolin-1-yl]-2-(4-fluorophenyl)quinoxaline-6-carboxylate (260 mg, 0.51 mmol) in dichloromethane (20 mL) was added dropwise with stirring for 30 min at room temperature. The reaction mixture was concentrated under vacuum to give the residue, which was applied onto a silica gel column with 2%-5% ethyl acetate in petroleum ether to afford methyl 3-[6-(dimethylsulfamoyl)-1,2,3,4-tetrahydroquinolin-1-yl]-2-(4-fluorophenyl)quinoxaline-6-carboxylate as a yellow solid (240 mg, 91%).

(ES, m/z): [M+H]$^+$ 521.0

$^1$H-NMR (300 MHz, CDCl$_3$): δ 8.68 (d, J=1.5 Hz, 1H), 8.28-8.31 (m, 1H), 8.14 (d, J=5.7 Hz, 1H), 7.72-7.78 (m, 2H), 7.43 (d, J=2.1 Hz, 1H), 7.15-7.19 (m, 1H), 6.96-7.02 (m, 2H), 6.57 (d, J=8.4 Hz, 1H), 4.04 (s, 3H), 3.95-3.99 (t, J=6.0 Hz, 2H), 2.87-2.91 (t, J=6.9 Hz, 2H), 2.61 (s, 6H), 2.09-2.18 (m, 2H)

Example 11

Methyl 2-(benzofuran-3-yl)-3-(isopropyl(methyl)amino)quinoxaline-6-carboxylate

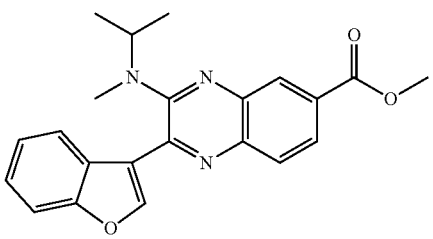 [SMILES: COC(=O)c1ccc2nc(-c3coc4ccccc34)c(N(C)C(C)C)nc2c1]

To a solution of methyl 2-chloro-3-(isopropyl(methyl)amino)quinoxaline-6-carboxylate (Scheme 1,150 mg, 0.51 mmol) in 1,4-dioxane (3 mL) was added 2-(benzofuran-3-yl)-4,4,5,5-tetramethyl-1,3,2-dioxaborolane (312 mg, 1.28 mmol), K$_3$PO$_4$ (326 mg, 1.53 mmol), Pd(PPh$_3$)$_4$ (30 mg, 0.03 mmol) and water (3 drops). After stirring 40 min at 95° C. under nitrogen atmosphere, the reaction mixture was dissolved in water (10 mL), extracted with dichloromethane (3×30 mL), dried over anhydrous magnesium sulfate and concentrated under reduced pressure to afford a residue, which was purified by a silica gel column with 1% ethyl acetate in petroleum ether to afford methyl 2-(benzofuran-3-yl)-3-(isopropyl(methyl)amino)quinoxaline-6-carboxylate as a light yellow solid (110 mg, 57%).

LC/MS: (ES, m/z): [M+H]$^+$ 376.0

$^1$H-NMR (300 MHz, DMSO) δ 8.75 (s, 1H), 8.25-8.31 (m, 2H), 7.98-8.06 (m, 2H), 7.72-7.75 (m, 1H), 7.41-7.46 (m, 2H), 4.24-4.28 (t, J=6.6 Hz, 1H), 3.93 (s, 3H), 2.76 (s, 3H), 1.09 (d, J=6.6 Hz, 6H)

Example 12

Methyl 2-(1H-indazol-5-yl)-3-(isopropyl(methyl)amino)quinoxaline-6-carboxylate

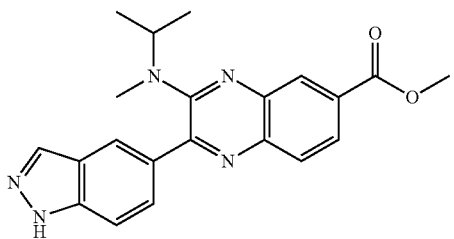 [SMILES: COC(=O)c1ccc2nc(-c3ccc4[nH]ncc4c3)c(N(C)C(C)C)nc2c1]

To a solution of methyl 2-chloro-3-(isopropyl(methyl)amino)quinoxaline-6-carboxylate (Scheme I, 200.0 mg, 0.68 mmol) in 1,4-dioxane (1 mL), was added 1H-indazol-5-ylboronic acid (386.0 mg, 2.38 mmol), K$_3$PO$_4$ (434.0 mg, 2.05 mmol), Pd(PPh$_3$)$_4$ (39.0 mg, 0.03 mmol) under nitrogen atmosphere and water (3 drops). After stirring for 20 min at 90° C., the reaction mixture was dissolved in water (30 mL), extracted with dichloromethane (3×20 mL), dried over anhydrous magnesium sulfate and concentrated under reduced pressure to afford a residue, which was purified by a silica gel column with 2%-10% ethyl acetate in petroleum ether to afford methyl 2-(1H-indazol-5-yl)-3-(isopropyl(methyl) amino)quinoxaline-6-carboxylate as a light yellow solid (110.0 mg, 45%).

LC/MS (ES, m/z): [M+H]⁺ 376.0

¹H-NMR (300 MHz, DMSO) δ 13.27 (s, 1H), 8.29 (d, J=9.6 Hz, 2H), 8.22 (s, 1H), 7.86-7.99 (m, 3H), 7.67 (d, J=8.7 Hz, 1H), 4.19-4.23 (t, J=6.6 Hz, 1H), 3.93 (s, 3H), 2.70 (s, 3H), 1.01 (d, J=6.6 Hz, 6H)

Example 13

Methyl 2-(6-(tert-butoxycarbonylamino)pyridin-3-yl)-3-(isopropyl(methyl)amino)quinoxaline-6-carboxylate

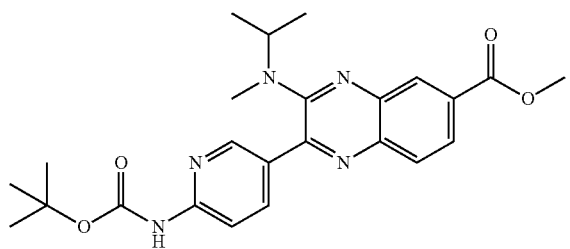 [SMILES: COC(=O)c1ccc2nc(-c3ccc(NC(=O)OC(C)(C)C)nc3)c(N(C)C(C)C)nc2c1]

To a solution of 6-(tert-butoxycarbonylamino)pyridin-3-ylboronic acid (316.0 mg, 1.33 mmol) in dioxane (5 mL) was added methyl 2-chloro-3-(isopropyl(methyl)amino)quinoxaline-6-carboxylate (130.0 mg, 0.44 mmol), K₃PO₄ (280.0 mg, 1.33 mmol) and Pd(PPh₃)₄ (25.6 mg, 0.02 mmol) and three drops water. The reaction mixture was stirred for 1 h at 90° C. in an oil bath with an inert atmosphere of nitrogen and concentrated under vacuum to give a residue, which was purified by a silica gel column with 1% ethyl acetate in petroleum ether to afford methyl 2-(6-(tert-butoxycarbonylamino)pyridin-3-yl)-3-(isopropyl(methyl)amino)quinoxaline-6-carboxylate as a light yellow solid (160 mg, 80%).

¹H-NMR (300 MHz, CDCl₃) δ 8.95 (d, J=2.4 Hz, 1H), 8.52-8.60 (m, 2H), 8.29-8.45 (m, 1H), 8.06-8.17 (m, 2H), 7.53-7.74 (m, 1H), 4.21-4.28 (m, 1H), 4.00 (s, 3H), 1.58 (s, 9H), 1.14 (d, J=6.6 Hz, 6H)

Example 14

Methyl 2-(benzofuran-2-yl)-3-(cyclopropyl(methyl) amino)quinoxaline-6-carboxylate

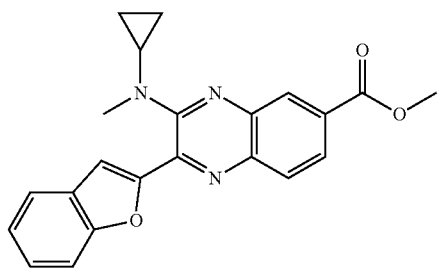 [SMILES: COC(=O)c1ccc2nc(-c3cc4ccccc4o3)c(N(C)C3CC3)nc2c1]

Step 1. Methyl 3-(cyclopropyl(methyl)amino)-2-oxo-1,2-dihydroquinoxaline-6-carboxylate

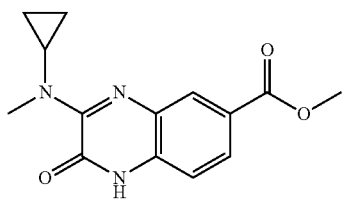

To a solution of methyl 3-chloro-2-oxo-1,2-dihydroquinoxaline-6-carboxylate (1.0 g, 4.20 mmol) in DMSO (6 mL) was added DIEA (1.35 g, 10.47 mmol), and N-methylcyclopropanamine hydrochloride (490 mg, 4.58 mmol). The solution was stirred 10 mins at room temperature and 2 h at 75° C. Then the reaction was quenched by the addition of water (100 mL) and the solids were collected by filtration to afford methyl 3-(cyclopropyl(methyl)amino)-2-oxo-1,2-dihydroquinoxaline-6-carboxylate as a yellow solid (405 mg, 35%).

LC/MS (ES, m/z): [M+H]⁺ 274.0

¹H-NMR (300 MHz, DMSO) δ 12.25 (s, 1H), 7.96 (d, J=1.8 Hz, 1H), 7.72-7.75 (m, 1H), 7.20 (d, J=8.4 Hz, 1H), 3.85 (d, J=5.4 Hz, 3H), 3.23 (s, 3H), 3.03-3.11 (m, 1H), 0.76-0.82 (m, 2H), 0.57-0.63 (m, 2H)

Step 2. Methyl 3-(cyclopropyl(methyl)amino)-2-(trifluoromethylsulfonyloxy)quinoxaline-6-carboxylate

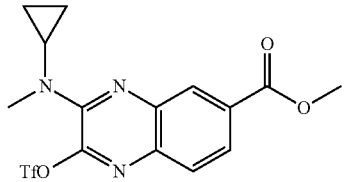

To a solution of methyl 3-(cyclopropyl(methyl)amino)-2-oxo-1,2-dihydroquinoxaline-6-carboxylate (126.0 mg, 0.46 mmol) in dichloromethane (34 mL) was added pyridine (145.0 mg, 1.84 mmol) and then Tf₂O (259 mg, 0.92 mmol) was added dropwise with stirring at 0° C. The resulting solution was stirred for 3 h at room temperature and then quenched by the addition of ice-water (50 mL), extracted with dichloromethane (2×20 mL), dried over anhydrous sodium sulfate and concentrated under vacuum to afford methyl 3-(cyclopropyl(methyl)amino)-2-(trifluoromethylsulfonyloxy)quinoxaline-6-carboxylate as red oil (180 mg, crude).

Step 3. Methyl 2-(benzofuran-2-yl)-3-(cyclopropyl (methyl)amino)quinoxaline-6-carboxylate

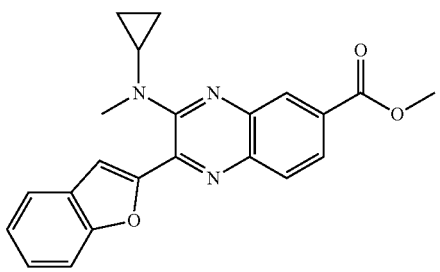 [SMILES: COC(=O)c1ccc2nc(-c3cc4ccccc4o3)c(N(C)C3CC3)nc2c1]

To a solution of methyl 3-(cyclopropyl(methyl)amino)-2-(trifluoromethylsulfonyloxy)quinoxaline-6-carboxylate (180.0 mg, crude) in dioxane (6 mL) was added benzofuran-2-ylboronic acid (149.0 mg, 0.92 mmol), K₃PO₄ (195.0 mg, 0.92 mmol), Pd(PPh₃)₄ (30.0 mg, 0.03 mmol) and water (3 drops). The resulting solution was stirred for 1 h at 90° C. and then concentrated under vacuum to give a residue, which was purified by a silica gel column with 5%-20% ethyl acetate in petroleum ether to afford methyl 2-(benzofuran-2-yl)-3-(cyclopropyl(methyl)amino)quinoxaline-6-carboxylate as a yellow solid (95.0 mg, 39% 2 steps).

LC/MS (ES, m/z): [M+H]⁺ 374.0

¹H-NMR (300 MHz, DMSO) δ 8.68 (s, 1H), 8.08-8.16 (m, 2H), 7.63-7.72 (m, 2H), 7.50 (d, J=0.6 Hz, 1H), 7.42-7.45 (m, 1H), 7.28-7.40 (m, 1H), 4.01 (s, 3H), 3.21 (s, 3H), 2.96-3.01 (m, 1H), 0.53-0.74 (m, 4H)

Example 15

Methyl 2-(5-fluorobenzo[b]thiophen-2-yl)-3-(isopropylmethyl)amino)quinoxaline-6-carboxylate

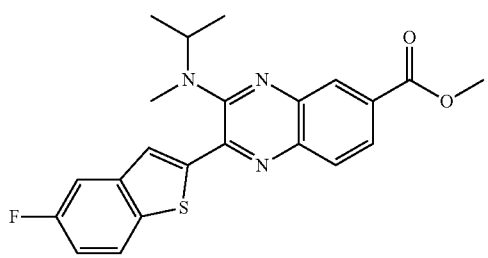

To a solution of 5-fluorobenzo[b]thiophen-2-ylboronic acid (202 mg, 1.03 mmol) in dioxane (6 mL) was added methyl 2-chloro-3-(isopropyl(methyl)amino)quinoxaline-6-carboxylate (120 mg, 0.41 mmol), K₃PO₄ (259 mg, 1.23 mmol), Pd(PPh₃)₄ (24.0 mg, 0.02 mmol) and water (3 drops) with stifling for 0.5 h at 90° C. in an oil bath with an inert atmosphere of nitrogen. The reaction mixture was concentrated under vacuum and then purified by a silica gel column with 1% to 2% ethyl acetate in petroleum ether to afford methyl 2-(5-fluorobenzo[b]thiophen-2-yl)-3-(isopropyl(methyl)amino)quinoxaline-6-carboxylate as a light yellow solid (148 mg, 88%).

LC/MS (ES, m/z): [M+H]⁺ 410.0

¹H-NMR (300 MHz, CDCl₃) δ 8.54 (d, J=1.5 Hz, 1H), 8.10-8.15 (m, 2H), 8.00 (d, J=8.4 Hz, 1H), 7.81-7.86 (m, 1H), 7.43-7.53 (m, 1H), 7.14-7.21 (m, 1H), 4.27-4.36 (m, 1H), 4.01 (s, 3H), 2.91 (s, 3H), 1.23 (d, J=6.6 Hz, 6H)

Example 16

Methyl 2-(6-fluoro-1H-inden-2-yl)-3-[(2S)-2-methylpiperidin-1-yl]quinoxaline-6-carboxylate

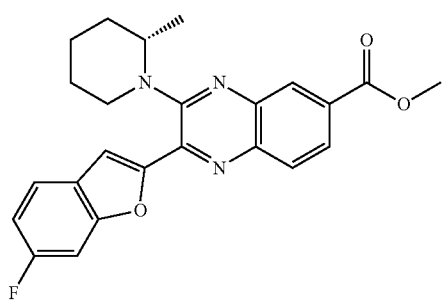 [SMILES: COC(=O)c1ccc2nc(-c3cc4ccc(F)cc4o3)c(N3CCCC[C@@H]3C)nc2c1]

Step 1. Methyl 3-[(2S)-2-methylpiperidin-1-yl]-2-oxo-1,2-dihydroquinoxaline-6-carboxylate

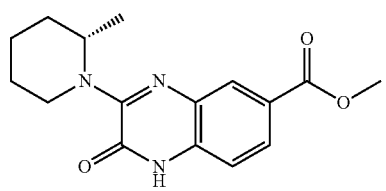 [SMILES: COC(=O)c1ccc2[nH]c(=O)c(N3CCCC[C@@H]3C)nc2c1]

To a solution of methyl 3-chloro-2-oxo-1,2-dihydroquinoxaline-6-carboxylate (500 mg, crude) in DMSO (6 mL) was added DIEA (543 mg, 4.20 mmol), (2S)-2-methylpiperidine (104 mg, 1.05 mmol). The solution was stirred for 6 h at 100° C. Then the reaction was quenched by the addition of water (50 mL). The resulting solution was extracted with ethyl acetate (4×30 mL) and the organic layers were concentrated under vacuum. The residue was purified by a silica gel column with 1%-5% ethyl acetate in petroleum ether to afford methyl 3-[(2S)-2-methylpiperidin-1-yl]-2-oxo-1,2-dihydroquinoxaline-6-carboxylate as a yellow solid (98 mg).

LC/MS (ES, m/z): [M+H]⁺ 302.0

¹H-NMR (300 MHz, CDCl₃) δ 9.39 (s, 1H), 8.28 (s, 1H), 7.83-7.86 (m, 1H), 7.05 (d, J=8.4 Hz, 1H), 5.36-5.40 (m, 1H), 4.88 (d, J=13.5 Hz, 1H), 3.94 (s, 1H), 3.16-3.25 (t, J=13.2 Hz, 1H), 1.50-1.94 (m, 6H), 1.44 (d, J=6.6 Hz, 3H)

Step 2. (S)-Methyl 3-(2-methylpiperidin-1-yl)-2-(trifluoromethylsulfonyloxy)quinoxaline-6-carboxylate

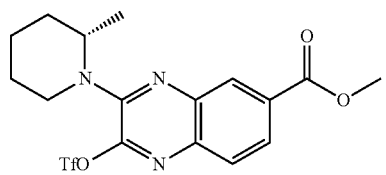 [SMILES: COC(=O)c1ccc2nc(OS(=O)(=O)C(F)(F)F)c(N3CCCC[C@@H]3C)nc2c1]

To a solution of methyl 3-[(2S)-2-methylpiperidin-1-yl]-2-oxo-1,2-dihydroquinoxaline-6-carboxylate (98 mg, 0.33 mmol) in dichloromethane (30 mL) was added pyridine (104 mg, 1.31 mmol), and then Tf₂O (186 mg, 0.66 mmol) was added dropwise with stirring at 0° C. The resulting solution was stirred overnight at room temperature and then quenched by the addition of ice-water (20 mL), extracted with dichloromethane (3×10 mL), dried over anhydrous sodium sulfate and concentrated under vacuum to afford (S)-methyl 3-(2-methylpiperidin-1-yl)-2-(trifluoromethylsulfonyloxy)quinoxaline-6-carboxylate as red oil (200 mg, crude).

Step 3. Methyl 2-(6-fluoro-1H-inden-2-yl)-3-[(2S)-2-methylpiperidin-1-yl]quinoxaline-6-carboxylate

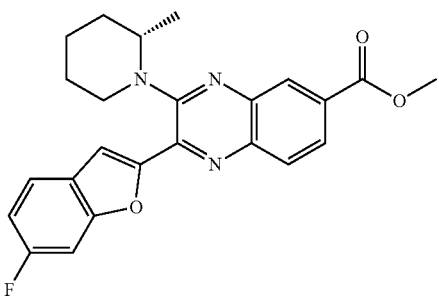 [SMILES: COC(=O)c1ccc2nc(-c3cc4ccc(F)cc4o3)c(N3CCCC[C@@H]3C)nc2c1]

To a solution of methyl 3-[(2S)-2-methylpiperidin-1-yl]-2-[(trifluoromethane)sulfonyloxy]quinoxaline-6-carboxylate (200 mg, crude) in dioxane (5 mL) was added 2-(6-fluoro-1-benzofuran-2-yl)-4,4,5,5-tetramethyl-1,3,2-dioxaborolane (250 mg, 0.95 mmol), Pd(PPh₃)₄ (27 mg, 0.02 mmol), K₃PO₄ (291 mg, 1.37 mmol) and water (5 drops) with stifling for 1 h at 90° C. maintained with an inert atmosphere of nitrogen in an oil bath. The reaction mixture was concentrated under vacuum to give the residue, which was applied onto a silica gel column with 1% to 2% ethyl acetate in petroleum to afford methyl 2-(6-fluoro-1H-inden-2-yl)-3-[(2S)-2-methylpiperidin-1-yl]quinoxaline-6-carboxylate as a yellow solid (50 mg).

LC/MS (ES, m/z): [M+H]⁺ 420.0

¹H-NMR (300 MHz, CDCl₃) δ 8.67 (s, 1H), 8.12-8.20 (m, 2H), 7.97 (s, 1H), 7.63-7.68 (m, 1H), 7.39-7.43 (m, 1H), 7.07-7.15 (m, 1H), 4.19 (s, 1H), 4.02 (s, 3H), 3.39 (s, 1H), 1.65-1.85 (m, 6H), 1.19 (d, J=6.3 Hz, 3H)

Example 17

Methyl 3-(azepan-1-yl)-2-(6-fluoro-1-benzofuran-2-yl)quinoxaline-6-carboxylate

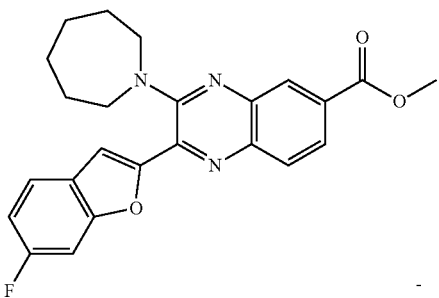 [SMILES: COC(=O)c1ccc2nc(-c3cc4ccc(F)cc4o3)c(N3CCCCCC3)nc2c1]

Step 1. Methyl 3-(azepan-1-yl)-2-oxo-1,2-dihydroquinoxaline-6-carboxylate

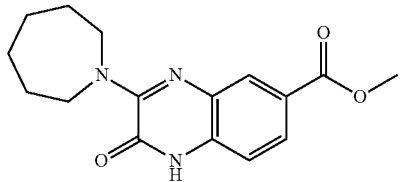 [SMILES: COC(=O)c1ccc2[nH]c(=O)c(N3CCCCCC3)nc2c1]

To a solution of methyl 3-chloro-2-oxo-1,2-dihydroquinoxaline-6-carboxylate (500 mg, crude) in DMSO (6 mL) was added DIEA (543 mg, 4.20 mmol) and azepane (208 mg, 2.10 mmol). The solution was stirred overnight at 90° C. Then the reaction was quenched by the addition of water (50 mL), extracted with ethyl acetate (5×20 mL) and the organic layers were concentrated under vacuum to give a residue, which was purified by a silica gel column with 1%-5% ethyl acetate in petroleum ether to afford methyl 3-(azepan-1-yl)-2-oxo-1,2-dihydroquinoxaline-6-carboxylate as a yellow solid (165 mg).

LC/MS (ES, m/z): [M+H]⁺ 302.0

¹H-NMR (300 MHz, CDCl₃) δ 9.74 (s, 1H), 8.16 (d, J=1.5 Hz, 1H), 7.78-7.82 (m, 1H), 7.02 (d, J=8.4 Hz, 1H), 4.04 (s, 4H), 3.94 (s, 3H), 1.91 (s, 4H), 1.54-1.66 (m, 4H)

Step 2. Methyl 3-(azepan-1-yl)-2-(trifluoromethylsulfonyloxy)quinoxaline-6-carboxylate

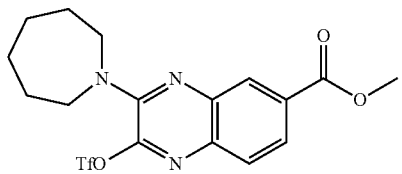 [SMILES: COC(=O)c1ccc2nc(OS(=O)(=O)C(F)(F)F)c(N3CCCCCC3)nc2c1]

To a solution of methyl 3-(azepan-1-yl)-2-oxo-1,2-dihydroquinoxaline-6-carboxylate (100 mg, 0.33 mmol) in dichloromethane (30 mL) was added pyridine (104 mg, 1.31 mmol) and then Tf₂O (186 mg, 0.66 mmol) was added dropwise with stirring at 0° C. The resulting solution was stirred overnight at room temperature and then quenched by the addition of ice-water (20 mL), extracted with dichloromethane (3×10 mL), dried over anhydrous sodium sulfate and concentrated under vacuum to afford methyl 3-(azepan-1-yl)-2-(trifluoromethylsulfonyloxy)quinoxaline-6-carboxylate as red oil (200 mg, crude).

Step 3. Methyl 3-(azepan-1-yl)-2-(6-fluoro-1-benzo-furan-2-yl)quinoxaline-6-carboxylate

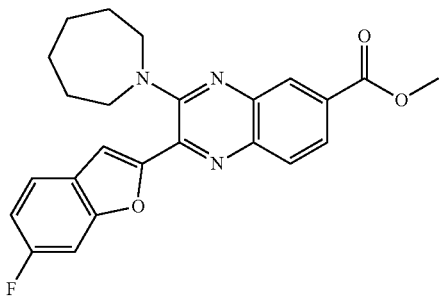 [SMILES: COC(=O)c1ccc2nc(-c3cc4ccc(F)cc4o3)c(N3CCCCCC3)nc2c1]

To a solution of methyl 3-(azepan-1-yl)-2-[(trifluoromethane)sulfonyloxy]quinoxaline-6-carboxylate (200 mg, crude) in 1,2-dimethoxyethane (5 mL) was added 2-(6-fluoro-1-benzofuran-2-yl)-4,4,5,5-tetramethyl-1,3,2-dioxaborolane (250 mg, 0.95 mmol), Pd(PPh$_3$)$_4$ (27 mg, 0.02 mmol), K$_3$PO$_4$ (291 mg, 1.37 mmol) and water (5 drops) with stirring for 1 h at 90° C. maintained with an inert atmosphere of nitrogen. The reaction mixture was concentrated under vacuum to give the residue, which was applied onto a silica gel column with 1% to 2% ethyl acetate in petroleum to afford methyl 3-(azepan-1-yl)-2-(6-fluoro-1-benzofuran-2-yl)quinoxaline-6-carboxylate as a yellow solid (73 mg).

LC/MS (ES, m/z): [M+H]$^+$ 420.0

$^1$H-NMR (300 MHz, CDCl$_3$) δ 8.59 (s, 1H), 8.00-8.08 (m, 2H), 7.60-7.65 (m, 1H), 7.41 (s, 1H), 7.34-7.38 (m, 1H), 7.06-7.13 (m, 1H), 4.01 (s, 3H), 3.64-3.68 (t, J=6.0 Hz, 4H), 1.83-1.90 (m, 4H), 1.60-1.76 (m, 4H)

Example 18

Methyl 3-[methyl(propan-2-yl)amino]-2-(4-phenylfuran-2-yl)quinoxaline-6-carboxylate

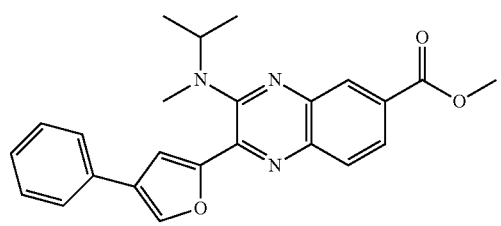 [SMILES: COC(=O)c1ccc2nc(-c3cc(-c4ccccc4)co3)c(N(C)C(C)C)nc2c1]

Step 1. 3-Phenylfuran

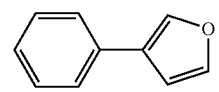

To a solution of phenylboronic acid (15 g, 123.02 mmol) in dioxane (150.0 mL) and water (3.0 mL) was added 3-bromofuran (16.3 g, 110.91 mmol), K$_3$PO$_4$ (43 g, 202.57 mmol) and Pd(PPh$_3$)$_4$ (6.0 g, 5.19 mmol) with stirring for 2 h at 90° C. in an oil bath maintained with an inert atmosphere of nitrogen. The reaction mixture was concentrated under reduced pressure to give the residue, which was purified by silica gel column chromatography eluting with 1% ethyl acetate in petroleum ether to afford 3-phenylfuran as a white solid (15 g, 85%).

$^1$H-NMR (300 MHz, CDCl$_3$): δ 7.76 (s, 1H), 7.51-7.54 (m, 3H), 7.40-7.47 (m, 2H), 7.29-7.38 (m, 1H), 6.73 (d, J=0.9 Hz, 1H)

Step 2. 4,4,5,5-Tetramethyl-2-(4-phenylfuran-2-yl)-1,3,2-dioxaborolane

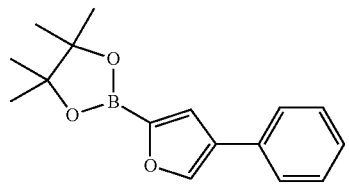 [SMILES: CC1(C)OB(c2cc(-c3ccccc3)co2)OC1(C)C]

A solution of n-BuLi (6.2 mL, 2.5 M solution in hexane) was added drop-wise to a solution of 3-phenylfuran (1.5 g, 10.40 mmol) in dry tetrahydrofuran (100 mL) at −78° C. under nitrogen. It was warmed slowly to −40° C. over 45 min and stirred at this temperature for another 30 min. The mixture was cooled again to −78° C. followed by the dropwise addition of 4,4,5,5-tetramethyl-2-(propan-2-yloxy)-1,3,2-dioxaborolane (3.72 g, 19.99 mmol). After warming to room temperature, the mixture was quenched with NH$_4$Cl (aq) and extracted with ethyl acetate (3×80 mL). The combined organic layers were dried over anhydrous sodium sulfate, filtered and concentrated in vacuo to give the residue, which was precipitated by cooling to afford 4,4,5,5-tetramethyl-2-(3-phenylfuran-2-yl)-1,3,2-dioxaborone as a white solid (400 mg, 14.0%). The mother liquid was purified by silica gel column chromatography eluting with 2% ethyl acetate in petroleum ether to afford 4,4,5,5-tetramethyl-2-(4-phenylfuran-2-yl)-1,3,2-dioxaborolane (200 mg, crude), which was used to the next step without further purification.

Step 3. Methyl 3-[methyl(propan-2-yl)amino]-2-(4-phenylfuran-2-yl)quinoxaline-6-carboxylate

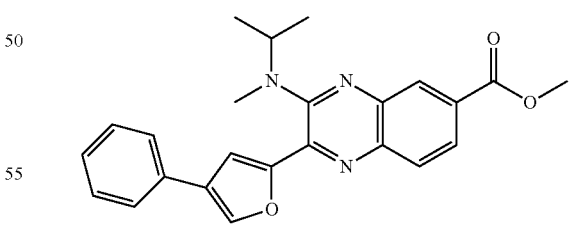

To a solution of 4,4,5,5-tetramethyl-2-(4-phenylfuran-2-yl)-1,3,2-dioxaborolane (200 mg, crude) in dioxane (5.5 mL) and water (3 drops) was added methyl 2-chloro-3-[methyl(propan-2-yl)amino]quinoxaline-6-carboxylate (72 mg, 0.25 mmol), K$_3$PO$_4$ (156 mg, 0.73 mmol) and Pd(PPh$_3$)$_4$ (14 mg, 0.01 mmol) with stifling for 1 h at 95° C. in an oil bath which was maintained under an inert atmosphere of nitrogen. The reaction mixture was concentrated under reduced pressure to give the residue, which was purified by silica gel column chromatography eluting with 2% ethyl acetate in petroleum ether to afford methyl 3-[methyl(propan-2-yl)amino]-2-(5-phenylfuran-2-yl)quinoxaline-6-carboxylate as a light yellow solid (50 mg).

LC/MS (ES, m/z): [M+H]$^+$ 401.0

$^1$H-NMR (300 MHz, CDCl$_3$): δ 8.54 (s, 1H), 8.03-8.13 (m, 2H), 7.96 (s, 1H), 7.58-7.63 (m, 3H), 7.43-7.47 (m, 3H), 4.28-4.32 (m, 1H), 4.00 (s, 1H), 2.93 (s, 3H), 1.25 (d, J=6.6 Hz, 6H)

Example 19

(R)-Methyl 2-(benzo[d][1,3]dioxol-5-yl)-3-(2-methylpyrrolidin-1-yl)quinoxaline-6-carboxylate

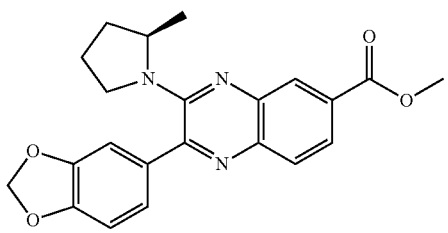 [SMILES: COC(=O)c1ccc2nc(-c3ccc4c(c3)OCO4)c(N3CCC[C@H]3C)nc2c1]

Step 1. (R)-Methyl 3-(2-methylpyrrolidin-1-yl)-2-oxo-1,2-dihydroquinoxaline-6-carboxylate

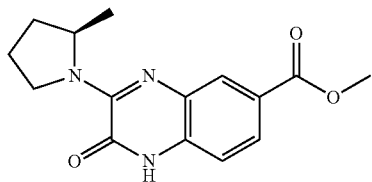 [SMILES: COC(=O)c1ccc2[nH]c(=O)c(N3CCC[C@H]3C)nc2c1]

To a solution of methyl 3-chloro-2-oxo-1,2-dihydroquinoxaline-6-carboxylate (250 mg, 1.05 mmol) in DMSO (2 mL) was added DIEA (850 mg, 4.2 mmol), and (R)-2-methylpyrrolidine hydrochloride (300 mg, 2.35 mmol), and the resulting mixture was stirred for 3 h at 70° C. Then the reaction was quenched by the addition of water (10 mL). The solids were collected by filtration to afford (R)-methyl 3-(2-methylpyrrolidin-1-yl)-2-oxo-1,2-dihydroquinoxaline-6-carboxylate as a light yellow solid (216 mg, 72%).

LC/MS (ES, m/z): [M+H]$^+$ 288.0

Step 2. (R)-Methyl 3-(2-methylpyrrolidin-1-yl)-2-(trifluoromethylsulfonyloxy)quinoxaline-6-carboxylate

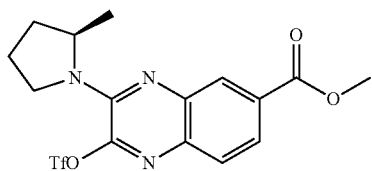 [SMILES: COC(=O)c1ccc2nc(OS(=O)(=O)C(F)(F)F)c(N3CCC[C@H]3C)nc2c1]

To a solution of (R)-methyl 3-(2-methylpyrrolidin-1-yl)-2-oxo-1,2-dihydroquinoxaline-6-carboxylate (200 mg, 0.70 mmol) in dichloromethane (30 mL) was added pyridine (221 mg, 2.79 mmol) and then Tf$_2$O (395 mg, 1.40 mmol) dropwise with stifling at 0° C. The resulting solution was stirred overnight at room temperature, then quenched by the addition of ice-water (50 mL), extracted with dichloromethane (3×20 mL), dried over anhydrous sodium sulfate and concentrated under vacuum to afford (R)-methyl 3-(2-methylpyrrolidin-1-yl)-2-(trifluoromethylsulfonyloxy)quinoxaline-6-carboxylate as red oil (250 mg, crude).

Step 3. (R)-Methyl 2-(benzo[d][1,3]dioxol-5-yl)-3-(2-methylpyrrolidin-1-yl)quinoxaline-6-carboxylate

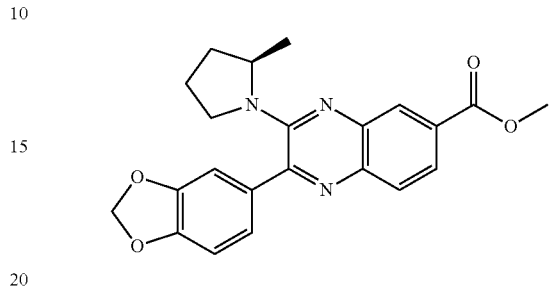

To a solution of (R)-methyl 3-(2-methylpyrrolidin-1-yl)-2-(trifluoromethylsulfonyloxy) quinoxaline-6-carboxylate (250 mg, crude) in dioxane (5 mL) was added 2-(benzo[d][1,3]dioxol-5-yl)-4,4,5,5-tetramethyl-1,3,2-dioxaborolane (250 mg, 1.51 mmol), K$_3$PO$_4$ (380 mg, 1.79 mmol), Pd(PPh$_3$)$_4$ (35 mg, 0.03 mmol) and water (5 drops). The resulting solution was stirred for 1 h at 90° C. and then concentrated under vacuum to give a residue, which was purified via silica gel chromatography (1%-5% ethyl acetate in petroleum ether) to afford (R)-methyl 2-(benzo[d][1,3]dioxol-5-yl)-3-(2-methylpyrrolidin-1-yl)quinoxaline-6-carboxylate as a yellow solid (120 mg).

LC/MS (ES, m/z): [M+H]$^+$ 392.0

$^1$H-NMR (300 MHz, CDCl$_3$): δ 8.56 (s, 1H), 7.93-8.03 (m, 2H), 7.28-7.32 (s, 2H), 6.93 (d, J=7.8 Hz, 1H), 6.07 (s, 2H), 4.35-4.42 (m, 1H), 4.00 (s, 3H), 3.25 (d, J=6.3 Hz, 1H), 2.95-3.04 (m, 1H), 2.15-2.25 (m, 1H), 1.86-1.91 (m, 1H), 1.53-1.70 (m, 2H), 1.39 (d, J=5.4 Hz, 3H)

Example 20

(R)-Methyl 2-(4-fluorophenyl)-3-(2-(trifluoromethyl)pyrrolidin-1-yl)quinoxaline-6-carboxylate

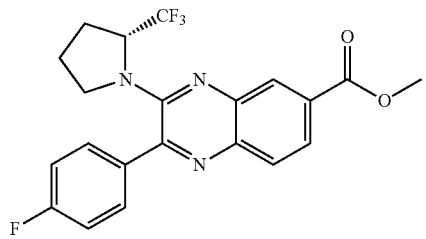 [SMILES: COC(=O)c1ccc2nc(-c3ccc(F)cc3)c(N3CCC[C@@H]3C(F)(F)F)nc2c1]

To a solution of methyl 3-chloro-2-(4-fluorophenyl)quinoxaline-6-carboxylate (270 mg, 0.85 mmol) in DMSO (1 mL) was added (R)-2-(trifluoromethyl)pyrrolidine (275 mg, 1.99 mmol). The resulting solution was stirred 7 days at 130° C. and then evaporated in vacuo. The residue was diluted with petroleum ether (15 mL) and filtered. The filtrate was concentrated and purified by a silica gel column chromatography with 2%-10% ethyl acetate in petroleum ether to afford (R)-methyl 2-(4-fluorophenyl)-3-(2-(trifluoromethyl)pyrrolidin-1-yl)quinoxaline-6-carboxylate as a yellow solid (35 mg, crude).

LC/MS (ES, m/z): [M+H]$^+$ 420.0

Example 21

Methyl 2-(4-carbamoylphenyl)-3-(isopropylmethyl) amino)quinoxaline-6-carboxylate

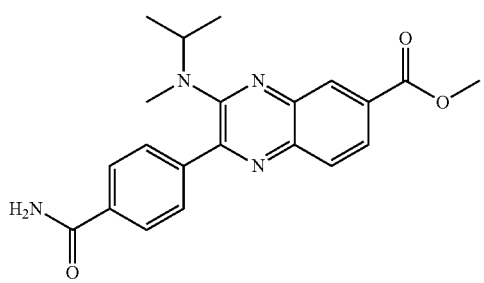 [SMILES: COC(=O)c1ccc2nc(-c3ccc(C(N)=O)cc3)c(N(C)C(C)C)nc2c1]

To a solution of methyl 2-chloro-3-(isopropyl(methyl) amino)quinoxaline-6-carboxylate (120 mg, 0.49 mmol) in dioxane (5 mL) was added 4-carbamoylphenylboronic acid (169 mg, 1.02 mmol), $K_3PO_4$ (217 mg, 1.02 mmol), $Pd(PPh_3)_4$ (30 mg, 0.03 mmol) and water (5 drops). The resulting solution was stirred for 1 hour at 90° C. and then concentrated in vacuo to give a residue, which was purified via silica gel column chromatography (9% ethyl acetate in petroleum ether) to afford methyl 2-(4-carbamoylphenyl)-3-(isopropyl(methyl)amino)quinoxaline-6-carboxylate as a yellow solid (103 mg, 66%).

LC/MS (ES, m/z): [M+H]+ 379.0

$^1$H-NMR (300 MHz, DMSO): δ 8.28 (d, J=1.2 Hz, 1H), 8.09 (s, 1H), 8.01 (d, J=8.4 Hz, 2H), 7.96-7.98 (m, 2H), 7.89-7.94 (m, 2H), 7.48 (s, 1H), 4.18-4.27 (m, 1H), 3.93 (s, 3H), 2.66 (s, 3H), 1.04 (d, J=6.6 Hz, 3H)

Example 22

Methyl 2-(4-fluorophenyl)-3-(((1r,4r)-4-hydroxycyclohexyl)(methyl)amino)quinoxaline-6-carboxylate

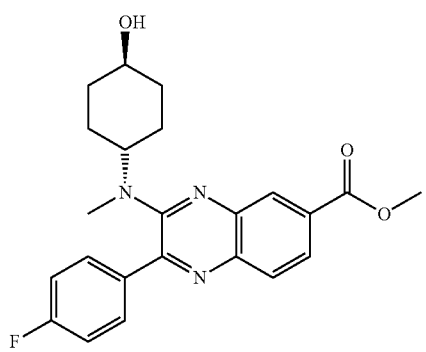

To a solution of methyl 3-chloro-2-(4-fluorophenyl)quinoxaline-6-carboxylate (408 mg, 1.29 mmol) in DMSO (20 ml) was added trans-4-(methylamino)cyclohexan-1-ol (200 mg, 1.55 mmol) and DIEA (499 mg, 3.86 mmol), and the reaction mixture was allowed to react with stirring overnight at 100° C. in an oil bath. The reaction mixture was diluted with water (200 ml), extracted with dichloromethane (4×50 ml). The organic layers were combined, dried over anhydrous magnesium sulfate, and concentrated in vacuo to give the residue, which was purified via silica gel column chromatography (5% ethyl acetate in petroleum ether) to afford methyl 2-(4-fluorophenyl)-3-(((1r,4r)-4-hydroxycyclohexyl)(methyl)amino)quinoxaline-6-carboxylate as a yellow solid (130 mg, 25%).

LC/MS (ES, m/z): [M+H]+ 410.0

$^1$H-NMR (300 MHz, DMSO) δ 8.27 (s, 1H), 7.93-7.99 (m, 2H), 7.85-7.90 (m, 2H), 7.36-7.41 (t, J=8.4 Hz, 2H), 3.93 (s, 3H), 3.65-3.69 (m, 1H), 3.26-3.29 (m, 1H), 2.74 (s, 3H), 1.76-1.79 (m, 2H), 1.51-1.58 (m, 4H), 0.97-1.01 (m, 2H)

Example 23

(S)-Methyl 3-(4-ethyl-2-methylpiperazin-1-yl)-2-(4-fluorophenyl)quinoxaline-6-carboxylate

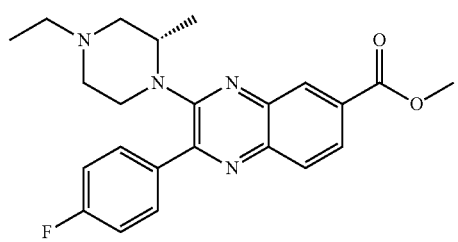 [SMILES: CCN1CCN(c2nc3cc(C(=O)OC)ccc3nc2-c2ccc(F)cc2)[C@@H](C)C1]

To a solution of (S)-methyl 2-(4-fluorophenyl)-3-(2-methylpiperazin-1-yl)quinoxaline-6-carboxylate (160 mg, 0.42 mmol) in N,N-dimethylformamide (30 mL) was added potassium carbonate (174 mg, 1.26 mmol) and $CH_3CH_2I$ (68.8 mg, 0.44 mmol), and the reaction was stirred overnight at room temperature. The reaction solution was diluted with water (150 mL), extracted with dichloromethane (3×30 mL), and the organic layers combined, dried over anhydrous magnesium sulfate, and concentrated in vacuo. The residue was purified by silica gel column chromatography (1% methanol in dichloromethane) to afford (S)-methyl 3-(4-ethyl-2-methylpiperazin-1-yl)-2-(4-fluorophenyl)quinoxaline-6-carboxylate as light yellow oil (80 mg, crude).

LC/MS (ES, m/z): [M+H]+ 408.0

Example 24

2,2,2-Trifluoro-1-(5-(3-(isopropyl(methyl)amino)-6-(1H-tetrazol-5-yl)quinoxalin-2-yl)-2-methyl-1H-indol-3-yl)ethanone

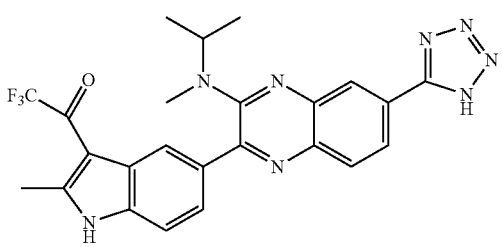 [SMILES: Cc1[nH]c2ccc(-c3nc4ccc(-c5nnn[nH]5)cc4nc3N(C)C(C)C)cc2c1C(=O)C(F)(F)F]

Step 1. 5-Bromo-2-methyl-1H-indole

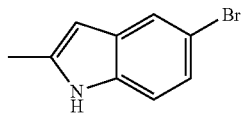

To a solution of 2-methyl-1H-indole (5.0 g, 38.12 mmol) in sulfuric acid (80 ml) was added Ag$_2$SO$_4$ (12.5 g, 40.06 mmol) with ice cooling, and the solution was stirred for 30 min. Then Br$_2$ (6.4 g, 40.05 mmol) was added to the solution dropwise over 30 min. After the solution was stirred for 4 h at room temperature, the reaction was quenched by the addition of water/ice (300 ml). The reaction mixture was extracted with dichloromethane (3×200 ml) and the organic layers combined, dried over anhydrous sodium sulfate and concentrated in vacuo to afford 5-bromo-2-methyl-1H-indole as a light brown solid (4.7 g, 59%).

LC/MS (ES, m/z): [M+H]$^+$ 211.0

$^1$H-NMR (300 MHz, CDCl$_3$): δ 11.23 (s, 1H), 7.56 (s, 1H), 7.21 (d, J=8.7 Hz, 1H), 7.07-7.09 (m, 1H), 6.11 (s, 1H), 2.38 (s, 3H)

Step 2. 2-Methyl-5-(4,4,5,5-tetramethyl-1,3,2-dioxaborolan-2-yl)-1H-indole

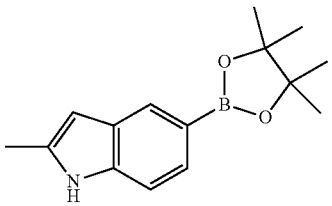

To a solution of 5-bromo-2-methyl-1H-indole (3.0 g, 14.35 mmol) in dry tetrahydrofuran (20 ml) was added sodium hydride (900 mg, 22.5 mmol) with ice-cooling. After stifling for about 30 min, a solution of t-BuLi (27.5 ml, 1.3 M solution in hexane) was added dropwise with stifling at −78° C. under an inert atmosphere of nitrogen. The reaction mixture was warmed slowly to −40° C. over 45 min and stirred at this temperature for another 30 min. The mixture was cooled again below −78° C., followed by the addition of 4,4,5,5-tetramethyl-2-(propan-2-yloxy)-1,3,2-dioxaborolane (5.3 g, 28.49 mmol) dropwise. After warming to room temperature, the mixture was quenched with NH$_4$Cl solution (100 ml) and extracted with ethyl acetate (3×100 ml). The combined organic layers were dried over anhydrous sodium sulfate, filtered and concentrated under reduced pressure to give the residue, which was purified by a silica gel column (2% ethyl acetate in petroleum ether) to afford 2-methyl-5-(4,4,5,5-tetramethyl-1,3,2-dioxaborolan-2-yl)-1H-indole (1.4 g, 38%). $^1$H NMR (300 MHz, CDCl$_3$): δ 8.06 (s, 1H), 7.91 (s, 1H), 7.58-7.60 (t, J=7.5 Hz, 1H), 7.31 (d, J=8.1 Hz, 1H), 6.24 (s, 1H), 2.46 (s, 3H), 1.39 (s, 12H).

Step 3. Methyl 3-[methyl(propan-2-yl)amino]-2-(2-methyl-1H-indol-5-yl)quinoxaline-6-carboxylate

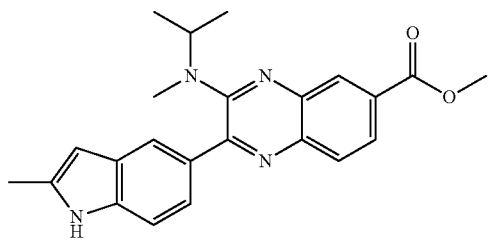

To a solution of methyl 2-chloro-3-[methyl(propan-2-yl)amino]quinoxaline-6-carboxylate (850 mg, 2.90 mmol) in DME (20 ml) was added 2-methyl-5-(4,4,5,5-tetramethyl-1,3,2-dioxaborolan-2-yl)-1H-indole (1.4 g, 5.44 mmol), potassium carbonate (751 mg, 5.43 mmol), Pd(PPh$_3$)$_4$ (157 mg, 0.14 mmol) and water (5 ml) under an inert atmosphere of nitrogen. The resulting solution was stirred for 1 h at 90° C. and then diluted with water (300 ml), extracted with ethyl acetate (3×100 ml), and the organic layers combined and dried over anhydrous magnesium sulfate and concentrated in vacuo to give a residue, which was purified by a silica gel column (1%-5% ethyl acetate in petroleum ether) to afford methyl 3-[methyl(propan-2-yl)amino]-2-(2-methyl-1H-indol-5-yl)quinoxaline-6-carboxylate as a yellow solid (660 mg, 58%).

LC/MS (ES, m/z): [M+H]$^+$ 389.0

$^1$H-NMR (300 MHz, CDCl$_3$) δ 8.53 (d, J=1.2 Hz, 1H), 8.09 (s, 1H), 7.97-8.08 (m, 3H), 7.66-7.69 (m, 1H), 7.37 (d, J=8.4 Hz, 1H), 6.31 (s, 1H), 4.31-4.38 (m, 1H), 4.00 (s, 3H), 2.76 (s, 3H), 2.50 (s, 3H), 1.06 (d, J=6.6 Hz, 6H)

Step 4. 3-[Methyl(propan-2-yl)amino]-2-(2-methyl-1H-indol-5-yl)quinoxaline-6-carboxylic acid

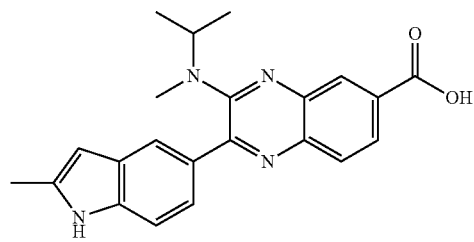 [SMILES: Cc1cc2cc(-c3nc4ccc(C(=O)O)cc4nc3N(C)C(C)C)ccc2[nH]1]

To a solution of methyl 3-[methyl(propan-2-yl)amino]-2-(2-methyl-1H-indol-5-yl)quinoxaline-6-carboxylate (660 mg, 1.70 mmol) in methanol (40 ml) was added a solution of NaOH (340 mg, 8.50 mmol) in water (5 ml). The resulting solution was stirred overnight at room temperature and then concentrated in vacuo. The residue was dissolved in water (20 ml), adjusted to pH 4 with HCl (3N). The product was precipitated from water and collected by filtration to afford 3-[methyl(propan-2-yl)amino]-2-(2-methyl-1H-indol-5-yl)quinoxaline-6-carboxylic acid as a orange solid (500 mg, 78%).

LC/MS (ES, m/z): [M+H]$^+$ 375.0

¹H-NMR (300 MHz, DMSO) δ 11.14 (s, 1H), 8.24 (s, 1H), 7.97 (d, J=7.2 Hz, 1H), 7.91 (s, 1H), 7.53-7.57 (m, 1H), 7.36 (d, J=8.4 Hz, 1H), 6.24 (s, 1H), 4.15-4.24 (m, 1H), 2.70 (s, 3H), 2.41 (s, 3H), 0.98 (d, J=6.6 Hz, 6H)

Step 5. N-tert-Butyl-3-[methyl(propan-2-yl)amino]-2-(2-methyl-1H-indol-5-yl)quinoxaline-6-carboxamide

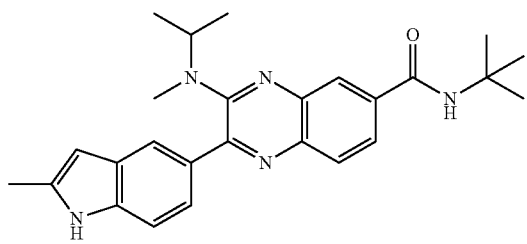 [SMILES: Cc1cc2cc(-c3nc4ccc(C(=O)NC(C)(C)C)cc4nc3N(C)C(C)C)ccc2[nH]1]

To a solution of 3-[methyl(propan-2-yl)amino]-2-(2-methyl-1H-indol-5-yl)quinoxaline-6-carboxylic acid (350 mg, 0.94 mmol) in dichloromethane (20 ml) was added TEA (202 mg, 2.00 mmol) 2-methylpropan-2-amine (117 mg, 1.60 mmol), and T₃P (650 mg, 50% ethyl acetate solution). The resulting solution was stirred overnight at room temperature and then concentrated in vacuo to afford N-tert-butyl-3-[methyl(propan-2-yl)amino]-2-(2-methyl-1H-indol-5-yl)quinoxaline-6-carboxamide as yellow oil (450 mg, crude).

LC/MS (ES, m/z): [M+H]⁺ 430.0.

Step 6. 3-[Methyl(propan-2-yl)amino]-2-[2-methyl-3-(2,2,2-trifluoroacetyl)-1H-indol-5-yl]quinoxaline-6-carbonitrile

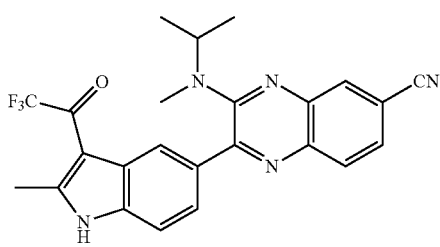 [SMILES: Cc1[nH]c2ccc(-c3nc4ccc(C#N)cc4nc3N(C)C(C)C)cc2c1C(=O)C(F)(F)F]

To a solution of N-tert-butyl-3-[methyl(propan-2-yl)amino]-2-(2-methyl-1H-indol-5-yl)quinoxaline-6-carboxamide (450 mg, crude) in dichloromethane (20 ml) was added TFAA (6 ml). The resulting solution was stirred overnight at room temperature and diluted with water (100 ml), adjusted to pH 8 with sodium bicarbonate solution, extracted with dichloromethane (3×50 ml), and the organic layers combined and dried over anhydrous magnesium sulfate and concentrated in vacuo to give a residue, which was purified by silica gel column chromatography (5%-10% ethyl acetate in petroleum ether) to afford 3-[methyl(propan-2-yl)amino]-2-[2-methyl-3-(2,2,2-trifluoroacetyl)-1H-indol-5-yl]quinoxaline-6-carbonitrile as a orange solid (160 mg).

LC/MS (ES, m/z): [M+H]⁺ 452.0

¹H-NMR (300 MHz, CDCl₃) δ 8.96 (s, 1H), 8.60 (s, 1H), 8.13 (d, J=1.5 Hz, 1H), 7.98 (d, J=8.7 Hz, 1H), 7.84-7.88 (m, 1H), 7.55-7.59 (m, 1H), 7.49 (d, J=2.8 Hz, 1H), 4.40-4.49 (m, 1H), 2.84 (s, 3H), 2.78 (s, 3H), 1.11 (d, J=6.6 Hz, 6H)

Step 7. 2,2,2-Trifluoro-1-(5-(3-(isopropyl(methyl)amino)-6-(1H-tetrazol-5-yl)quinoxalin-2-yl)-2-methyl-1H-indol-3-yl)ethanone

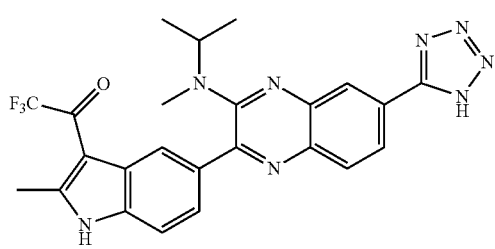 [SMILES: Cc1[nH]c2ccc(-c3nc4ccc(-c5nnn[nH]5)cc4nc3N(C)C(C)C)cc2c1C(=O)C(F)(F)F]

To a solution of 3-[methyl(propan-2-yl)amino]-2-[2-methyl-3-(2,2,2-trifluoroacetyl)-1H-indol-5-yl]quinoxaline-6-carbonitrile (160 mg, 0.35 mmol) in DMSO (20 ml) was added ZnBr₂ (38 mg, 0.17 mmol) and NaN₃ (91 mg, 1.40 mmol) in water (2 ml). The resulting solution was heated to reflux overnight and diluted with water (200 ml), adjusted to pH 3 with HCl (2N), extracted with ethyl acetate (5×50 ml), and the organic layers combined and dried over anhydrous magnesium sulfate and concentrated in vacuo to give a residue, which was purified by silica gel column chromatography (15% dichloromethane in methanol) to afford 2,2,2-trifluoro-1-(5-(3-(isopropyl(methyl)amino)-6-(1H-tetrazol-5-yl)quinoxalin-2-yl)-2-methyl-1H-indol-3-yl)ethanone as a yellow solid (38.6 mg, 27%).

LC/MS (ES, m/z): [M+H]⁺ 495.1

¹H-NMR (300 MHz, CD₃OD) δ 8.55 (s, 1H), 8.45 (d, J=0.9 Hz, 1H), 8.08-8.09 (t, J=1.5 Hz, 2H), 7.81-7.84 (m, 1H), 7.60 (d, J=8.4 Hz, 1H), 4.35-4.40 (m, 1H), 2.78 (d, J=9.6 Hz, 6H), 1.10 (d, J=6.6 Hz, 6H)

Example 25

2,3-Bis(4-fluorophenyl)-6-(1H-tetrazol-5-yl) quinoxaline

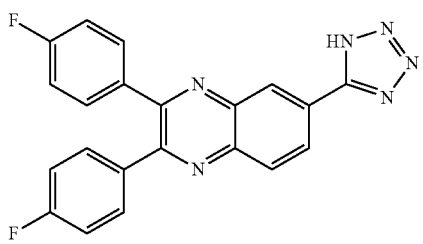 [SMILES: Fc1ccc(-c2nc3ccc(-c4nnn[nH]4)cc3nc2-c2ccc(F)cc2)cc1]

Step 1.
2,3-Bis(4-fluorophenyl)quinoxaline-6-carbonitrile

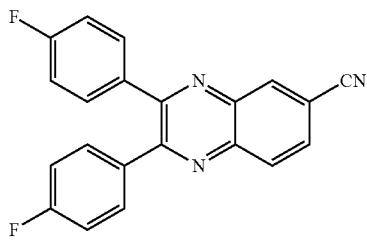 [SMILES: N#Cc1ccc2nc(-c3ccc(F)cc3)c(-c3ccc(F)cc3)nc2c1]

A solution of 1,2-bis(4-fluorophenyl)ethane-1,2-dione (600 mg, 2.44 mmol, 1.00 equiv) in acetic acid (23 mL) and 3,4-diaminobenzonitrile (389.3 mg, 2.93 mmol, 1.20 equiv) was stirred for 30 mins at 30° C. in an oil bath. The resulting solution was allowed to react, with stifling, for an additional 2 h while the temperature was maintained at 120° C. in an oil bath. The residue was applied onto a silica gel column (PE/EA (10:1)). This resulted in 349 mg (39%) of 2,3-bis(4-fluorophenyl)quinoxaline-6-carbonitrile as a white solid.

Step 2. 2,3-Bis(4-fluorophenyl)-6-(1H-tetrazol-5-yl)quinoxaline

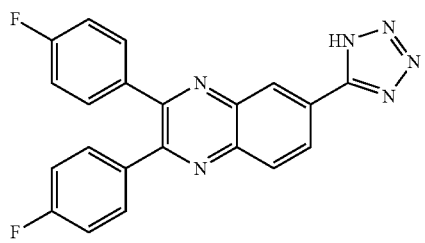 [SMILES: Fc1ccc(-c2nc3ccc(-c4nnn[nH]4)cc3nc2-c2ccc(F)cc2)cc1]

A solution of 2,3-bis(4-fluorophenyl)quinoxaline-6-carbonitrile (150 mg, 0.44 mmol, 1.00 equiv) in N,N-dimethylformamide (10 mL), NaN3 (500 mg, 7.69 mmol, 17.59 equiv), and NH$_4$Cl (116 mg, 2.19 mmol, 5.00 equiv) was stirred for 4 h at 100° C. in an oil bath. The reaction was then quenched by the addition of water. The resulting solution was extracted with 7×50 mL of dichloromethane and the organic layers combined and dried over anhydrous sodium sulfate. The resulting mixture was concentrated in vacuo, washed with dichloromethane, resulting in 34 mg (20%) of 2,3-bis(4-fluorophenyl)-6-(1H-tetrazol-5-yl)quinoxaline as a white solid.

LC-MS: (ES, m/z): 387 [M+H]+

$^1$H-NMR (300 MHz, d6-DMSO, ppm) δ 8.818, 8.812 (1H, d, J=1.8 Hz), 8.530-8.495 (1H, m), 7.393, 7.364 (1H, d, J=8.7 Hz), 7.608-7.557 (4H, m), 7.307-7.241 (4H, m)

Example 26

2,3-Bis(4-methoxyphenyl)-6-(1H-tetrazol-5-yl)quinoxaline

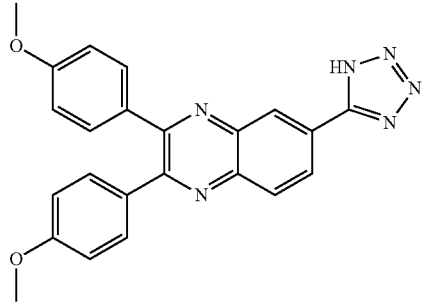 [SMILES: COc1ccc(-c2nc3ccc(-c4nnn[nH]4)cc3nc2-c2ccc(OC)cc2)cc1]

Step 1.
3-Bis(4-methoxyphenyl)quinoxaline-6-carbonitrile

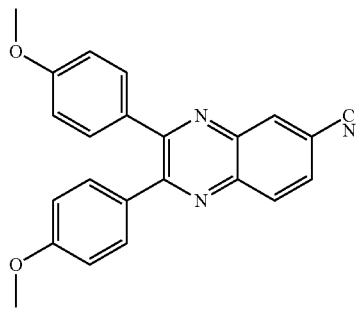 [SMILES: COc1ccc(-c2nc3ccc(C#N)cc3nc2-c2ccc(OC)cc2)cc1]

A solution of 1,2-bis(4-methoxyphenyl)ethane-1,2-dione (200 mg, 0.74 mmol, 1.00 equiv) in acetic acid (20 mL) and 3,4-diaminobenzonitrile (118.2 mg, 0.89 mmol, 1.20 equiv) was stirred for 1 h at reflux in an oil bath. The reaction was then quenched by the addition of water. The solids were collected by filtration and washed with MeOH. This resulted in 205 mg (71%) of 2,3-bis(4-methoxyphenyl)quinoxaline-6-carbonitrile as a yellow solid.

LC-MS (ES, m/z): 368 [M+H]+

Step 2. 2,3-Bis(4-methoxyphenyl)-6-(1H-tetrazol-5-yl)quinoxaline

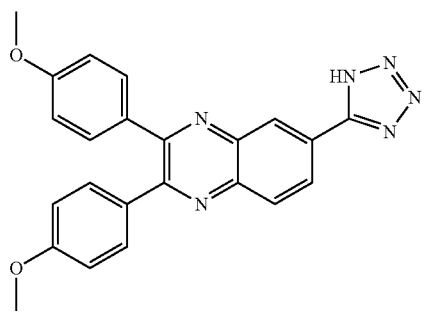 [SMILES: COc1ccc(-c2nc3ccc(-c4nnn[nH]4)cc3nc2-c2ccc(OC)cc2)cc1]

A solution of 2,3-bis(4-methoxyphenyl)quinoxaline-6-carbonitrile (200 mg, 0.51 mmol, 1.00 equiv, 93%) in N,N-dimethylformamide (7 mL), NaN3 (500 mg, 7.69 mmol, 15.18 equiv), and NH4Cl (147.9 mg, 2.79 mmol, 5.00 equiv)

was stirred for 4 h at 100° C. in an oil bath. The reaction was then quenched by the addition of water. The resulting solution was extracted with 8×50 mL of dichloromethane/MeOH (10:1) and the organic layers combined and dried over anhydrous sodium sulfate. The resulting solution was concentrated in vacuo, and washed with methanol, affording 47 mg (23%) of 2,3-bis(4-methoxyphenyl)-6-(1H-tetrazol-5-yl)quinoxaline as a yellow solid.

LC-MS (ES, m/z): 411 [M+H]+

$^1$H NMR (300 MHZ, d6-DMSO, ppm) δ 8.760 (1H, s), 8.463-8.293 (4H, m), 7.523, 7.498 (4H, d, J=7.5 Hz), 6.995, 6.971 (4H, d, J=7.2 Hz), 3.861 (6H, s)

Example 27

2,3-Bis(4-ethylphenyl)-6-(1H-tetrazol-5-yl)quinoxaline

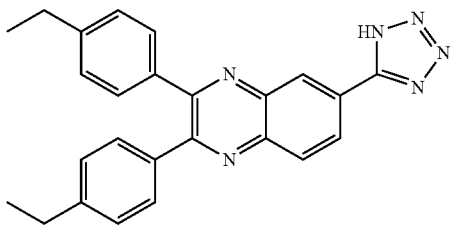 [SMILES: CCc1ccc(-c2nc3ccc(-c4nnn[nH]4)cc3nc2-c2ccc(CC)cc2)cc1]

A solution of 2,3-bis(4-ethylphenyl)quinoxaline-6-carbonitrile (200 mg, 0.55 mmol, 1.00 equiv) in N,N-dimethylformamide (6 mL), NaN$_3$ (179 mg, 2.75 mmol, 5.00 equiv), and NH$_4$Cl (146 mg, 2.75 mmol, 5.00 equiv) was stirred for 7 h at 100° C. in an oil bath. The reaction was then quenched by the addition of water. The resulting solution was extracted with 8×50 mL of dichloromethane and the organic layers combined and dried over anhydrous sodium sulfate. The resulting solution was concentrated in vacuo, and washed with methanol. This resulted in 98 mg (44%) of 2,3-bis(4-ethylphenyl)-6-(1H-tetrazol-5-yl)quinoxaline as a white solid.

LC-MS (ES, m/z): 407 [M+H]+

$^1$H-NMR (300 MHZ, d6-DMSO, ppm) δ 8.697 (1H, s), 8.520, 8.492 (1H, d, J=8.4 Hz), 8.235, 8.206 (1H, d, J=8.7 Hz), 7.6467-7.430 (4H, m), 7.245-7.219 (4H, t), 2.684-2.609 (4H, m), 1.227-1.178 (6H, t)

Example 28

3-(4-Fluorophenyl)-N-isopropyl-N-methyl-7-(2H-tetrazol-5-yl)quinoxalin-2-amine

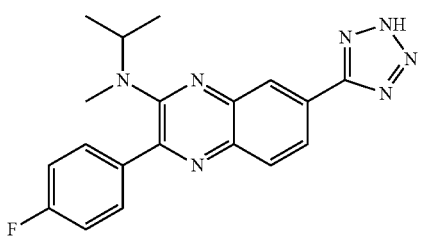 [SMILES: CC(C)N(C)c1nc2cc(-c3nn[nH]n3)ccc2nc1-c1ccc(F)cc1]

To a solution of 2-(4-fluorophenyl)-3-[methyl(propan-2-yl)amino]quinoxaline-6-carbonitrile (150 mg, 0.47 mmol) in DMSO (10.0 mL) and water (10.0 mL) was added NaN$_3$ (90 mg, 1.38 mmol) and ZnBr$_2$ (51.9 mg, 0.23 mmol), and the resulting mixture was stirred for 48 h at 130° C. in an oil bath. The reaction mixture was cooled down to room temperature, diluted with water (150 mL), extracted with dichloromethane (4×40 mL), and the organic layers combined, dried over magnesium sulfate, and concentrated in vacuo to give the residue, which was purified via silica gel column chromatography (2% dichloromethane in methanol) to afford 3-(4-fluorophenyl)-N-isopropyl-N-methyl-7-(2H-tetrazol-5-yl)quinoxalin-2-amine as a light yellow solid (60 mg, 35.0%).

LC/MS (ES, m/z): [M+H]$^+$ 364.1

$^1$H-NMR (300 MHz, DMSO) δ 8.42 (s, 1H), 8.04-8.13 (m, 2H), 7.89-7.94 (m, 2H), 7.35-7.41 (t, J=2.7 Hz, 2H), 4.18-4.21 (t, J=3.30 Hz, 1H), 2.68 (s, 3H), 1.05 (d, J=6.6 Hz, 6H)

Example 29

(S)-2-(4-Fluorophenyl)-3-(2-methylpyrrolidin-1-yl)-6-(2H-tetrazol-5-yl)quinoxaline

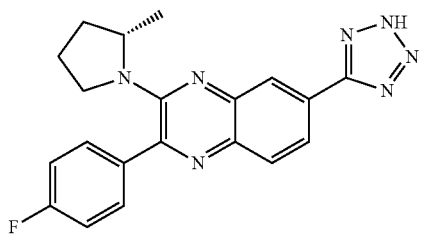 [SMILES: C[C@H]1CCCN1c1nc2cc(-c3nn[nH]n3)ccc2nc1-c1ccc(F)cc1]

Step 1. (S)—N-tert-Butyl-2-(4-fluorophenyl)-3-(2-methylpyrrolidin-1-yl)quinoxaline-6-carboxamide

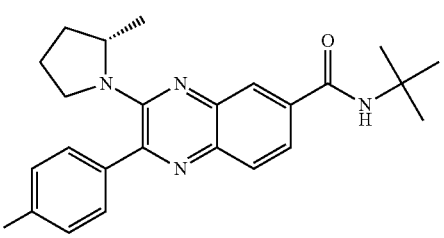

To a solution of (S)-2-(4-fluorophenyl)-3-(2-methylpyrrolidin-1-yl)quinoxaline-6-carboxylic acid (200 mg, 0.57 mmol) in dichloromethane (30 mL) was added 2-methylpropan-2-amine (46 mg, 0.63 mmol), triethylamine (115 mg, 1.14 mmol) and T$_3$P (217 mg, 0.68 mmol) dropwise with stifling. The resulting solution was stirred for 3 h at room temperature and then concentrated in vacuo to afford (S)—N-tert-butyl-2-(4-fluorophenyl)-3-(2-methylpyrrolidin-1-yl)quinoxaline-6-carboxamide as a yellow oil (160 mg, crude).

LC/MS (ES, m/z): [M+H]$^+$ 407.1

Step 2. (S)-2-(4-Fluorophenyl)-3-(2-methylpyrrolidin-1-yl)quinoxaline-6-carbonitrile

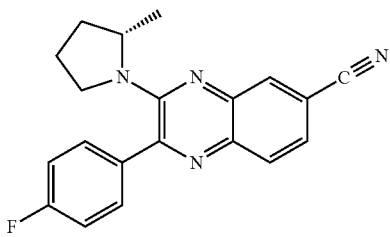 [SMILES: C[C@H]1CCCN1c1nc2cc(C#N)ccc2nc1-c1ccc(F)cc1]

To a solution of (S)—N-tert-butyl-2-(4-fluorophenyl)-3-(2-methylpyrrolidin-1-yl)quinoxaline-6-carboxamide (160 mg, crude) in dichloromethane (30 mL) was added TFAA (4 mL). The resulting solution was stirred overnight at room temperature and then quenched by the addition water (100 mL), adjusted to pH 7 with sodium bicarbonate, and extracted with dichloromethane (3×30 mL). The organic layers combined and dried over anhydrous sodium sulfate and concentrated in vacuo to (S)-2-(4-fluorophenyl)-3-(2-methylpyrrolidin-1-yl)quinoxaline-6-carbonitrile as a yellow solid (100 mg, 53%).

LC/MS (ES, m/z): [M+H]$^+$ 333.0

$^1$H-NMR (300 MHz, CDCl$_3$) δ 8.16 (d, J=1.5 Hz, 1H), 7.96-8.04 (m, 1H), 7.76-7.80 (m, 2H), 7.54-7.57 (m, 1H), 7.19-7.24 (m, 2H), 4.33-4.43 (m, 1H), 3.09-3.18 (m, 1H), 2.92-2.98 (m, 1H), 2.17-2.25 (m, 1H), 1.80-1.90 (m, 1H), 1.50-1.72 (m, 2H), 1.47 (d, J=6.9 Hz, 3H)

Step 3. (S)-2-(4-Fluorophenyl)-3-(2-methylpyrrolidin-1-yl)-6-(2H-tetrazol-5-yl)quinoxaline

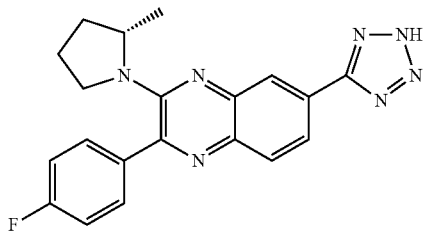 [SMILES: C[C@H]1CCCN1c1nc2cc(-c3nn[nH]n3)ccc2nc1-c1ccc(F)cc1]

To a solution of (S)-2-(4-fluorophenyl)-3-(2-methylpyrrolidin-1-yl)quinoxaline-6-carbonitrile (100 mg, 0.30 mmol) in DMSO (10 mL) was added dibromozinc (33.8 mg, 0.15 mmol), water (10 mL), azidosodium (48.8 mg, 0.75 mmol) and water (5 mL). The resulting solution was stirred for 1 days at 125° C. and then quenched by the addition of water (100 mL), extracted with dichloromethane (3×30 mL). The organic layers were combined and dried over anhydrous sodium sulfate and concentrated in vacuo to give a residue, which was purified via silica gel column chromatography (2% dichloromethane in methanol) to afford (S)-2-(4-fluorophenyl)-3-(2-methylpyrrolidin-1-yl)-6-(2H-tetrazol-5-yl)quinoxaline as a yellow solid (70.9 mg, 63%).

LC/MS (ES, m/z): [M+H]$^+$ 376.0

$^1$H-NMR (300 MHz, DMSO) δ 8.35 (d, J=1.8 Hz, 1H), 8.06-8.10 (m, 1H), 7.96-8.01 (t, J=8.4 Hz, 1H), 7.77-7.82 (m, 2H), 7.30-7.40 (m, 2H), 4.23-4.30 (m, 1H), 2.91-3.07 (m, 2H), 2.10-2.17 (m, 1H), 1.78-1.85 (m, 1H), 1.48-1.58 (m, 2H), 1.34 (d, J=6.0 Hz, 3H)

Example 30

(R)—N-sec-Butyl-3-(4-fluorophenyl)-N-methyl-7-(1H-tetrazol-5-yl)quinoxalin-2-amine

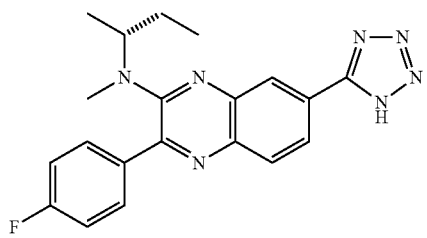 [SMILES: CC[C@@H](C)N(C)c1nc2cc(-c3nnn[nH]3)ccc2nc1-c1ccc(F)cc1]

Step 1. (R)—N-tert-Butyl-3-(sec-butyl(methyl)amino)-2-(4-fluorophenyl)quinoxaline-6-carboxamide

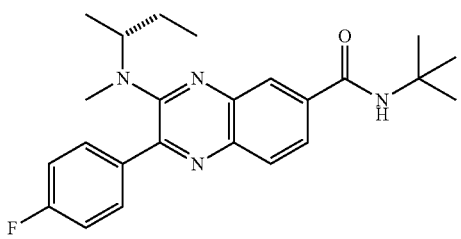 [SMILES: CC[C@@H](C)N(C)c1nc2cc(C(=O)NC(C)(C)C)ccc2nc1-c1ccc(F)cc1]

To a solution of (R)-3-(sec-butyl(methyl)amino)-2-(4-fluorophenyl)quinoxaline-6-carboxylic acid (500 mg, 1.42 mmol) in dichloromethane (30 mL) was added triethylamine (348 mg, 3.44 mmol), 2-methylpropan-2-amine (197 mg, 2.7 mmol), and T$_3$P (12 mL), and the reaction mixture was stirred overnight at room temperature. The resulting solution was diluted with water (150 mL) and extracted with dichloromethane (4×50 mL), the organic layers combined and dried over anhydrous magnesium sulfate and concentrated in vacuo to afford (R)—N-tert-butyl-3-(sec-butyl(methyl)amino)-2-(4-fluorophenyl)quinoxaline-6-carboxamide as a yellow solid (750 mg, crude).

Step 2. (R)-3-(sec-Butyl(methyl)amino)-2-(4-fluorophenyl)quinoxaline-6-carbonitrile

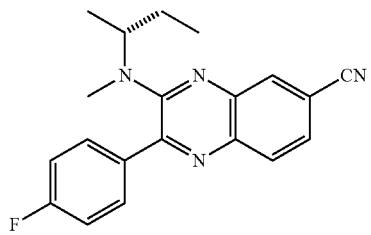 [SMILES: CC[C@@H](C)N(C)c1nc2cc(C#N)ccc2nc1-c1ccc(F)cc1]

To a solution of (R)—N-tert-butyl-3-(sec-butyl(methyl)amino)-2-(4-fluorophenyl)quinoxaline-6-carboxamide (750 mg, crude) in dichloromethane (30 mL) was added TFAA (5 mL), and the reaction mixture was stirred for 5 h at room temperature. The resulting solution was diluted with water (150 mL), extracted with ethyl acetate (3×50 mL), the organic layers combined and dried over anhydrous magnesium and concentrated in vacuo to give a residue, which was purified via silica gel column chromatography (2% ethyl acetate in petroleum ether) to afford (R)-3-(sec-butyl(methyl)amino)-2-(4-fluorophenyl)quinoxaline-6-carbonitrile as a yellow solid (400 mg, 84% 2 steps).

LC/MS (ES, m/z): [M+H]⁺ 335.0

¹H-NMR (300 MHz, DMSO): δ 8.21 (d, J=1.8 Hz, 1H), 7.99 (d, J=8.7 Hz, 1H), 7.83-7.88 (m, 2H), 7.74-7.77 (m, 1H), 7.37-7.43 (m, 2H), 3.94-4.01 (m, 1H), 2.73 (s, 3H), 1.36-1.59 (m, 2H), 1.02 (d, J=6.6 Hz, 1H), 0.61-0.66 (t, J=7.2 Hz, 3H)

Step 3. (R)—N-sec-Butyl-3-(4-fluorophenyl)-N-methyl-7-(1H-tetrazol-5-yl)quinoxalin-2-amine

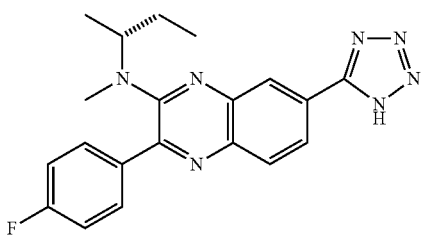 [SMILES: CC[C@@H](C)N(C)c1nc2cc(-c3nnn[nH]3)ccc2nc1-c1ccc(F)cc1]

To a solution of (R)-3-(sec-butyl(methyl)amino)-2-(4-fluorophenyl)quinoxaline-6-carbonitrile (170 mg, 0.51 mmol) in DMSO (25 mL) was added NaN₃ (101 mg, 1.55 mmol), ZnBr₂ (56 mg, 0.25 mmol) and water (3 mL) and the resulting mixture was stirred overnight at 130° C. The solution was diluted with water (200 mL) and adjusted to pH 4 with HCl (3N), extracted with ethyl acetate (5×50 mL), and the organic layers combined and dried over anhydrous magnesium and concentrated in vacuo to afford (R)—N-sec-butyl-3-(4-fluorophenyl)-N-methyl-7-(1H-tetrazol-5-yl)quinoxalin-2-amine as a yellow solid (72.3 mg, 37%).

LC/MS (ES, m/z): [M+H]⁺ 378.1

¹H-NMR (300 MHz, CDCl₃): δ 8.42 (d, J=1.5 Hz, 1H), 8.05-8.13 (m, 2H), 7.85-7.90 (m, 2H), 7.37-7.43 (m, 2H), 3.91-3.98 (m, 1H), 2.73 (s, 3H), 1.40-1.58 (m, 2H), 1.04 (d, J=6.3 Hz, 3H), 0.63-0.68 (t, J=7.2 Hz, 3H)

Example 31

3-(1H-Indazol-5-yl)-N-methyl-N-(propan-2-yl)-7-(1H-tetrazol-5-yl)quinoxalin-2-amine

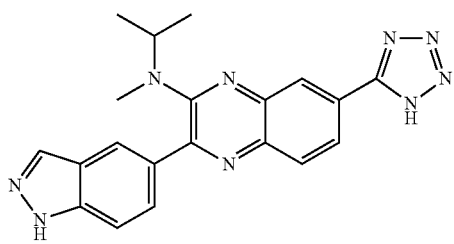

Step 1. Methyl 2-[1-[(tert-butoxy)carbonyl]-1H-indazol-5-yl]-3-[methyl(propan-2-yl)amino]quinoxaline-6-carboxylate

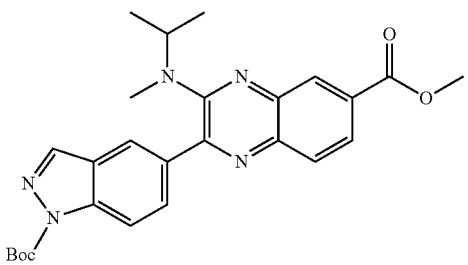 [SMILES: COC(=O)c1ccc2nc(-c3ccc4c(cnn4C(=O)OC(C)(C)C)c3)c(N(C)C(C)C)nc2c1]

To a solution of methyl 3-[methyl(propan-2-yl)amino]-2-[(trifluoromethane)sulfonyloxy]quinoxaline-6-carboxylate (800 mg, 1.96 mmol) in ethylene glycol dimethyl ether (20 ml) was added tert-butyl 5-(4,4,5,5-tetramethyl-1,3,2-dioxaborolan-2-yl)-1H-indazole-1-carboxylate (811 mg, 2.36 mmol), potassium carbonate (543 mg, 3.93 mmol), Pd(PPh₃)₄ (113 mg, 0.10 mmol), and water (4 ml), and the reaction mixture was stirred for 1 h at 90° C. in an oil bath. The reaction was then quenched by the addition of water (150 ml), extracted with dichloromethane (3×50 ml) and concentrated in vacuo to get a residue, which was purified via silica gel column chromatography (4% ethyl acetate in petroleum ether) to afford methyl 2-[1-[(tert-butoxy)carbonyl]-1H-indazol-5-yl]-3-[methyl(propan-2-yl)amino]quinoxaline-6-carboxylate as a yellow solid (624 mg, 67%).

LC/MS (ES, m/z): [M+H]+ 476.1

¹H-NMR (300 MHz, CDCl₃) δ 8.60 (d, J=1.5 Hz, 1H), 8.28-8.36 (m, 3H), 8.07-8.13 (m, 2H), 7.99-8.02 (m, 1H), 4.21-4.30 (m, 1H), 4.01 (s, 3H), 2.78 (s, 3H), 1.78 (s, 9H), 1.08 (d, J=6.6 Hz, 6H)

Step 2. Methyl 2-(1H-indazol-5-yl)-3-[methyl(propan-2-yl)amino]quinoxaline-6-carboxylate

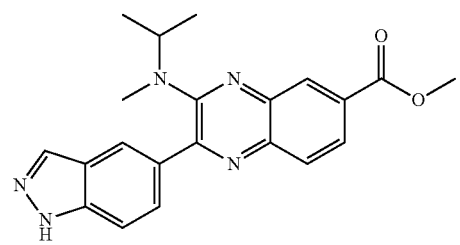 [SMILES: COC(=O)c1ccc2nc(-c3ccc4[nH]ncc4c3)c(N(C)C(C)C)nc2c1]

A solution of methyl 2-[1-[(tert-butoxy)carbonyl]-1H-indazol-5-yl]-3-[methyl(propan-2-yl)amino]quinoxaline-6-carboxylate (624 mg, 1.31 mmol) and trifluoroacetic acid (4 ml) in dichloromethane (20 ml) was stirred for 1 h at room temperature. The resulting solution was added water (200 ml) and adjusted to pH 8, extracted with dichloromethane (5×50 ml), dried over anhydrous magnesium and concentrated in vacuo to afford methyl 2-(1H-indazol-5-yl)-3-[methyl(propan-2-yl)amino]quinoxaline-6-carboxylate as a yellow solid (442 mg, crude).

LC/MS (ES, m/z): [M+H]⁺ 376.1

¹H-NMR (300 MHz, CDCl₃) δ 8.54 (d, J=1.8 Hz, 1H), 8.40 (s, 1H), 8.21 (s, 1H), 7.98-8.09 (m, 3H), 7.62 (d, J=8.7 Hz, 1H), 4.25-4.30 (m, 1H), 4.01 (s, 3H), 2.78 (s, 3H), 1.09 (d, J=6.6 Hz, 6H)

Step 3. 2-(1H-Indazol-5-yl)-3-[methyl(propan-2-yl) amino]quinoxaline-6-carboxylic acid

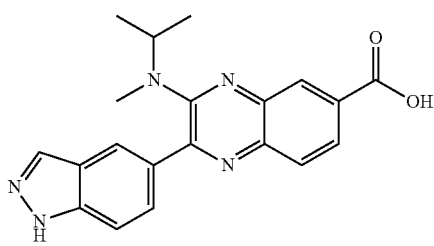 [SMILES: CC(C)N(C)c1nc2cc(C(=O)O)ccc2nc1-c1ccc2[nH]ncc2c1]

To a solution of methyl 2-(1H-indazol-5-yl)-3-[methyl (propan-2-yl)amino]quinoxaline-6-carboxylate (442 mg, crude) in methanol (30 ml) was added NaOH (226 mg, 5.65 mmol) in water (4 ml), and the resulting mixture was stirred for 2 days at room temperature. The resulting mixture was concentrated in vacuo to give a residue, which was dissolved in water (20 ml), and adjusted to pH 5 with HCl (2N). The product was collected by filtration to afford 2-(1H-indazol-5-yl)-3-[methyl(propan-2-yl)amino]quinoxaline-6-carboxylic acid as a yellow solid (330 mg, 94% 2 steps).

LC/MS (ES, m/z): [M+H]⁺ 362.1

¹H-NMR (300 MHz, CD₃OD) δ 8.46 (d, J=1.5 Hz, 1H), 8.36-8.37 (m, 1H), 8.20 (d, J=0.9 Hz, 1H), 8.04-8.07 (m, 1H), 7.93-7.97 (m, 2H), 7.70 (d, J=8.7 Hz, 1H), 4.22-4.26 (m, 1H), 2.81 (s, 3H), 1.06 (d, J=6.6 Hz, 6H)

Step 4. N-tert-Butyl-2-(1H-indazol-5-yl)-3-[methyl (propan-2-yl)amino]quinoxaline-6-carboxamide

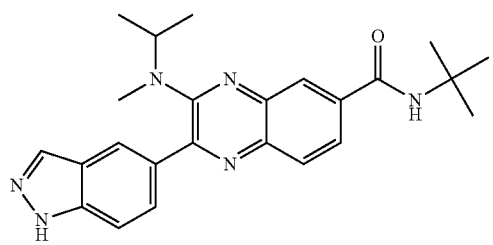 [SMILES: CC(C)N(C)c1nc2cc(C(=O)NC(C)(C)C)ccc2nc1-c1ccc2[nH]ncc2c1]

To a solution of 2-(1H-indazol-5-yl)-3-[methyl(propan-2-yl)amino]quinoxaline-6-carboxylic acid (200 mg, 0.55 mmol) in dichloromethane (30 ml) was added triethylamine (210 mg, 2.08 mmol), 2-methylpropan-2-amine (121 mg, 1.65 mmol), and T₃P (396 mg, 1.25 mmol), and the resulting mixture was stirred for 1 h at room temperature. The solution was diluted with water (150 ml), extracted with dichloromethane (3×50 ml), dried over anhydrous magnesium, and concentrated in vacuo to get N-tert-butyl-2-(1H-indazol-5-yl)-3-[methyl(propan-2-yl)amino]quinoxaline-6-carboxamide as a yellow solid (311 mg, crude).

Step 5. 2-(1H-Indazol-5-yl)-3-[methyl(propan-2-yl) amino]quinoxaline-6-carbonitrile

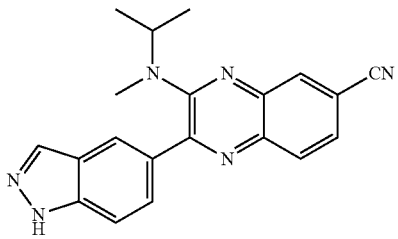 [SMILES: CC(C)N(C)c1nc2cc(C#N)ccc2nc1-c1ccc2[nH]ncc2c1]

To a solution of N-tert-butyl-2-(1H-indazol-5-yl)-3-[methyl(propan-2-yl)amino]quinoxaline-6-carboxamide (311 g, crude) in dichloromethane (40 ml) was added TFAA (8 ml) with stifling for 3 h at room temperature. The resulting solution was diluted with water (200 ml), extracted with dichloromethane (3×50 ml), and the organic layers combined and dried over anhydrous magnesium and concentrated in vacuo to get 2-(1H-indazol-5-yl)-3-[methyl(propan-2-yl)amino] quinoxaline-6-carbonitrile as a yellow solid (150 mg, 77% 2 steps).

LC/MS (ES, m/z): [M+H]⁺ 343.1

¹H-NMR (300 MHz, CDCl₃) δ 8.52 (d, J=8.4 Hz, 1H), 8.43 (d, J=0.6 Hz, 2H), 8.22-8.25 (m, 1H), 8.17 (d, J=1.5 Hz, 1H), 7.98-8.03 (m, 1H), 7.61-7.64 (m, 1H), 4.27-4.31 (m, 1H), 2.76 (s, 3H), 1.10 (d, J=6.6 Hz, 6H)

Step 6. 3-(1H-Indazol-5-yl)-N-methyl-N-(propan-2-yl)-7-(1H-tetrazol-5-yl)quinoxalin-2-amine

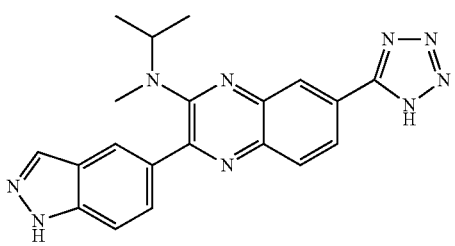 [SMILES: CC(C)N(C)c1nc2cc(-c3nnn[nH]3)ccc2nc1-c1ccc2[nH]ncc2c1]

To a solution of 2-(1H-indazol-5-yl)-3-[methyl(propan-2-yl)amino]quinoxaline-6-carbonitrile (150 mg, 0.44 mmol) in DMSO (15 ml) was added dibromozinc (50 mg, 0.22 mmol), azidosodium (86 mg, 1.32 mmol), and water (2 ml), and the resulting mixture was stirred overnight at 130° C. in an oil bath. The solution was diluted with water (200 ml) and adjusted to pH 4 with HCl (2N), extracted with ethyl acetate (5×50 ml), dried over anhydrous magnesium, and concentrated in vacuo to give a residue, which was purified by a silica gel column (10% methanol in dichloromethane) to afford 3-(1H-indazol-5-yl)-N-methyl-N-(propan-2-yl)-7-(1H-tetrazol-5-yl)quinoxalin-2-amine as a yellow solid (38.5 mg, 23%).

LC/MS (ES, m/z): [M+H]⁺ 386.1

¹H-NMR (300 MHz, CD₃OD) δ 8.47 (d, J=0.9 Hz, 1H), 8.35-8.36 (t, J=0.6 Hz, 1H), 8.21-8.25 (d, J=0.9 Hz, 1H), 8.06-8.13 (m, 2H), 7.94-7.97 (m, 1H), 7.71 (t, J=8.7 Hz, 1H), 4.27-4.36 (m, 1H), 2.82 (s, 3H), 1.09 (d, J=6.6 Hz, 6H)

Example 32

N-Isopropyl-N-methyl-3-(2-methyl-1H-indol-5-yl)-7-(1H-tetrazol-5-yl)quinoxalin-2-amine

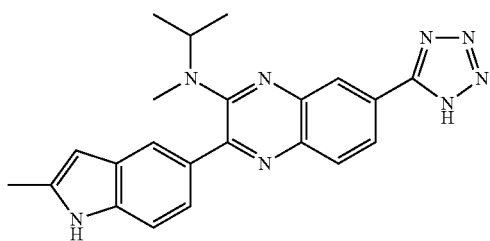 [SMILES: Cc1cc2cc(-c3nc4ccc(-c5nnn[nH]5)cc4nc3N(C)C(C)C)ccc2[nH]1]

Step 1. Methyl 3-[methyl(propan-2-yl)amino]-2-oxo-1,2-dihydroquinoxaline-6-carboxylate

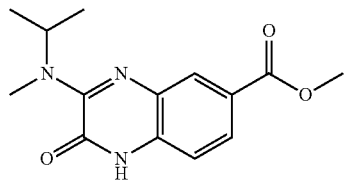

To a solution of methyl 3-chloro-2-oxo-1,2-dihydroquinoxaline-6-carboxylate (3 g, 12.57 mmol) in DMSO (20 ml) was added methyl(propan-2-yl)amine (1.3 g, 17.77 mmol), and DIEA (3.2 g, 24.76 mmol). The resulting solution was stirred overnight at 70° C. The product was precipitated by the addition of ice/water and collected by filtration to afford methyl 3-[methyl(propan-2-yl)amino]-2-oxo-1,2-dihydroquinoxaline-6-carboxylate as a yellow solid (2.5 g, 72%).

LC/MS (ES, m/z): [M+H]$^+$ 276.0

$^1$H-NMR (300 MHz, CDCl$_3$) δ 9.83 (s, 1H), 8.20 (d, J=1.5 Hz, 1H), 7.81-7.85 (m, 1H) 7.03 (d, J=8.4 Hz, 1H), 5.35-5.44 (m, 1H), 3.94 (s, 3H), 3.20 (s, 3H), 1.28 (d, J=6.6 Hz, 6H)

Step 2. 3-[Methyl(propan-2-yl)amino]-2-oxo-1,2-dihydroquinoxaline-6-carboxylic acid

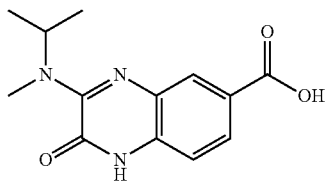 [SMILES: CC(C)N(C)c1nc2cc(C(=O)O)ccc2[nH]c1=O]

To a solution of methyl 3-[methyl(propan-2-yl)amino]-2-oxo-1,2-dihydroquinoxaline-6-carboxylate (2.5 g, 9.08 mmol) in methanol (20 ml) was added potassium hydroxide (2.5 g, 44.56 mmol) in water (5 ml). The resulting solution was stirred overnight at 50° C. and then concentrated in vacuo. The reaction was quenched water (100 ml). The pH was adjusted to 5 with HCl (3N). The product was precipitated from water and collected by filtration to afford 3-[methyl(propan-2-yl)amino]-2-oxo-1,2-dihydroquinoxaline-6-carboxylic acid as a white solid (2.1 g, 88%).

LC/MS (ES, m/z): [M+H]$^+$ 262.0

$^1$H-NMR (300 MHz, DMSO) δ 12.23 (s, 1H), 7.86 (s, 1H), 7.65-7.68 (m, 1H) 7.15 (d, J=8.4 Hz, 1H), 5.35-5.44 (m, 1H), 3.05 (s, 3H), 1.17 (d, J=6.6 Hz, 6H)

Step 3. N-tert-Butyl-3-[methyl(propan-2-yl)amino]-2-oxo-1,2-dihydroquinoxaline-6-carboxamide

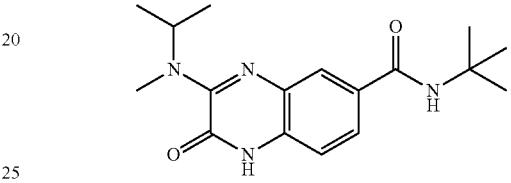

To a solution of 3-[methyl(propan-2-yl)amino]-2-oxo-1,2-dihydroquinoxaline-6-carboxylic acid (1 g, 3.83 mmol) in dichloromethane (50 ml) was added 2-methylpropan-2-amine (560 mg, 7.66 mmol), TEA (967 mg, 9.56 mmol), and T$_3$P (1.83 g, 7.66 mmol). The resulting solution was stirred overnight at room temperature and then concentrated in vacuo to afford N-tert-butyl-3-[methyl(propan-2-yl)amino]-2-oxo-1,2-dihydroquinoxaline-6-carboxamide as yellow oil (1.5 g, crude).

LC/MS (ES, m/z): [M+H]$^+$ 317.0

Step 4. 2-Chloro-3-[methyl(propan-2-yl)amino]quinoxaline-6-carbonitrile

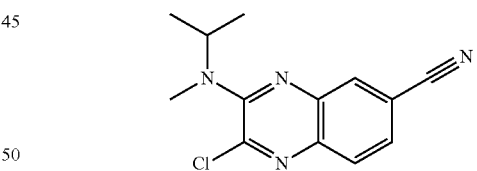

A solution of N-tert-butyl-3-[methyl(propan-2-yl)amino]-2-oxo-1,2-dihydroquinoxaline-6-carboxamide (1.5 g, crude) in POCl$_3$ (20 ml) was stirred overnight at reflux. The resulting mixture was concentrated in vacuo and quenched with ethyl acetate (50 ml) and ice/water (200 ml), the pH was adjusted to 6 with sodium bicarbonate solution. The resulting solution was extracted with ethyl acetate (3×100 ml), and the organic layers combined and dried over anhydrous magnesium sulfate and concentrated in vacuo to give a residue, which was purified via silica gel column chromatography (1%-2% ethyl acetate in petroleum ether) to afford 2-chloro-3-[methyl(propan-2-yl)amino]quinoxaline-6-carbonitrile as a yellow solid (0.25 g, 25% 2 steps).

LC/MS (ES, m/z): [M+H]$^+$ 261.0

Step 5. 3-[Methyl(propan-2-yl)amino]-2-(2-methyl-1H-indol-5-yl)quinoxaline-6-carbonitrile

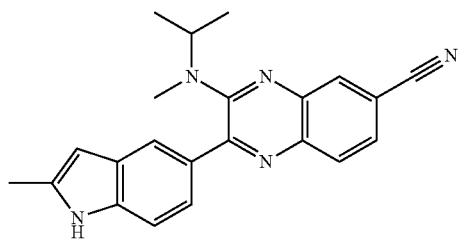 [SMILES: Cc1cc2cc(-c3nc4ccc(C#N)cc4nc3N(C)C(C)C)ccc2[nH]1]

To a solution of 2-chloro-3-[methyl(propan-2-yl)amino]quinoxaline-6-carbonitrile (250 mg, 0.96 mmol) in DME (8 ml) was added 2-methyl-5-(tetramethyl-1,3,2-dioxaborolan-2-yl)-1H-indole (494 mg, 1.92 mmol), potassium carbonate (265 mg, 1.92 mmol), Pd(PPh$_3$)$_4$ (58 mg, 0.05 mmol) and water (2 ml). The resulting solution was stirred for 1 h at 90° C. under an inert atmosphere of nitrogen. Then the mixture was quenched with water (100 ml) and extracted with ethyl acetate (3×50 ml), and the organic layers combined and dried over anhydrous magnesium sulfate. The filtrate was concentrated in vacuo to give a residue, which was purified via silica gel column chromatography (10%-20% ethyl acetate in petroleum ether) to afford 3-[methyl(propan-2-yl)amino]-2-(2-methyl-1H-indol-5-yl)quinoxaline-6-carbonitrile as a yellow solid (200 mg, 58%).

LC/MS (ES, m/z): [M+H]$^+$ 356.0

$^1$H-NMR (300 MHz, DMSO) δ 11.17 (s, 1H), 8.16 (s, 1H), 7.94-7.98 (t, J=1.5 Hz, 2H), 7.70-7.74 (m, 1H), 7.51-7.55 (m, 1H), 7.37 (d, J=8.4 Hz, 1H), 6.24 (s, 1H), 4.22-4.31 (m, 1H), 2.69 (s, 3H), 2.46 (s, 3H), 0.98 (d, J=6.6 Hz, 6H)

Step 6. N-Isopropyl-N-methyl-3-(2-methyl-1H-indol-5-yl)-7-(1H-tetrazol-5-yl)quinoxalin-2-amine

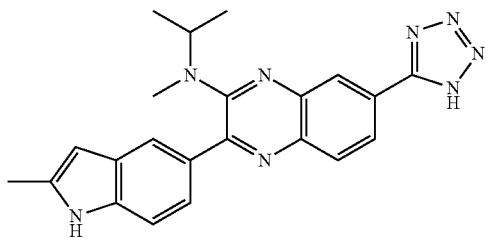 [SMILES: Cc1cc2cc(-c3nc4ccc(-c5nnn[nH]5)cc4nc3N(C)C(C)C)ccc2[nH]1]

To a solution of 3-[methyl(propan-2-yl)amino]-2-(2-methyl-1H-indol-5-yl)quinoxaline-6-carbonitrile (200 mg, 0.56 mmol) in DMSO (20 ml) was added NaN$_3$ (110 mg, 1.69 mmol) in water (2 ml), and ZnBr$_2$ (64 mg, 0.28 mmol). The resulting solution was stirred overnight at 130° C. and then quenched with water (200 ml). The pH was adjusted to 3 with HCl (2N). Then the solution was extracted with ethyl acetate (4×50 ml) and the organic layers combined, dried over anhydrous magnesium sulfate, and concentrated in vacuo to give a residue, which was purified by silica gel column chromatography (10%-15% dichloromethane in methanol) to afford N-isopropyl-N-methyl-3-(2-methyl-1H-indol-5-yl)-7-(1H-tetrazol-5-yl)quinoxalin-2-amine as an orange solid (47.4 mg, 21%).

LC/MS (ES, m/z): [M+H]$^+$ 399.1

$^1$H-NMR (300 MHz, DMSO) δ11.14 (s, 1H), 8.39 (d, J=1.5 Hz, 1H), 8.02-8.07 (m, 2H), 7.97 (s, 1H), 7.54-7.57 (m, 1H), 7.37 (d, J=8.4 Hz, 1H), 6.25 (s, 1H), 4.22-4.31 (m, 1H), 2.71 (s, 3H), 2.50 (s, 3H), 0.99 (d, J=6.6 Hz, 6H)

Example 33

3-(5-Fluorobenzofuran-2-yl)-N-methyl-N-(propan-2-yl)-7-(1H-tetrazol-5-yl)quinoxalin-2-amine

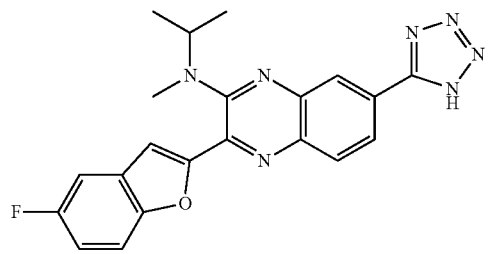 [SMILES: CC(C)N(C)c1nc2cc(-c3nnn[nH]3)ccc2nc1-c1cc2cc(F)ccc2o1]

Step 1. Methyl 2-(5-fluorobenzofuran-2-yl)-3-(isopropyl(methyl)amino)quinoxaline-6-carboxylate

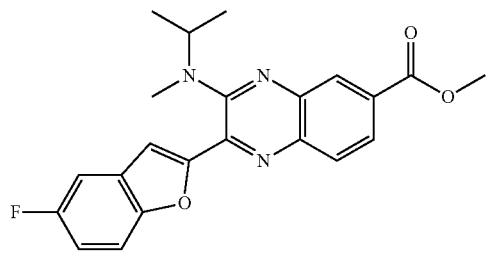 [SMILES: COC(=O)c1ccc2nc(-c3cc4cc(F)ccc4o3)c(N(C)C(C)C)nc2c1]

To a solution of 5-fluorobenzofuran-2-ylboronic acid (614.3 mg, 3.41 mmol) in dioxane (15 ml) was added ethyl 2-chloro-3-(isopropyl(methyl)amino)quinoxaline-6-carboxylate (500 mg, 1.70 mmol), K$_3$PO$_4$ (725 mg, 3.42 mmol), Pd(PPh$_3$)$_4$ (40.5 mg, 0.035 mmol) and water (1.0 ml), and the resulting mixture was stirred for 1 h at 90° C. in an oil bath under an inert atmosphere of nitrogen. The reaction mixture was concentrated in vacuo to give a residue, which was purified by silica gel column chromatography (1% ethyl acetate in petroleum ether) to afford methyl 2-(5-fluorobenzofuran-2-yl)-3-(isopropyl(methyl)amino)quinoxaline-6-carboxylate as a light yellow solid (536 mg, 80%).

LC/MS (ES, m/z): [M+H]$^+$ 394.0

$^1$H-NMR (300 MHz, CDCl$_3$): δ 8.61 (d, J=1.5 Hz, 1H), 8.05-8.14 (m, 2H), 7.57-7.62 (m, 2H), 7.37 (t, J=3.6 Hz, 1H), 7.11-7.18 (m, 1H), 4.29-4.38 (m, 1H), 4.01 (s, 3H), 2.94 (s, 3H), 1.21 (d, J=6.6 Hz, 6H)

Step 2. 2-(5-Fluorobenzofuran-2-yl)-3-(isopropyl(methyl)amino)quinoxaline-6-carboxylic acid

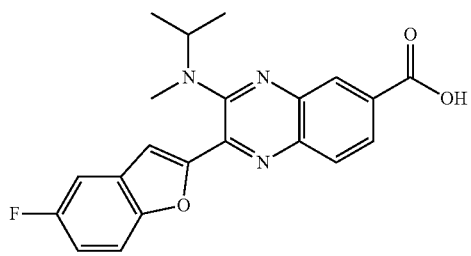 [SMILES: CC(C)N(C)c1nc2cc(C(=O)O)ccc2nc1-c1cc2cc(F)ccc2o1]

To a solution of methyl 2-(5-fluorobenzofuran-2-yl)-3-(isopropyl(methyl)amino)quinoxaline-6-carboxylate (560 mg, 1.42 mmol) in methanol (30 ml) was added sodium hydroxide (227.9 mg, 5.69 mmol) and water (2 ml) with stirring overnight at room temperature. The reaction mixture was concentrated in vacuo and dissolved in water (30 ml), adjusted to pH 5 with HCl (3N). The product was precipitated from water and collected by filtration to afford 2-(5-fluorobenzofuran-2-yl)-3-(isopropyl(methyl)amino)quinoxaline-6-carboxylic acid as a light yellow solid (486 mg, 90%).

LC/MS (ES, m/z): [M+H]$^+$ 380.1

$^1$H-NMR (300 MHz, DMSO): δ 13.28 (s, 1H), 8.27 (s, 1H), 7.96-8.03 (m, 2H), 7.77-7.82 (m, 1H), 7.59-7.64 (m, 1H), 7.26-7.34 (m, 1H), 4.15-4.24 (m, 1H), 3.33 (s, 3H), 1.16 (d, J=6.6 Hz, 6H)

Step 3. N-tert-Butyl-2-(5-fluorobenzofuran-2-yl)-3-[methyl(propan-2-yl)amino]quinoxaline-6-carboxamide

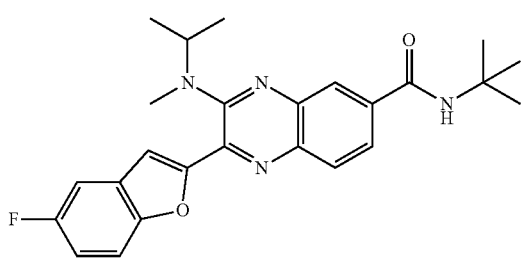 [SMILES: CC(C)N(C)c1nc2cc(C(=O)NC(C)(C)C)ccc2nc1-c1cc2cc(F)ccc2o1]

To a solution of 2-(5-fluorobenzofuran-2-yl)-3-[methyl(propan-2-yl)amino]quinoxaline-6-carboxylic acid (486 mg, 1.28 mmol) in dichloromethane (30 ml) was added triethylamine (366 mg, 3.62 mmol), 2-methylpropan-2-amine (212 mg, 2.90 mmol) and T$_3$P (610 mg, 1.92 mmol), and the resulting mixture was stirred for 1 h at room temperature. The reaction mixture was then quenched with water (120 ml), extracted with dichloromethane (4×60 ml), and the organic layers combined and concentrated in vacuo to afford N-tert-butyl-2-(5-fluorobenzofuran-2-yl)-3-[methyl(propan-2-yl)amino]quinoxaline-6-carboxamide as a yellow solid (600 mg, crude), which was used to the next step without further purification.

LC/MS (ES, m/z): [M+H]$^+$ 435.1

Step 4. 2-(5-Fluorobenzofuran-2-yl)-3-[methyl(propan-2-yl)amino]quinoxaline-6-carbonitrile

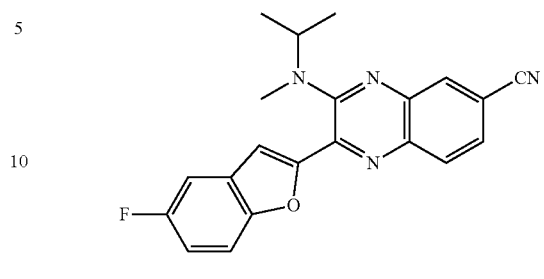

To a solution of N-tert-butyl-2-(5-fluorobenzofuran-2-yl)-3-[methyl(propan-2-yl)amino]quinoxaline-6-carboxamide (600 mg, crude) in dichloromethane (30 ml) was added TFAA (3 ml) with stifling overnight at room temperature. The reaction mixture was quenched with water (80 ml) and adjusted to pH 8 with sodium bicarbonate solution, extracted with dichloromethane (4×50 ml), and the organic layers combined and concentrated in vacuo to give the residue, which was purified by silica gel column chromatography (1% ethyl acetate in petroleum ether) to afford 2-(5-fluorobenzofuran-2-yl)-3-[methyl(propan-2-yl)amino]quinoxaline-6-carbonitrile as a yellow solid (400 mg, 80%).

LC/MS (ES, m/z): [M+H]$^+$ 361.0

$^1$H-NMR (300 MHz, DMSO): δ 8.19 (d, J=1.5 Hz, 1H), 8.06 (m, J=8.4 Hz, 2H), 7.56-7.65 (m, 3H), 7.34-7.38 (m, 1H), 7.12-7.19 (m, 1H), 4.34-4.42 (m, 1H), 2.92 (s, 3H), 1.24 (d, J=6.6 Hz, 6H)

Step 5. 3-(5-Fluorobenzofuran-2-yl)-N-methyl-N-(propan-2-yl)-7-(1H-tetrazol-5-yl)quinoxalin-2-amine

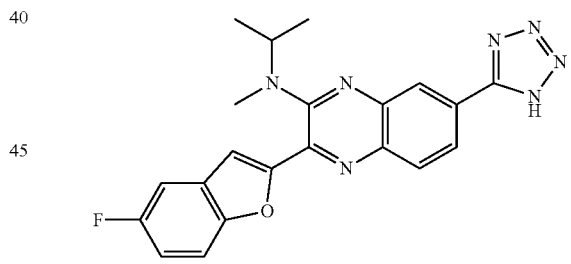

To a solution of 2-(5-fluorobenzofuran-2-yl)-3-[methyl(propan-2-yl)amino]quinoxaline-6-carbonitrile (150 mg, 0.42 mmol) in DMSO (30 ml) and water (2 ml) was added ZnBr$_2$ (46.9 mg, 0.21 mmol) and NaN$_3$ (81.3 mg, 1.25 mmol), and the resulting mixture was stirred for 48 h at 130° C. The reaction mixture was quenched with water (100 ml) and adjusted to pH 3 with HCl (2N), extracted with ethyl acetate (4×60 ml), and the organic layers combined and concentrated in vacuo to give the residue, which was purified by silica gel column chromatography (12% methanol in dichloromethane) to afford 3-(5-fluorobenzofuran-2-yl)-N-methyl-N-(propan-2-yl)-7-(1H-tetrazol-5-yl)quinoxalin-2-amine as a yellow solid (62.6 mg, 37%).

LC/MS (ES, m/z): [M+H]$^+$ 404.1

$^1$H-NMR (300 MHz, DMSO): δ 8.32 (d, J=1.5 Hz, 1H), 8.20-8.23 (m, 1H), 7.95 (d, J=8.4 Hz, 1H), 7.77-7.81 (m, 1H), 7.59-7.62 (m, 2H), 7.25-7.31 (m, 1H), 4.13-4.17 (t, J=6.3 Hz, 1H), 2.84 (s, 3H), 1.16 (d, J=6.6 Hz, 6H)

Example 34

N-(2,3-Bis(4-methoxyphenyl)quinoxalin-6-yl)methanesulfonamide

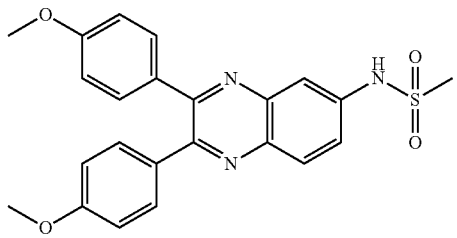

Step 1. N-(2,3-Bis(4-methoxyphenyl)quinoxalin-6-yl)-N-(methylsulfonyl)methanesulfonamide

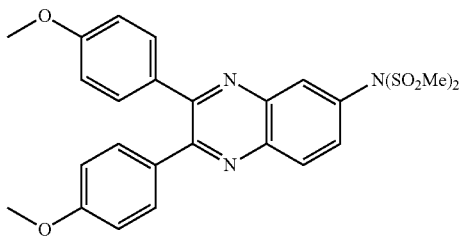

To a solution of 2,3-bis(4-methoxyphenyl)quinoxalin-6-amine (123.2 mg, 0.35 mmol, 1.00 equiv) in dichloromethane (20 mL) was added methanesulfonyl chloride (47.2 mg, 0.41 mmol, 1.20 equiv) and triethylamine (174.3 mg, 1.73 mmol, 5.00 equiv). The resulting solution was stirred for 1.5 h at room temperature. The resulting mixture was concentrated in vacuo, resulting in 179.55 mg (81%) of N-(2,3-bis(4-methoxyphenyl)quinoxalin-6-yl)-N-(methylsulfonyl)methanesulfonamide as a brown solid.

LC-MS: (ES, m/z): 514 [M+H]$^+$

Step 2. N-(2,3-Bis(4-methoxyphenyl)quinoxalin-6-yl)methanesulfonamide

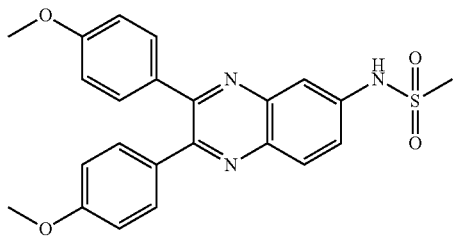

To a solution of N-(2,3-bis(4-methoxyphenyl)quinoxalin-6-yl)-N-(methylsulfonyl)methanesulfonamide (143.64 mg, 0.28 mmol, 1.00 equiv, 90%) in tetrahydrofuran/MeOH (1:1, 10 mL) was added LiOH H$_2$O (58.5 mg, 1.39 mmol, 5.00 equiv). This was followed by the dropwise addition of a solution of sodium hydroxide (56 mg, 1.40 mmol, 5.00 equiv) in water (2 mL). The resulting solution was stirred for 1 h at 35° C. in an oil bath. The pH was adjusted to 7-8 with 1N HCl. The resulting mixture was concentrated in vacuo and washed with methanol, resulting in 46.5 mg (37%) of N-(2,3-bis(4-methoxyphenyl)quinoxalin-6-yl)methanesulfonamide as a yellow solid.

LC-MS: (ES, m/z): 436 [M+H]$^+$ $^1$H-NMR (300 MHZ, CDCl$_3$, ppm): δ 8.169, 8.139 (1H, d, J=9 Hz), 8.034 (1H, s), 7.664, 7.634 (1H, d, J=9 Hz), 7.543-7.487 (4H, t), 6.917, 6.890 (4H, d, J=8.1 Hz), 3.861 (6H, s), 3.180 (3H, s)

Example 35

2,3-Bis(4-methoxyphenyl)quinoxaline-6-sulfonamide

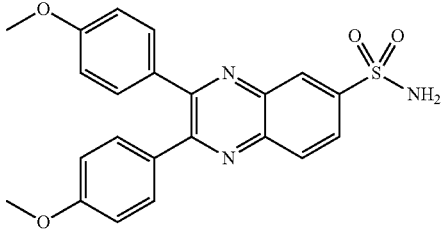 [SMILES: COc1ccc(-c2nc3ccc(S(N)(=O)=O)cc3nc2-c2ccc(OC)cc2)cc1]

Step 1. 3,4-Diaminobenzenesulfonic acid

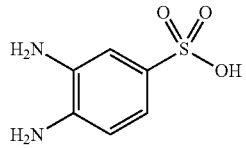

To concentrated sulfuric acid (200 mL) at −40° C. was added benzene-1,2-diamine (20 g, 184.95 mmol, 1.00 equiv). The resulting solution was stirred for 30 min at room temperature. Then the resulting solution was stirred overnight at 140° C. in an oil bath. The reaction mixture was cooled to room temperature, quenched by the addition of 500 g of ice, and the solids collected by filtration. The crude product was purified by recrystallization from water, resulting in 9.8 g (28%) of 3,4-diaminobenzenesulfonic acid as a white solid.

Step 2.
2,3-Bis-(4-methoxyphenyl)quinoxaline-6-sulfonic acid

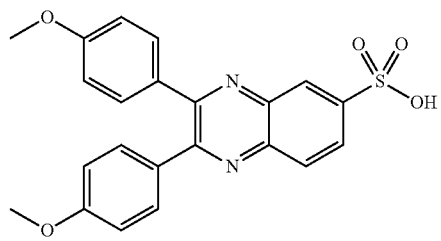 [SMILES: COc1ccc(-c2nc3ccc(S(=O)(=O)O)cc3nc2-c2ccc(OC)cc2)cc1]

A solution of 1,2-bis(4-methoxyphenyl)ethane-1,2-dione (400 mg, 1.48 mmol, 1.00 equiv) and 3,4-diaminobenzenesulfonic acid (278 mg, 1.48 mmol, 1.00 equiv) in ethanol/water (1:1, 20 mL) was stirred overnight at reflux in an oil bath. The resulting mixture was concentrated in vacuo, resulting in 500 mg (80%) of 2,3-bis-(4-methoxyphenyl)quinoxaline-6-sulfonic acid as a brown solid.

Step 3.
2,3-Bis(4-methoxyphenyl)quinoxaline-6-sulfonamide

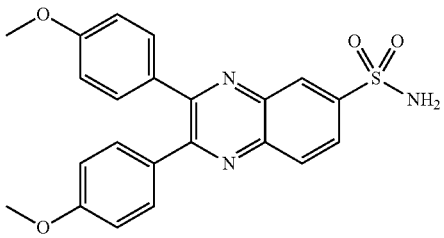 [SMILES: COc1ccc(-c2nc3ccc(S(N)(=O)=O)cc3nc2-c2ccc(OC)cc2)cc1]

To a solution of 2,3-bis(4-methoxyphenyl)quinoxaline-6-sulfonic acid (137.2 mg, 0.33 mmol, 1.00 equiv) in thionyl chloride (12 mL) was added N,N-dimethylformamide (2 mL) dropwise with stifling. The mixture was stirred at reflux for 3 hr in an oil bath. The resulting mixture was concentrated in vacuo. The residue was dissolved in acetonitrile (10 mL) and added to a solution of ammonia (2 g) in acetonitrile (10 mL) dropwise at 0° C. The resulting mixture was stirred overnight at room temperature, then concentrated in vacuo. The crude product (100 mg) was purified by Prep-HPLC with the following conditions (AGILENT Pre-HPLC (UV-Directed)): Column, SunFire Prep C18, 5 um, 19*100 mm; mobile phase, water with 0.05% TFA and $CH_3CN$ (10% $CH_3CN$ up to 65% in 2.8 min, hold 65% in 2.5 min, up to 100% in 0.1 min, hold 100% in 0.6 min, down to 10% in 0.1 min); Detector, UV 254 nm. This resulted in 16 mg (12%) of 2,3-bis(4-methoxyphenyl)quinoxaline-6-sulfonamide as a light yellow solid.

LC-MS: (ES, m/z): 422 $[M+H]^+$ $^1$H-NMR (300 MHz, d-DMSO, ppm): 8.482-8.476 (d, J=1.8 Hz, 1H), 8.298-8.269 (d, J=8.7 Hz, 1H), 8.174-8.138 (m, 1H), 7.698 (s, 2H), 7.518-7.489 (d, J=8.7 Hz, 4H), 6.988-6.961 (d, J=8.1 Hz, 4H), 3.805 (s, 3H)

Example 36

2,3-Bis(4-methoxyphenyl)-N-methylquinoxaline-6-sulfonamide

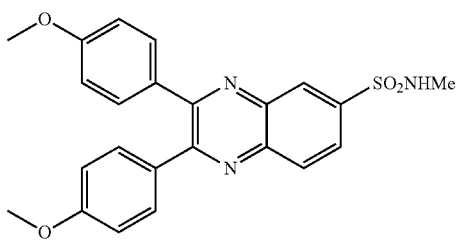

A solution of 2,3-bis(4-methoxyphenyl)quinoxaline-6-sulfonic acid (200 mg, 0.47 mmol, 1.00 equiv) in thionyl chloride (20 mL) was heated to reflux for 3 h in an oil bath. The resulting solution was concentrated in vacuo and the residue was diluted by 10 ml of dichloromethane. Then the resulting solution was added dropwise to a solution of $MeNH_2 \cdot HCl$ (318 mg, 4.75 mmol, 10.00 equiv) and DIEA (917 mg, 7.11 mmol, 15.00 equiv) in dichloromethane (20 mL) at 0° C., and then stirred overnight at room temperature, concentrated in vacuo, and purified by Prep-HPLC with the following conditions (AGILENT Pre-HPLC (UV-Directed)): Column, SunFire Prep C18, 5 um, 19*100 mm; mobile phase, water with 0.05% TFA and $CH_3CN$ (10% $CH_3CN$ up to 75% in 2.8 min, hold 75% in 2.2 min, up to 100% in 0.1 min, hold 100% in 0.5 min, down to 10% in 0.1 min); Detector, UV 254 nm. This resulted in 100 mg (49%) of 2,3-bis(4-methoxyphenyl)-N-methylquinoxaline-6-sulfonamide as a yellow solid.

LC-MS: (ES, m/z): 436 $[M+H]^+$ $^1$H NMR (300 MHz, d-DMSO, ppm): 8.439-8.433 (s, 1H), 8.324-8.295 (d, J=8.7 Hz, 1H), 8.110-8.074 (m, 1H), 7.815-7.767 (m, 1H), 7.517-7.488 (d, J=8.7 Hz, 2H), 6.988-6.958 (d, J=9 Hz, 4H), 3.805 (s, 6H), 3.333-3.311 (s, 3H)

Example 37

4-(2,3-Bis(4-methoxyphenyl)quinoxalin-6-ylsulfonyl)morpholine

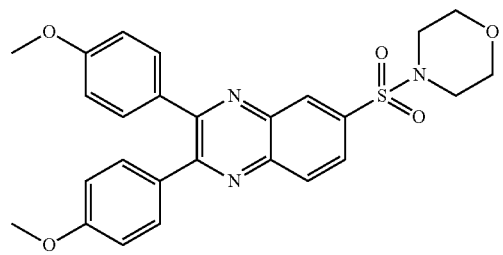 [SMILES: COc1ccc(-c2nc3ccc(S(=O)(=O)N4CCOCC4)cc3nc2-c2ccc(OC)cc2)cc1]

A solution of 2,3-bis(4-methoxyphenyl)quinoxaline-6-sulfonic acid (350 mg, 0.83 mmol, 1.00 equiv), thionyl chloride (1.0 g, 8.40 mmol, 10.00 equiv), N,N-dimethylformamide (60 mg, 0.82 mmol, 1.00 equiv) and toluene (10 mL) was heated to reflux for 3 h in an oil bath. The resulting mixture was concentrated in vacuo and diluted with 10 ml of dichloromethane. Then the resulting mixture was added into a solution of morpholine (1.44 g, 16.53 mmol, 20.00 equiv) in dichloromethane (10 mL) at 0° C. The reaction mixture was stirred overnight at room temperature, concentrated in vacuo, and purified by Prep-HPLC with the following conditions (AGILENT Pre-HPLC (UV-Directed)): Column, SunFire Prep C18, 5 um, 19*100 mm; mobile phase, water with 0.05% TFA and $CH_3CN$ (10% $CH_3CN$ up to 80% in 3 min, hold 80% in 2 min, up to 100% in 0.1 min, hold 100% in 0.9 min); Detector, UV 254 nm. This resulted in 60 mg (34%) of 4-(2,3-bis(4-methoxyphenyl)quinoxalin-6-ylsulfonyl)morpholine as a white solid.

LC-MS: (ES, m/z):492 $[M+H]^+$ $^1$H-NMR (300 MHz, d-DMSO, ppm): 8.412-0.406 (s, 1H), 8.355-0.325 (d, J=9 Hz, 1H), 8.069-0.033 (d, J=10.8 Hz, 1H), 7.534-0.505 (d, J=8.7 Hz, 4H), 6.995-6.968 (d, J=8.1 Hz, 4H), 3.809 (s, 6H), 3.659 (m, 4H), 3.019 (m, 4H)

Example 38

2,3-Bis(4-methoxyphenyl)quinoxaline-6-sulfonic acid

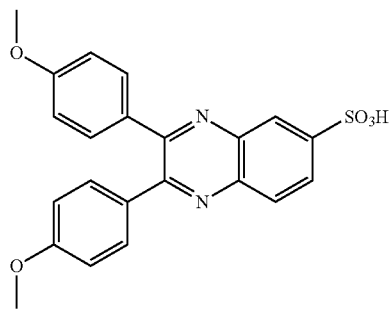 [SMILES: COc1ccc(-c2nc3ccc(S(=O)(=O)O)cc3nc2-c2ccc(OC)cc2)cc1]

Step 1. 3,4-Diaminobenzenesulfonic acid

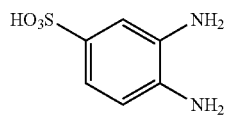 [SMILES: Nc1ccc(S(=O)(=O)O)cc1N]

The solution of benzene-1,2-diamine (5 g, 46.24 mmol) in sulfuric acid (conc, 80 mL) was stirred for 30 min at room temperature and then heated to 140° C. overnight. The reaction mixture was cooled to room temperature and quenched by the addition of ice-water (200 mL). The product was precipitated from water to afford 3,4-diaminobenzene-1-sulfonic acid as a white solid (4.3 g, 49%).

LC/MS (ES, m/z): [M+H]$^+$ 189.0
$^1$H-NMR (300 MHz, d6-DMSO) δ 7.38 (d, J=1.8 Hz, 1H), 7.18 (d, J=8.4 Hz, 1H), 6.84 (d, J=8.4 Hz, 1H)

Step 2. 1,2-Bis(4-methoxyphenyl)ethanone

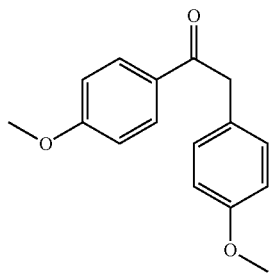

A solution of 2-(4-methoxyphenyl)acetic acid (5.0 g, 30.12 mmol) in thionyl chloride (50 mL) was stirred for 3 hr at reflux and then concentrated in vacuo to give a residue, which was dissolved in dichloromethane (10 mL) and then added dropwise to a solution of anisole (6.51 g, 60.28 mmol) and AlCl$_3$ (11.97 g, 90.00 mmol) in dichloromethane (120 mL). The resulting solution was stirred for 3 h at room temperature, then diluted with water (100 mL), extracted with dichloromethane (3×80 mL), dried over magnesium sulfate, and concentrated in vacuo to give a residue, which was purified by silica gel column chromatography with (1%~2% ethyl acetate in petroleum ether) to afford 1,2-bis(4-methoxyphenyl)ethanone as a white solid (6.5 g, 84%).

(ES, m/z): [M+H]$^+$ 257.0
$^1$H-NMR (300 MHz, CDCl$_3$) δ 7.99-8.03 (m, 2H), 7.18-7.23 (m, 2H), 6.84-6.97 (m, 4H), 4.17 (d, J=6.0 Hz, 2H), 3.90 (s, 3H), 3.80 (s, 3H)

Step 3. 1,2-Bis(4-methoxyphenyl)ethane-1,2-dione

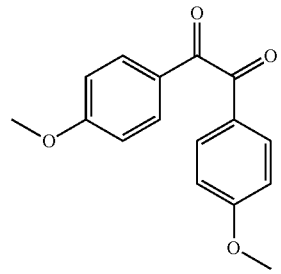 [SMILES: COc1ccc(C(=O)C(=O)c2ccc(OC)cc2)cc1]

To a solution of 1,2-bis(4-methoxyphenyl)ethan-1-one (1 g, 3.90 mmol) in DMSO (20 mL) was added SeO$_2$ (1.76 g, 15.86 mmol) in several batches at 100° C. over 30 min, and then stirred for 3 hr at this temperature. The reaction was quenched by the addition of water (200 mL) and extracted with dichloromethane (3×50 mL), dried over magnesium sulfate and concentrated in vacuo to give a residue, which was purified by silica gel column chromatography (1%~10% ethyl acetate in petroleum ether) to afford 1,2-bis(4-methoxyphenyl)ethane-1,2-dione as a brown solid (600 mg, 76%).

(ES, m/z): [M+H]$^+$ 270.0
$^1$H-NMR (300 MHz, CDCl$_3$) δ 7.94-7.99 (m, 4H), 6.96-7.02 (m, 4H), 3.90 (s, 6H)

Step 4.
2,3-Bis(4-methoxyphenyl)quinoxaline-6-sulfonic acid

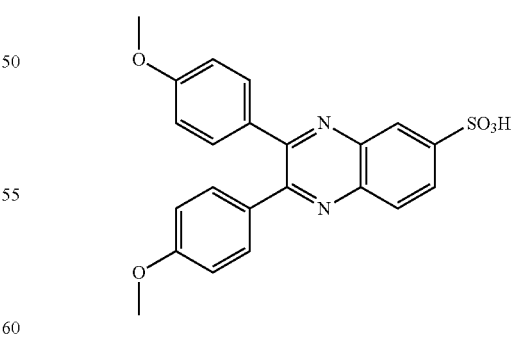

To a solution of 1,2-bis(4-methoxyphenyl)ethane-1,2-dione (200 mg, 0.74 mmol) in ethanol (3 mL) and water (3 mL) was added 3,4-diaminobenzene-1-sulfonic acid (116 mg, 0.62 mmol). The resulting solution was stirred overnight at 100° C. in an oil bath, and then quenched by the addition of water (60 mL), extracted with dichloromethane (3×20 mL), dried over anhydrous magnesium sulfate and concentrated in vacuo to afford 2,3-bis(4-methoxyphenyl)quinoxaline-6-sulfonic acid (95.3 mg, 30.4%).

(ES, m/z): [M+H]+ 423.0

1H-NMR (300 MHz, DMSO) δ 8.21 (d, J=1.50 Hz, 1H), 7.87-8.06 (m, 2H), 7.45-7.48 (m, 4H), 6.93-7.00 (m, 4H), 3.74 (s, 6H)

The following compounds can generally be made using the methods known in the art and described above. It is expected that these compounds when made will have activity similar to those that have been made in the examples above.

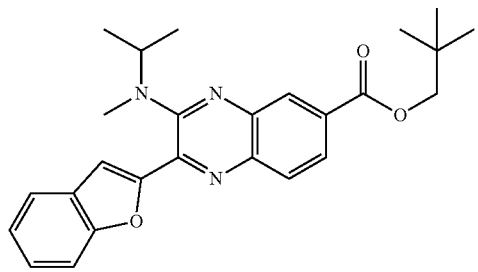

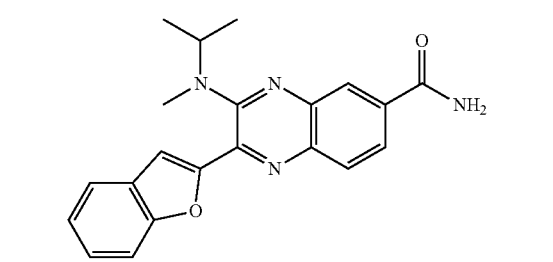

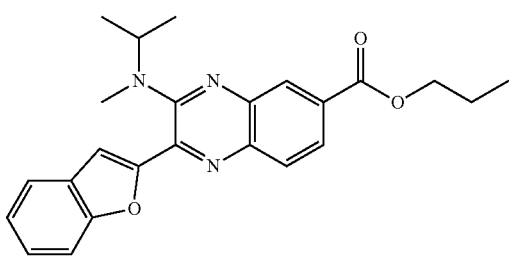

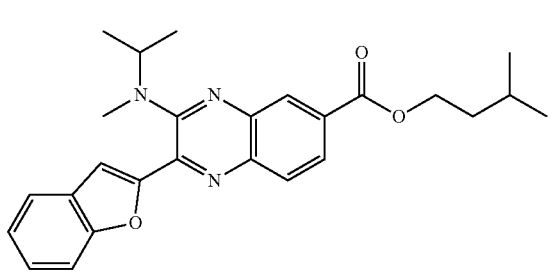

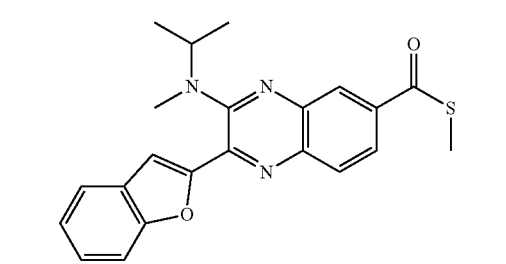

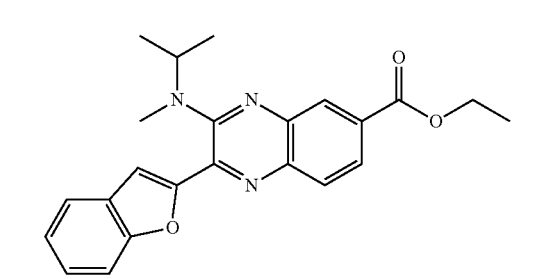

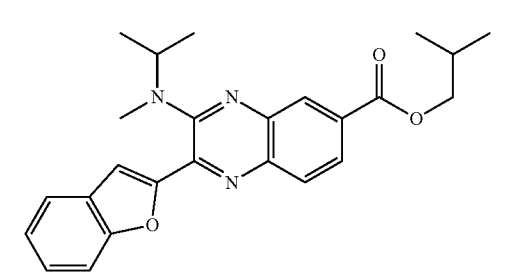

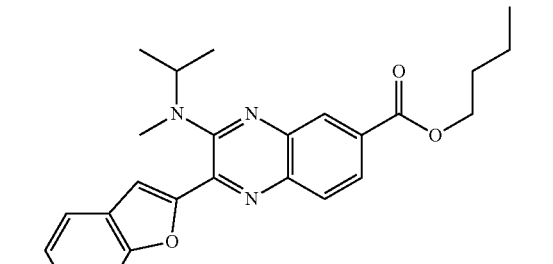

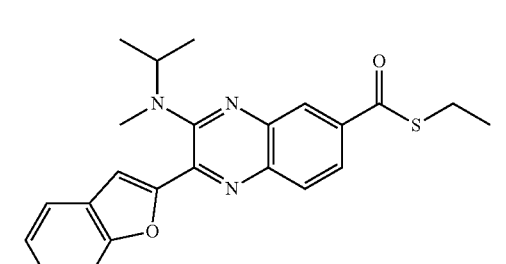

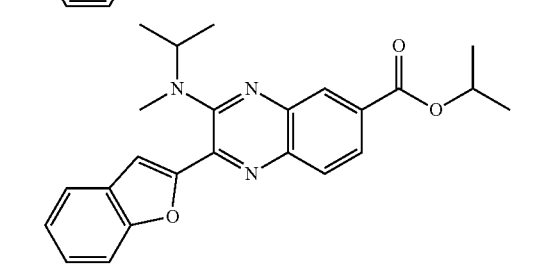

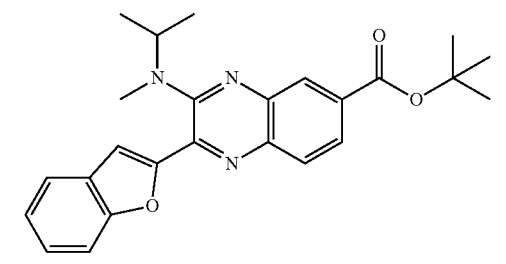

81
-continued
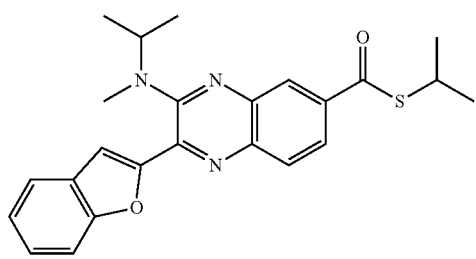
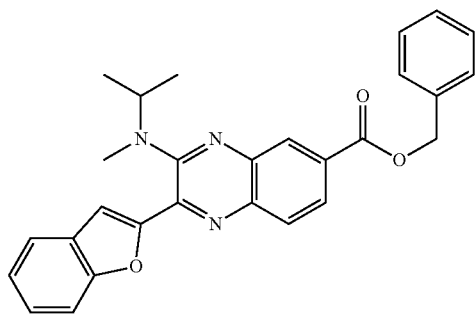
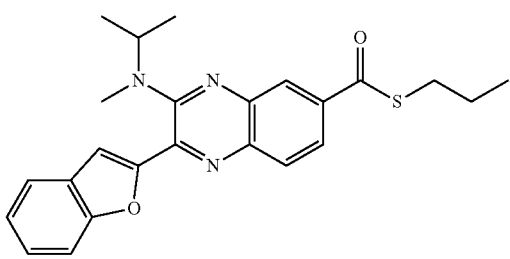
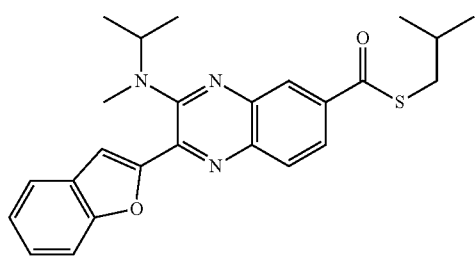
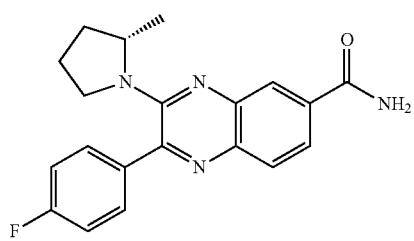
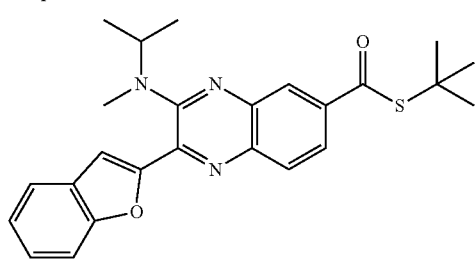
82
-continued
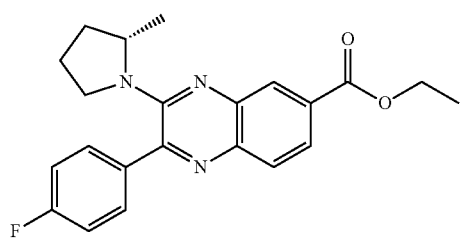
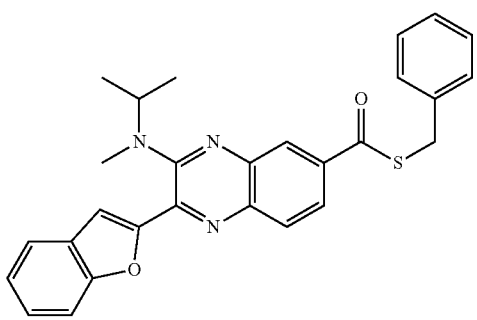
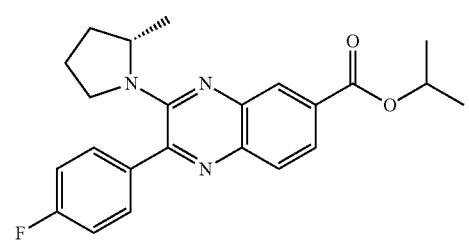
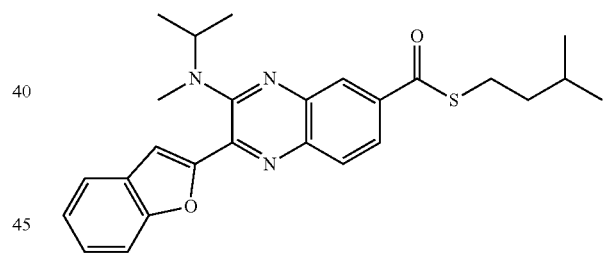
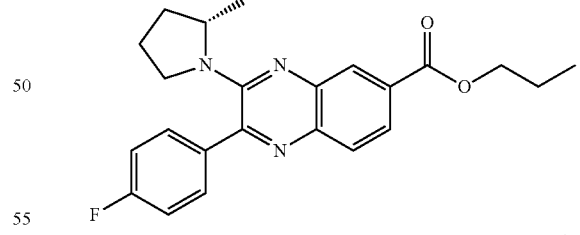
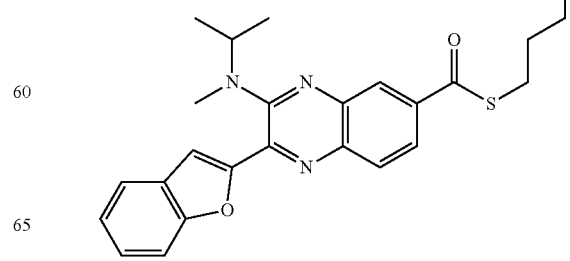

83
-continued
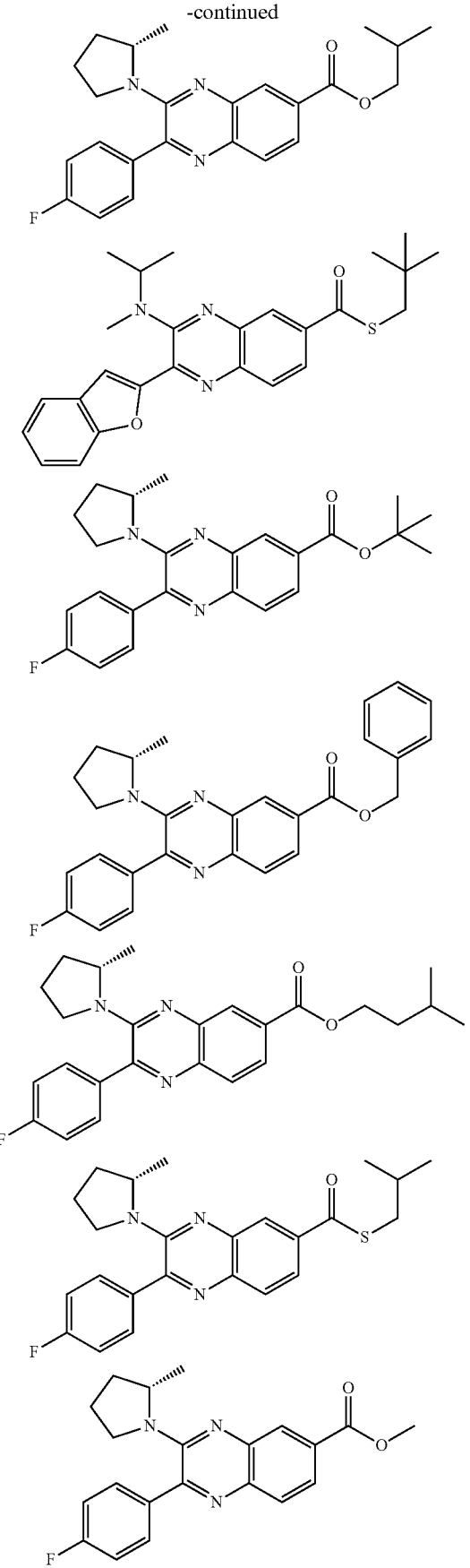
84
-continued
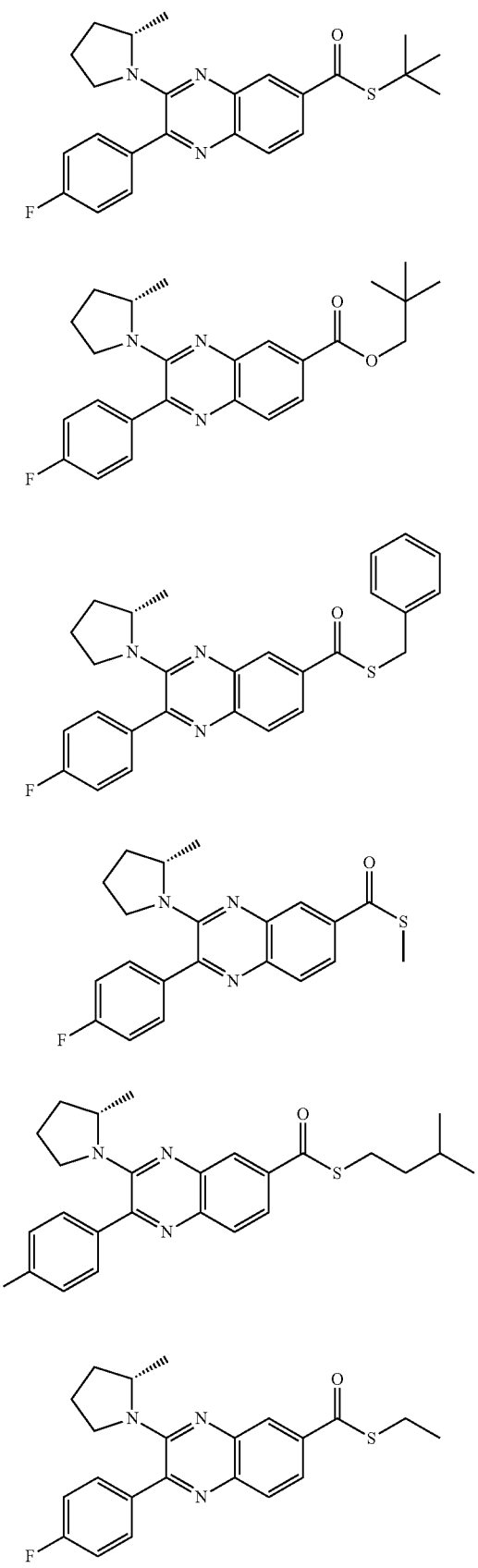

85
-continued
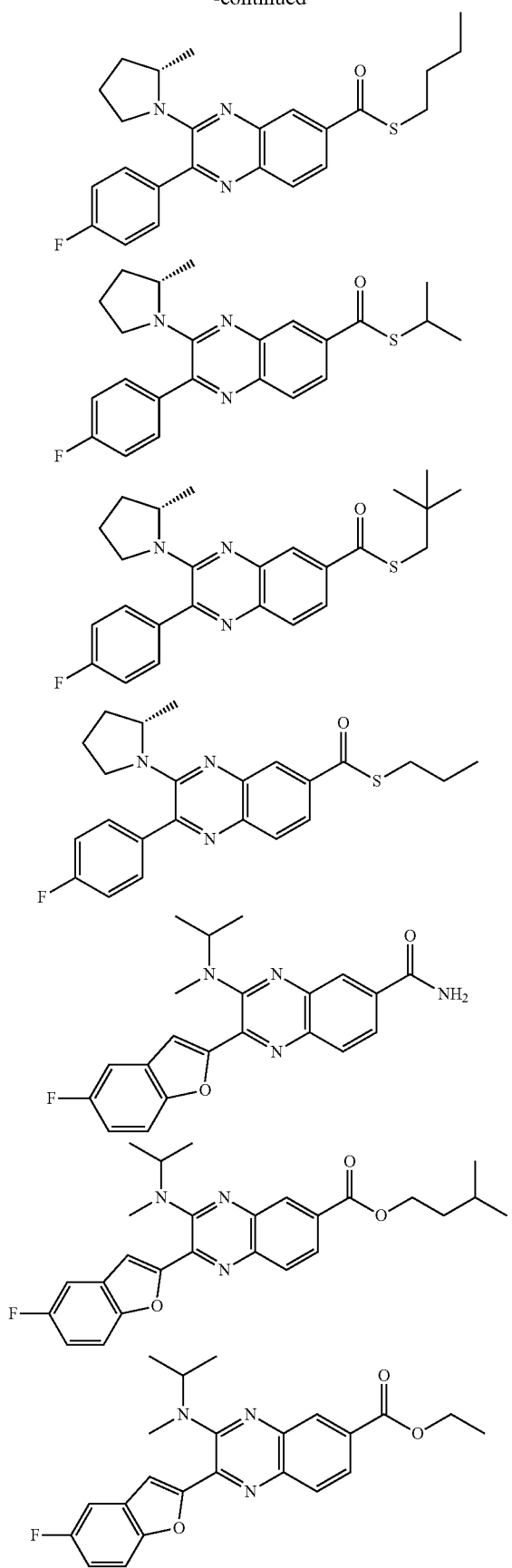
86
-continued
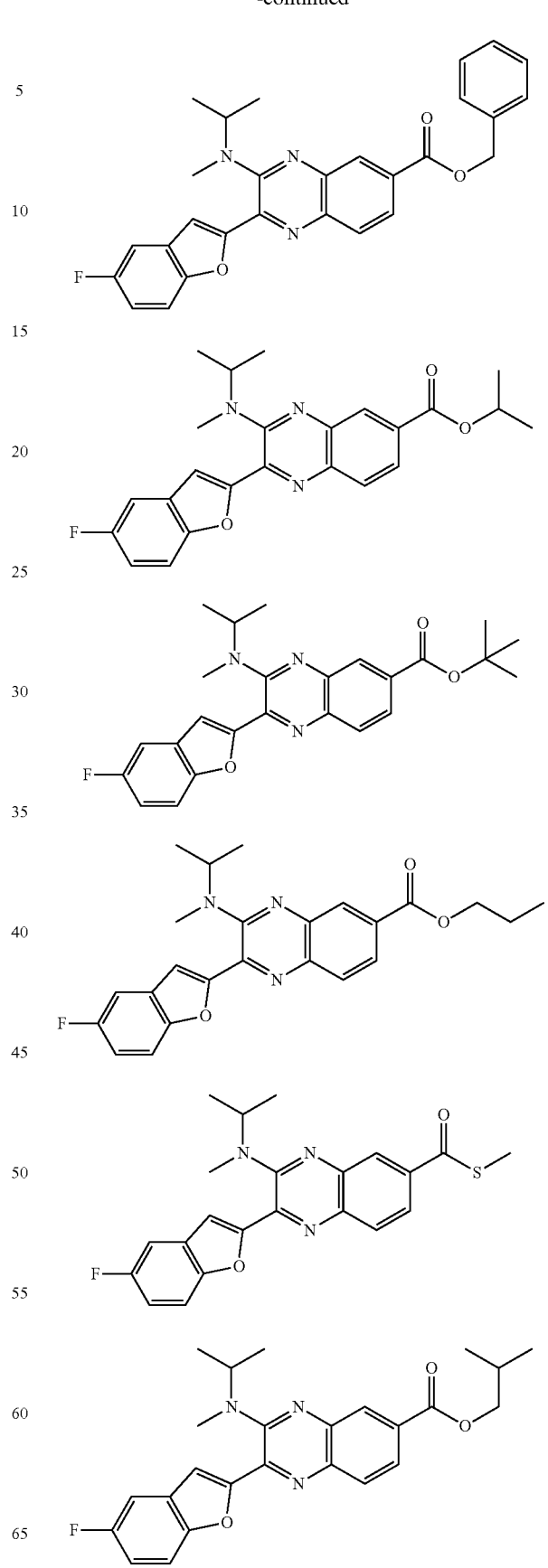

87
-continued
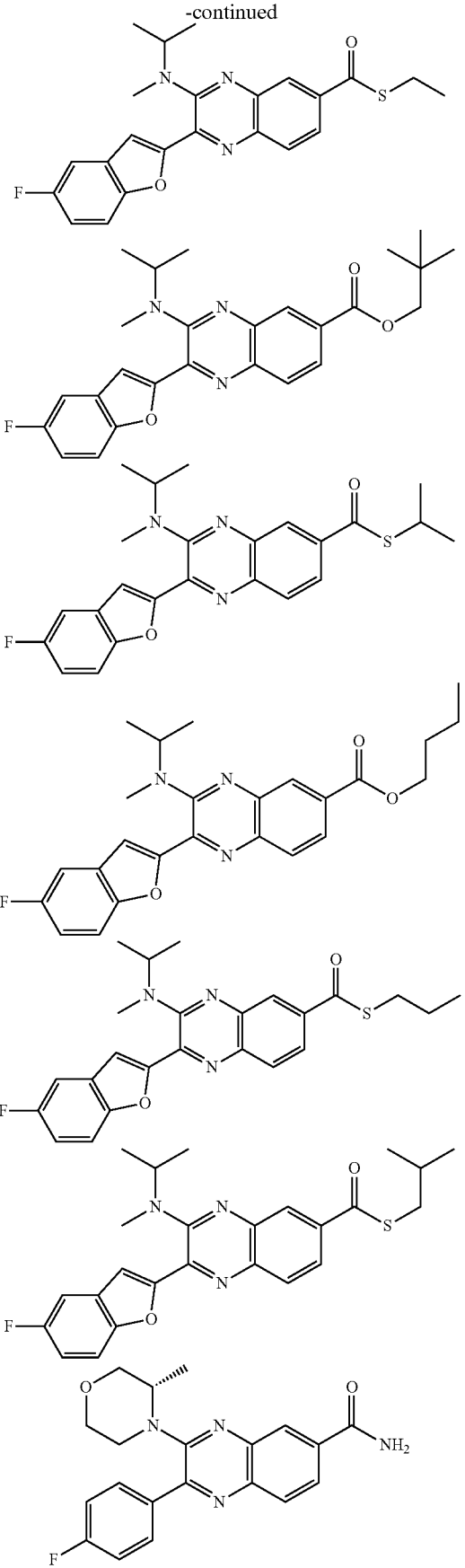
88
-continued
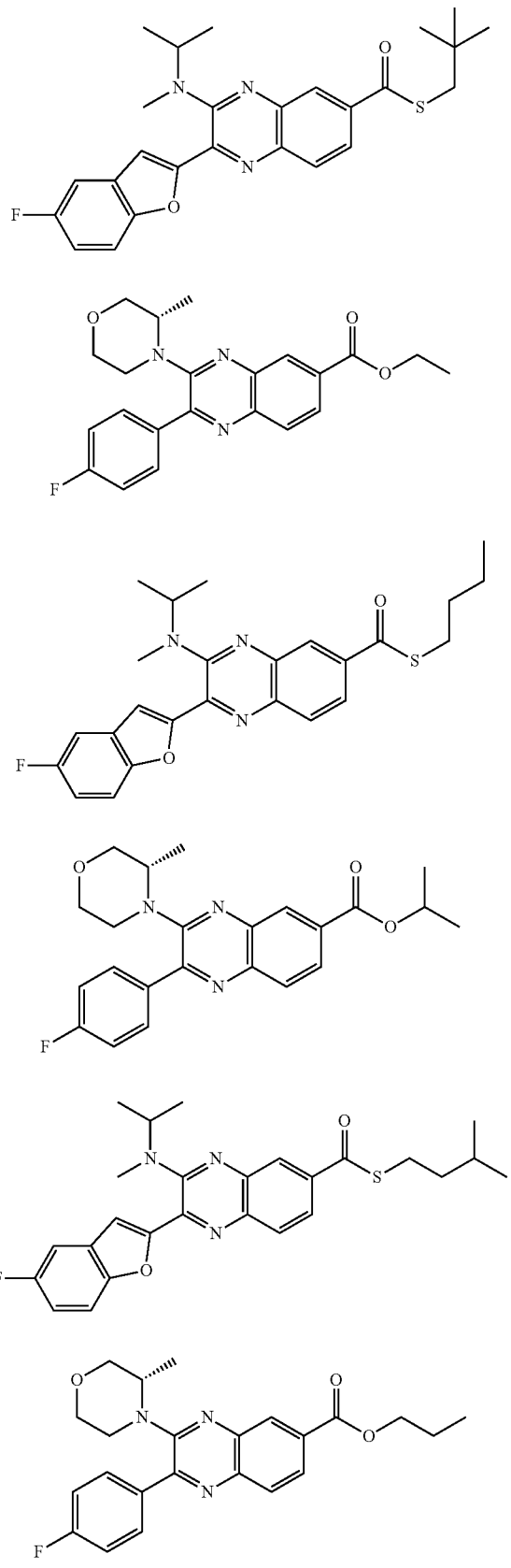

89
-continued
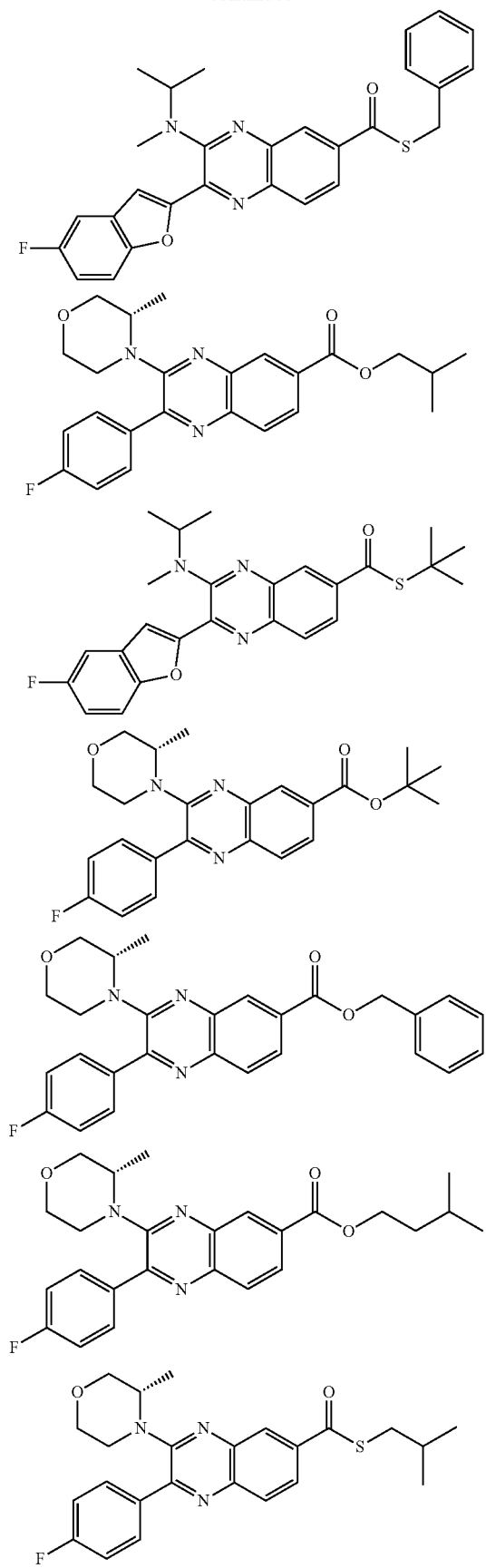
90
-continued
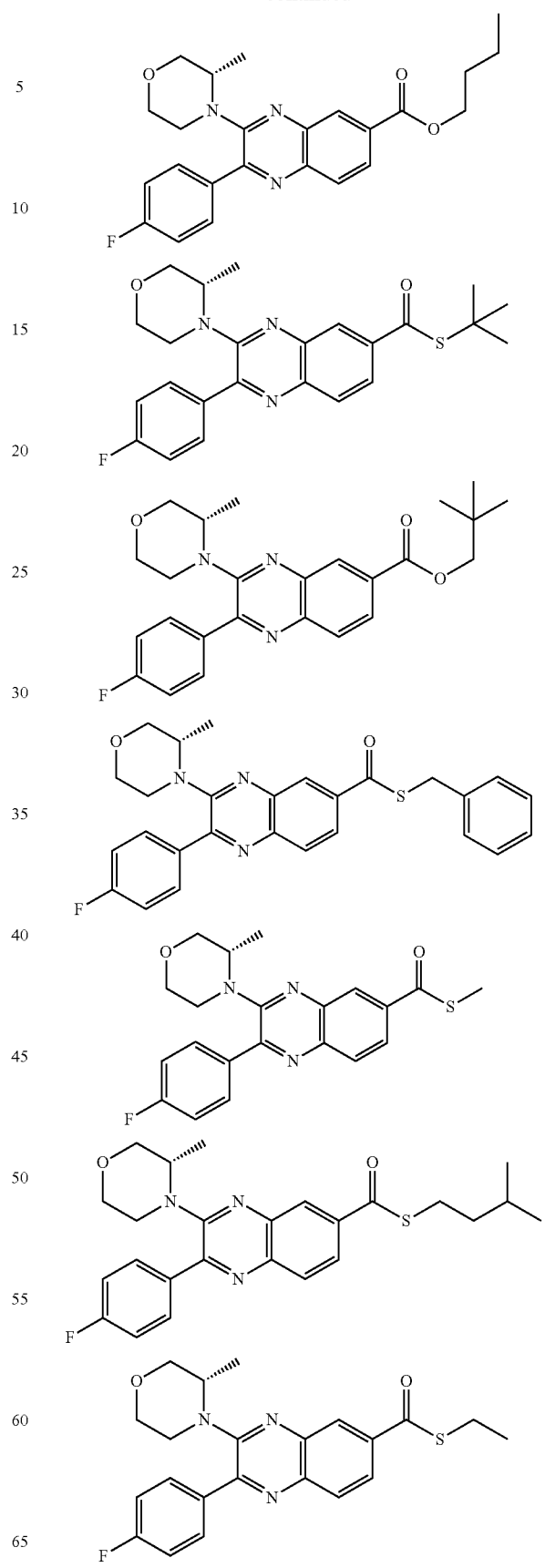

91
-continued
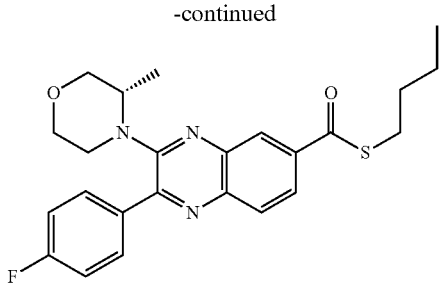
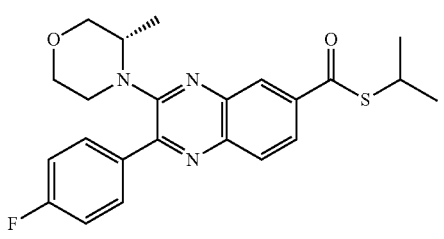
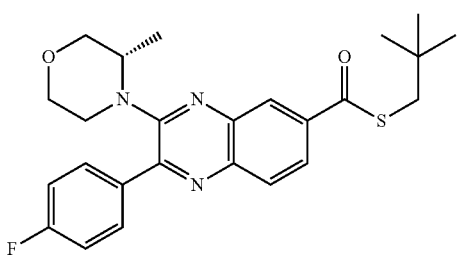
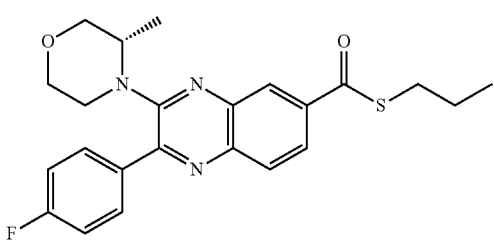
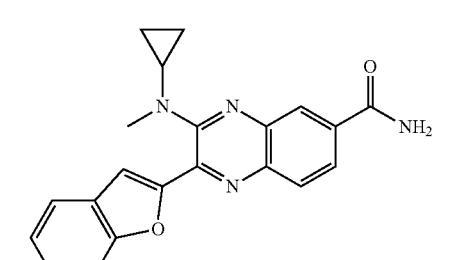
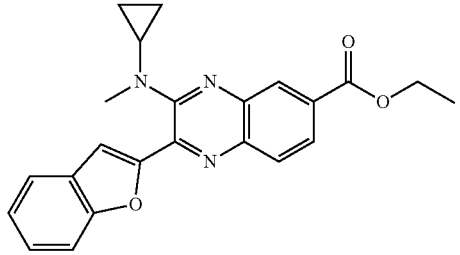
92
-continued
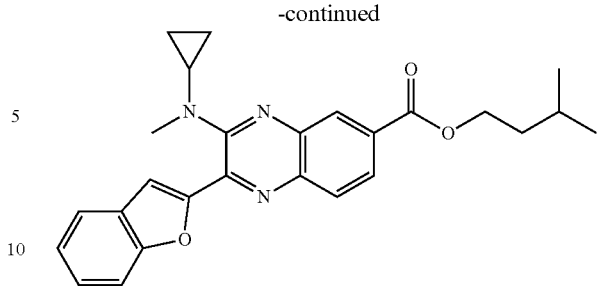
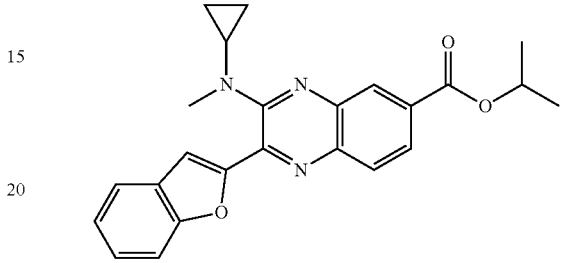
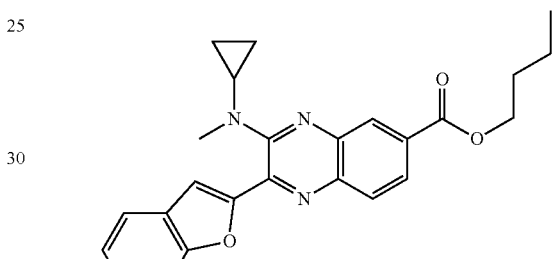
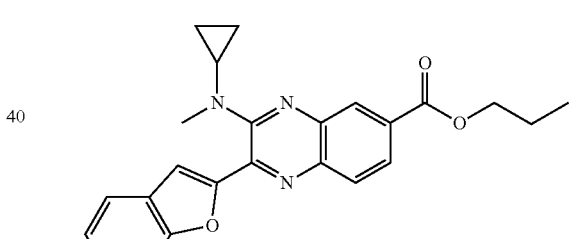
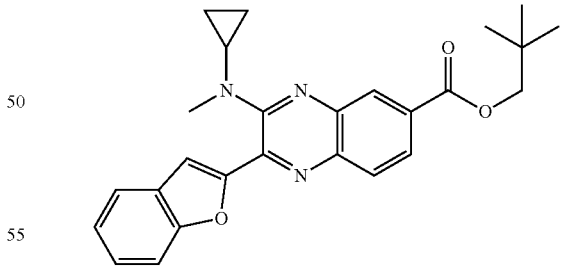
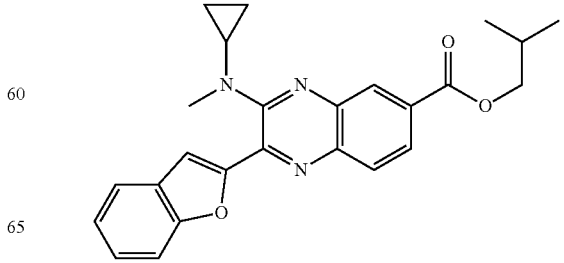

93
-continued
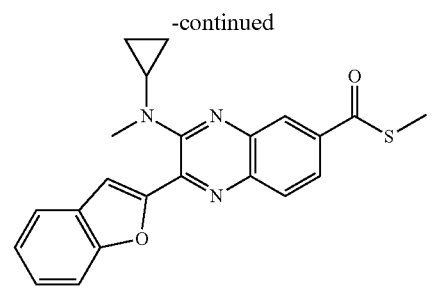
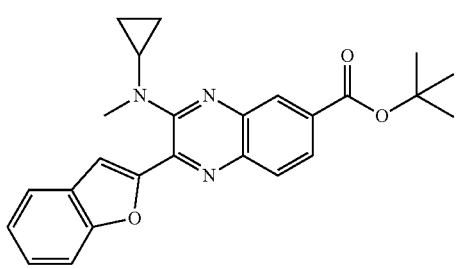
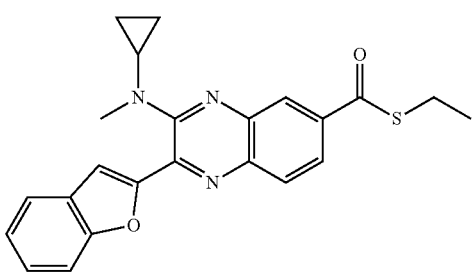
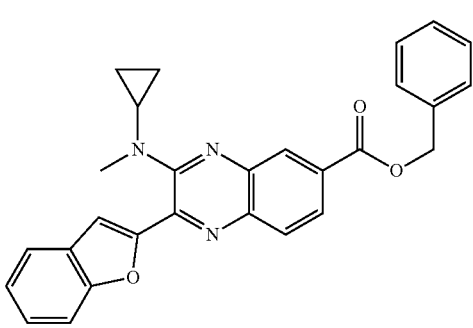
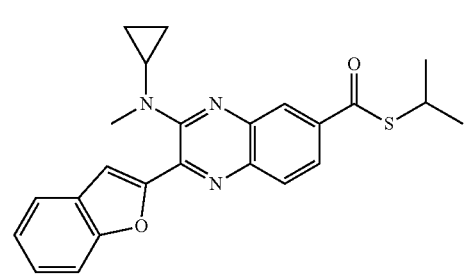
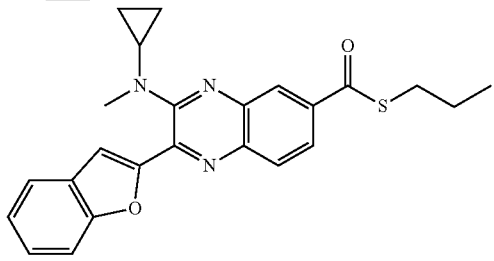
94
-continued
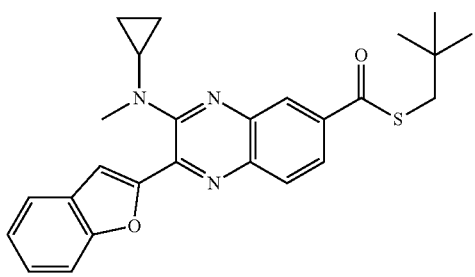
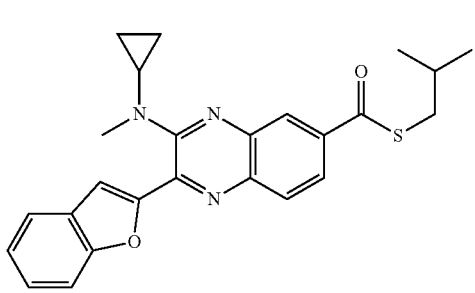
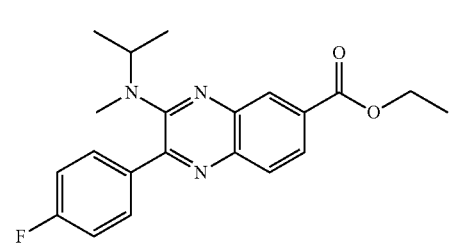
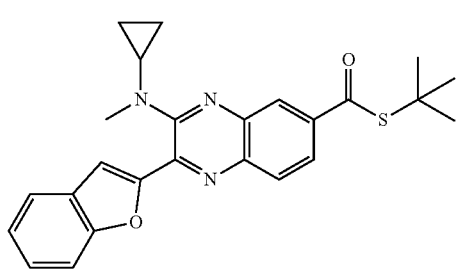
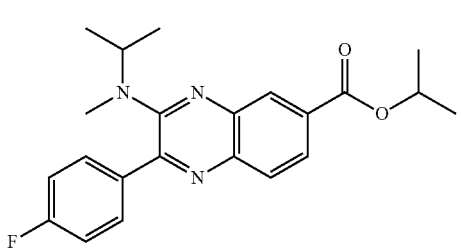
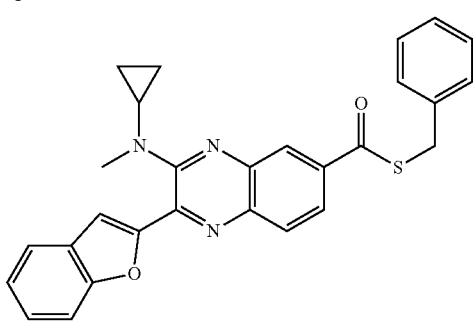

95
-continued
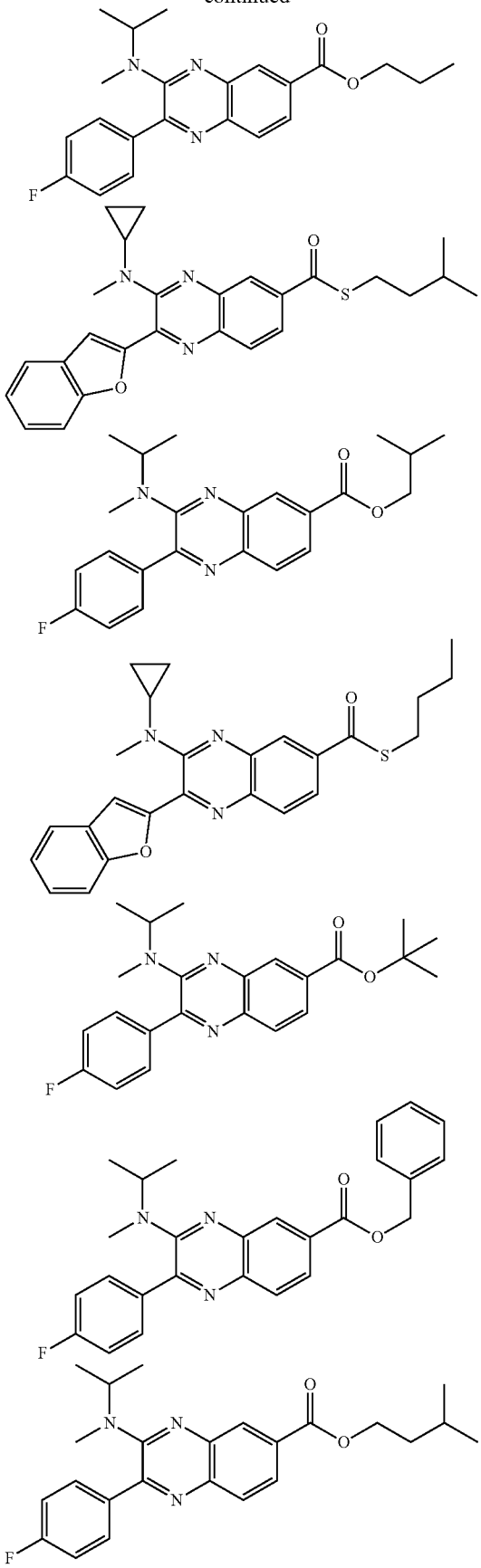
96
-continued
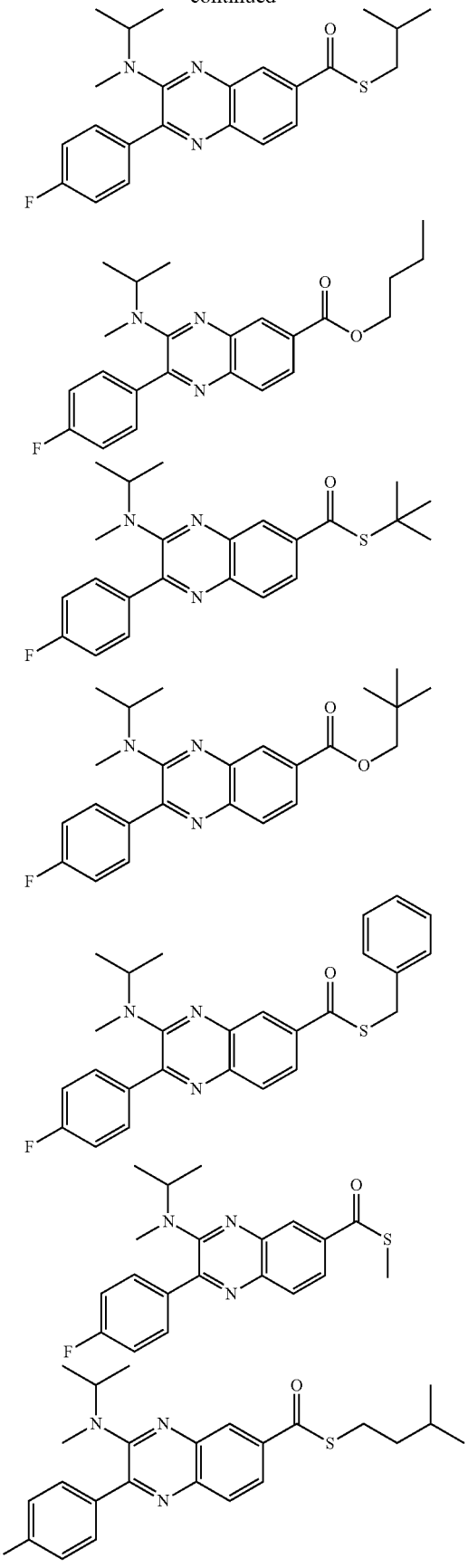

-continued

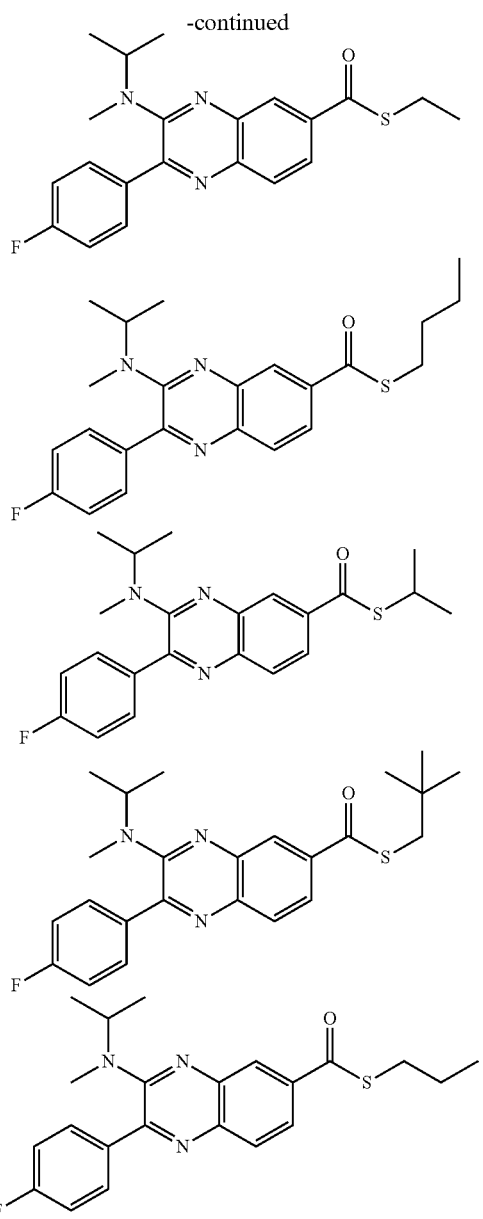

The activity of the compounds and prodrugs in Examples 1-7 as PASK modulators is illustrated in the following assays. The other compounds listed above, which have not yet been made and/or tested, are predicted to have activity in these assays as well.

BIOCHEMICAL ASSAY FOR hPASK ACTIVITY

PASK ATP Radiochemical Assay

Purified PASK (UniProt #Q96RG2; human recombinant N-terminal GST tagged construct, residues 879-1323) from insect cells (final concentration 5 nM) is added to freshly prepared Base Reaction Buffer containing 20 mM HEPES (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO and Myelin Basic Protein (20 µM final). Test compounds in DMSO are then added and the mixture, followed by delivery of $^{33}$P-ATP (specific activity 0.01 µCi/µl final) to initiate the reaction. The kinase reaction is incubated for 120 min at room temperature. The entire reaction mixture is washed through onto a P81 Phosphocellulose paper and washed three times for 10 minutes in 75 mM phosphoric acid and once in methanol prior to drying and scintillation counting.

Results for this assay are shown below in Table 1.

TABLE 1

| Example # | IC$_{50}$ Kinase Domain<br>+ indicates ≤10 µm<br>− indicates >10 µm |
|---|---|
| 1 | + |
| 25 | + |
| 26 | + |
| 27 | + |
| 28 | + |
| 29 | + |
| 32 | + |
| 34 | + |

PAS Kinase FRET Assay

The aim of the FRET assay is to determine the inhibition potential of test compounds on targeted kinase. This assay platform provides a homogenous screening method for measuring kinase activity by quantitating the amount of phospho-substrate in solution following a kinase reaction.

In the presence of kinase and ATP, the Ulight-peptide is phosphorylated and captured by an anti-phospho-substrate antibody, which brings the Eu chelate donor and Ulight acceptor dyes into close proximity. Upon excitation at 340 nm, the Eu chelate transfers its energy to the Ulight dye, resulting in a fluorescent light emission at 665 nm.

Titration of kinase at 1 mM ATP was achieved via the following protocol. After making serial three-fold dilutions of PASK (Invitrogen) in reaction buffer across the plate; 5 µl of kinase dilution and 5 µl substrate/ATP mix were added to the wells of the white Optiplate-384 (PerkinElmer). The contents of the plate were incubated at RT for 1 h. The reaction was stopped by adding 5 µl of stop solution to each test well followed by mixing and incubation at RT for 10 minutes. 5 µl of detection mix (detection antibody diluted in detection butler) was added; the contents of the plate were mixed and then incubated in the dark for 1 hour at RT. The signal was recorded at TR-FRET mode (665 nm/615 nm), The results were graphed to calculate the EC$_{50}$.

Titration of ATP at the EC$_{50}$ concentration of kinase to determine ATP Km,app. was performed using the following method. After making serial dilutions of ATP (Invitrogen), 5 µl of ATP dilution and 5 µl substrate/kinase mix were added to the wells of the white Optiplate-384 (PerkinElmer). The contents of the plate were and incubated at RT for 1 h. The reaction was stopped by adding 5 µl of stop solution to each test well followed by mixing and incubation at RT for 10 minutes. 5 µl of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the EC$_{50}$ as the ATP Km,app.

Compound screening was done via the following method. 10 mM stock solution of test compound in DMSO was prepared by dissolving test compound in DMSO at RT for 1 hour, and then sonicating at 100% output for 8 minutes. If compound is not soluble under this condition, it was diluted to 3 mM. Kinase reaction buffer was prepared containing 10 mM MgCl$_2$, 50 mM HEPES, 1 EGTA, 0.01% TWEEN-20, 2 mM WT. Serial dilutions of the test compounds were prepared at 4× final assay concentrations using Freedom EVO200® dispensing system as follows: 12×10$^{-5}$M, 4×10$^{-5}$ M, 1.33×10$^{-5}$M, 4.44×10$^{-6}$ M. 1.48×10$^{-6}$ M, 4.92×10$^{-7}$ M, 1.65×10$^{-7}$ M, 5.48×10$^{-7}$M, 1.82×10$^{-8}$ M, 6.09×10$^{-9}$, 2.03×10$^{-9}$ M. Test compounds (2.5 µl at 4× the final assay concentration) was added to wells using Freedom EVO200® dispensing system. As a positive control, 2.5 µl of positive compound was added to assay wells, and 2.5 µl of DMSO to assay wells as vehicle control. Kinase solution was prepared in reaction buffer at 2× final assay concentration. Kinase solution (5 µl) was added to each well of the assay plate. The substrate and ATP solution was prepared in kinase reaction buffer at 4× final assay concentration. The kinase reaction was started by adding 2.5 µl of substrate+ATP mix solution to each well of the assay plate. The plate is mixed on a plate shaker; then covered and allowed to react for 2 hours in the dark at 25° C. without shaking. The reaction was stopped by adding 5 µl of stop solution to each test well followed by mixing and incubation at RT for 10 minutes in the dark. 5 µl of detection mix (detection antibody diluted in detection buffer) was added; the contents of the plate were mixed and then incubated in the dark for 1 hour at RT. The signal was recorded at TR-FRET mode (665 nm/615 nm).

Results are shown below in Table 2.

TABLE 2

| Example # | IC$_{50}$ Kinase Domain<br>+ indicates ≤10 µm<br>− indicates >10 µm |
|---|---|
| 1 | + |
| 24 | + |
| 26 | + |
| 28 | + |
| 29 | + |
| 30 | + |
| 31 | + |
| 32 | + |
| 33 | + |
| 38 | + |

PAS Kinase Luminescence Assay

One assay for purified hPASK activity utilizes the Kinase-Glo Luminescent Kinase Assay (Promega), which quantifies the amount of ATP remaining in solution following kinase reaction. The assay is carried out in a 96-well plate format and is performed by adding a volume of Kinase-Glo Reagent (Promega, catalog #V3771) equal to the volume of solution in the well of a completed kinase reaction. Kinase-Glo reagent contains Luciferase and its substrate. After addition to a kinase reaction it allows to measure luminescence. The amount of ATP left in solution at the time of Kinase-Glo Plus addition is directly proportional to the luminescence that is measured in each well, and inversely correlated with kinase activity.

Purified hPASK from insect cells (0.02 µg) is added to a 50 µL reaction mix containing 40 mM HEPES (pH 7.0), 100 mM KCl, 5 mM MgCl$_2$, 1 mM DTT and 1 µg of MBP protein. Inhibitory compounds are then added and the mixture is incubated for 10 min at 25° C. before adding 5 µL of ATP (at desired concentration). The reaction is allowed to proceed at 25° C. for 1 hour before adding 50 µL of Kinase-Glo reagent. The luminescence is measured as soon as 10 minutes after Kinase-Glo reagent is added.

Results are shown below in Table 3.

TABLE 3

| Example # | IC$_{50}$ Kinase Domain<br>+ indicates ≤10 µm<br>− indicates >10 µm |
|---|---|
| 34 | + |
| 35 | + |
| 36 | − |
| 37 | + |

Cell Assay for hPASK Activity

Use of Phospho-AKT Substrate Antibody to Determine PAS Kinase Activity

The assay applies the ability of PASK to autophosphorylate in vivo on the sequence recognized by phospho-Akt substrate antibody (110B7E, Cell Signaling). Cell line HEK293T is transfected with vector (pcDNA 3.1-PASK) expressing V5-tagged wilde-type of PASK. Transfected cells are then treated with putative inhibitors of PASK. Twenty-four hours post treatment cells are lysed and PASK is separated from cellular proteins by immunoprecipitation with V5-conjugated beads (Sigma). PASK is released from immunocomlexes, separated on the SDS-PAGE gel and transferred on nitrocellulose membrane. Fraction of PASK phosphorylated on phospho-AKT Substrate site(s) is determined by probing with phospho-AKT antibody and normalized to total PASK level present in the same immunoprecipitates. We have shown the correlation between phosphorylation of phospho-AKT Substrate sequence and inhibition of PASK activity in vivo.

HEK293T cells are maintained and propagated in 10 cm dish in 10 ml of DMEM/10% FBS, split and re-seeded in 6 well plate (10$^6$ cells/well) in 2 ml of DMEM/10% FBS. Cells are transfected 18 hours post plating with 1ug of construct expressing wild-type of hPASK using lipofectamine 2000 according to the manufacturers protocol (Invitrogen). Cells expressing PASK are treated either with DMSO or PASK inhibitors. Twenty-four hours post transfection, medium is aspirated and cells are lysed in 0.8 ml of lysis buffer (20 mM Na2HPO4, 0.5% Triton, 0.1% SDS, 0.02% azide, Proteases Inhibitors, Phosphatases Inhibitors—1 mM NaF, 1 mM glycerphosphate, 1 mM NaOV) and immunoprecipitated with V5AB conjugated beads. Immunocomplexes are washed with buffer (20 mM Na2HPO4, 0.5% Triton X-100, 0.1% SDS, 0.02% NaN3) containing high salt (1M NaCl and 0.1% BSA) followed by low salt (150 mM NaCl). Immunoprecipitated PASK is released from immunocomplexes and separated by SDS-PAGE and transferred on nitrocellulose membrane (Western blot). Blots are probed subsequently with phospho-AKT Substrate Ab and V5 antibody. Intensities of the bands are quantitated and data normalized.

Results are shown below in Table 4.

TABLE 4

| Example # | AKT IC$_{50}$<br>+ indicates ≤10 µm<br>− indicates >10 µm |
|---|---|
| 1 | + |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising a compound of Formula (IV):

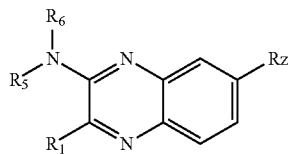

or a pharmaceutically acceptable salt or stereoisomer thereof, wherein:

Rz is tetrazolyl;

$R_1$ is chosen from aryl and heteroaryl, either of which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $SO_2R_{12}$, $SO_2NHR_{12}$, $CF_3$, and $OCF_3$;

$R_5$ and $R_6$ are independently chosen from hydrogen, $C_1$-$C_6$ alkyl, $C_3$-$C_7$ cycloalkyl, $C_3$-$C_7$ heterocycloalkyl, aryl, heteroaryl, aralkyl, and heteroaralkyl, any of which may be optionally substituted by substituents chosen from lower alkyl, lower heteroalkyl, lower heterocycloalkyl, lower haloalkyl, lower perhaloalkyl, lower perhaloalkoxy, lower cycloalkyl, phenyl, aryl, aralkyl, lower alkoxy, lower haloalkoxy, carboxyl, cyano, hydrogen, halogen, hydroxy, amino, lower alkylamino, amido, nitro, sulfonate, and sulfonic acid; and $R_{12}$, $R_{12a}$ and $R_{12b}$ are independently chosen from hydrogen, $C_1$-$C_6$ alkyl, aryl, heteroaryl, aralkyl, $CF_3$ and heteroaralkyl, any of which may be optionally substituted by substituents chosen from lower alkyl, lower heteroalkyl, lower heterocycloalkyl, lower haloalkyl, lower perhaloalkyl, lower perhaloalkoxy, lower cycloalkyl, phenyl, aryl, aralkyl, lower alkoxy, lower haloalkoxy, carboxyl, cyano, hydrogen, halogen, hydroxy, amino, lower alkylamino, amido, nitro, sulfonate, and sulfonic acid;

and a pharmaceutically acceptable carrier.

2. The pharmaceutical composition as recited in claim 1 wherein $R_1$ is aryl, which may be optionally substituted with one or more substituents chosen from hydrogen, halo, alkyl, alkenyl, alkynyl, cycloalkyl, haloalkyl, aryl, aralkyl, heterocyclyl, heteroaryl, heterarylalkyl, CN, alkoxy, alkylamino, dialkylamino, $NHSO_2R_{12}$, $NHSO_2NHR_{12}$, $NHCOR_{12}$, $NHCONHR_{12}$, $CONHR_{12}$, $CONR_{12a}R_{12b}$, hydroxy, $CF_3$, $SO_2R_{12}$, $NHSO_2R_{12}$, and $OCF_3$.

3. The pharmaceutical composition as recited in claim 2 wherein $R_1$ is aryl optionally substituted with one or more halo substituents.

4. The pharmaceutical composition as recited in claim 1 wherein $R_5$ and $R_6$ are independently chosen from hydrogen, $C_1$-$C_6$ alkyl, $C_3$-$C_7$ cycloalkyl, $C_3$-$C_7$ heterocycloalkyl, and aryl, any of which may be optionally substituted by substituents chosen from lower alkyl, lower heteroalkyl, lower heterocycloalkyl, lower haloalkyl, lower perhaloalkyl, lower perhaloalkoxy, lower cycloalkyl, phenyl, aryl, aralkyl, lower alkoxy, lower haloalkoxy, carboxyl, cyano, hydrogen, halogen, hydroxy, amino, lower alkylamino, amido, nitro, sulfonate, and sulfonic acid.

5. A method for achieving an effect in a patient comprising the administration of a therapeutically effective amount of a pharmaceutical composition as recited in claim 1 to a patient, wherein the effect is selected from the group consisting of reduction of triglycerides, reduction of cholesterol, and reduction of hemoglobin A1c.

6. The method of claim 5 wherein said cholesterol is chosen from low-density lipoprotein and very low-density lipoprotein cholesterol.

7. The method of claim 5 wherein said triglycerides are chosen from plasma triglycerides and liver triglycerides.

8. A method of inhibiting purine-analog sensitive kinase comprising contacting purine-analog sensitive kinase with a pharmaceutical composition as recited in claim 1 to a patient in need thereof.

* * * * *